US 6,670,373 B1

(12) United States Patent
Bonjouklian et al.

(10) Patent No.: US 6,670,373 B1
(45) Date of Patent: Dec. 30, 2003

(54) COMPOUNDS AND METHOD FOR INHIBITING MRP1

(75) Inventors: Rosanne Bonjouklian, Zionsville, IN (US); Douglas Webb Johnson, Zionsville, IN (US); Peter Ambrose Lander, Indianapolis, IN (US); Mark Christopher Lohman, Boulder, CO (US); Vinod Francis Patel, Acton, MA (US); Sreenivasarao Vepachedu, Hinsdale, IL (US); Yongping Xie, Naperville, IL (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/088,721

(22) PCT Filed: Sep. 22, 2000

(86) PCT No.: PCT/US00/21980

§ 371 (c)(1),
(2), (4) Date: Jul. 2, 2002

(87) PCT Pub. No.: WO01/27116

PCT Pub. Date: Apr. 19, 2001

Related U.S. Application Data
(60) Provisional application No. 60/169,784, filed on Dec. 9, 1999, and provisional application No. 60/158,175, filed on Oct. 7, 1999.

(51) Int. Cl.[7] ............... A61K 31/4745; A61K 31/4355; C07D 498/04; C07D 471/04; A61P 35/00
(52) U.S. Cl. .......... 514/293; 514/232.8; 546/82; 546/83; 544/126
(58) Field of Search .......... 546/83, 82; 544/126; 514/293, 232.8

(56) References Cited

U.S. PATENT DOCUMENTS

| | | | |
|---|---|---|---|
| 5,451,585 A | 9/1995 | Albaugh | 514/282 |
| 5,717,092 A | 2/1998 | Armistead et al. | 544/129 |
| 6,369,070 B1 * | 4/2002 | Gruber et al. | 514/293 |

OTHER PUBLICATIONS

Marbeuf–Gueye C et al. (1998) Molecular Pharmacology 53:141–147.*
Lawrence DS et al. (2001) J. Med. Chem. 44:594–601.*
Germann UA et al. (1997) Anticancer Drugs 8:141–155.*

* cited by examiner

*Primary Examiner*—Evelyn Mei Huang
(74) *Attorney, Agent, or Firm*—Tina M. Tucker

(57) ABSTRACT

The present invention relates to a compound of formula (I), which is useful for inhibiting resistant neoplasms where the resistance is conferred in part or in total by MRP1.

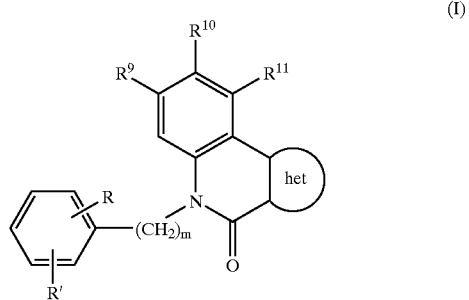

27 Claims, No Drawings

COMPOUNDS AND METHOD FOR INHIBITING MRP1

This application is the U.S. National Stage filing of PCT/US00/21980, filed Sep. 22, 2000, which claims the benefit of U.S. Provisional Applications Ser. No. 60/158,175, filed on Oct. 7, 1999, and No. 60/169,784, filed on Dec. 9, 1999.

BACKGROUND

Along with surgery and radiotherapy, chemotherapy continues to be an effective therapy for many cancers. In fact, several types of cancer, such as Hodgkin's disease, large cell lymphoma, acute lymphocytic leukemia, testicular cancer and early stage breast cancer, are now considered to curable by chemotherapy. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", *Cancer Research*, 54:5902–5910, 1994. Doxorubicin, daunorubicin, epirubicin, vincristine, and etoposide are substrates of MRP1, i.e., MRP1 can bind to these oncolytics and redistribute them away from their site of action, the nucleus, and out of the cell. Id. and Marquardt, D., and Center, M. S., *Cancer Research*, 52:3157, 1992.

Doxorubicin, daunorubicin, and epirubicin are members of the anthracycline class of oncolytics. They are isolates of various strains of Streptomyces and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

Additionally, PCT publications WO99/51236, WO99/51228, and WO99/51227 disclose certain compounds known to be inhibitors of MRP1.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to coadminister an agent that is a selective inhibitor of that protein. It is, therefore, desirable to provide compounds that are selective inhibitors of MDR1 or MRP1.

This invention relates to novel compounds, which inhibit MRP1 and are therefore useful for the treatment of MRP1 conferred MDR in a resistant neoplasm, or a neoplasm susceptible to resistance in a mammal.

SUMMARY OF THE INVENTION

The present invention relates to a compound of formula:

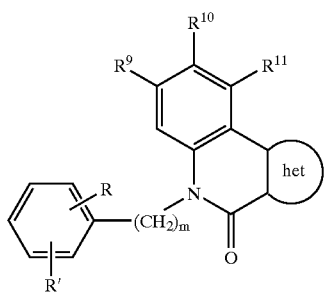

where:

het is a five (5) membered heteroaryl ring containing N and a second heteroatom selected from N, O, or S;
   wherein the non-fused carbon atom of the heteroaryl ring is optionally substituted with $R^b$ and; provided that when het is pyrazole or imidazole, the saturated nitrogen of the het ring is optionally substituted with $R^a$;
   wherein $R^b$ is $C_1$–$C_6$ alkyl, aryl, substituted aryl, heterocycle, substituted heterocycle, an amino acid ester, $CH_2OH$, $CH_2O$-heterocycle, halo, $CH_2N_3$, $CH_2SR^1$, $CH_2NR^4R^5$, $OR^1$, $SR^{12}$, $S(CH_2)_n$-phenyl, or $NR^4R^5$, and
   $R^a$ is $C_1$–$C_4$ alkyl, R is $(CH_2)_{m'}CHR^1NHR^2$, $O(CH_2)_2NHR^2$, $(CH_2)_{m'}COR^3$, $NHR^2$, and $(CH_2)_{m'}CHR^1NR^4R^5$;

R' is hydrogen, hydroxy, or $O(C_1$–$C_6$ alkyl optionally substituted with phenyl or $C_3$–$C_7$ cycloalkyl);

m and m' are independently at each occurrence 0, 1, or 2;

$R^1$ is independently at each occurrence hydrogen or $C_1$–$C_6$ alkyl;

$R^2$ is hydrogen, $COR^6$, $CH_2R^{6'}$, $SO_2R^7$, or a moiety of the formula $$-\underset{\substack{\|\\S}}{C}-NHR^7;$$

$R^3$ is hydrogen, hydroxy, $C_1$–$C_6$ alkoxy, an amino acid ester, an amino acid, or $NR^4R^5$;

$R^4$ is hydrogen or $C_1$–$C_6$ alkyl;

$R^5$ is hydrogen, $C_1$–$C_6$ alkyl, $C_6$–$C_{10}$ bicycloalkyl, ($C_1$–$C_4$ alkyl)-phenyl, ($C_1$–$C_4$ alkyl)—$CO_2R^1$, $CH_2CO_2R^1$, aryl, substituted aryl, $(CH_2)_n CHR^8 NHC(O)OC(CH_3)_3$, $(CH_2)_n NH_2$, $(CH_2)_2 NHCOR^6$, $(CH_2)_2 OR^1$, $(CH_2)_q$-heterocycle, $(CH_2)_q$-substituted heterocycle, or $R^4$ and $R^5$, together with the nitrogen to which they are attached, combine to form a pyrrolidin-1-yl, piperidin-1-yl, hexamethyleneimin-1-yl, or morpholin-4-yl ring;

n is 1, 2, 3, or 4;

q is 0, 1, 2, or 3;

$R^6$ is $C_1$–$C_6$ alkyl, substituted $C_3$–$C_6$ cycloalkyl, aryl, substituted aryl, tert-butoxy, $(CH_2)_q$-heterocycle, $(CH_2)_q$-substituted heterocycle, $(CH_2)_n S(O)_r R^1$, $C(CH_3)_2 CH_2 N(R^1)_2$, $(CH_2)_n CHR^8 NHC(O)OC(CH_3)_3$, $(CH_2)_n CHR^8 NH_2$, $(CH_2)_2 NH$-aryl, or $NHR^7$;

$R^{6'}$ is $C_1$–$C_6$ alkyl, substituted $C_3$–$C_6$ cycloalkyl, aryl, substituted aryl, $(CH_2)_q$-heterocycle, $(CH_2)_q$-substituted heterocycle, $(CH_2)_n S(O)_r R^1$, $C(CH_3)_2 CH_2 N(R^1)_2$, $(CH_2)_n CHR^8 NH$—$C(O)OC(CH_3)_3$, $(CH_2)_n CHR^8 NH_2$, or $(CH_2)_2 NH$-aryl;

r is 0, 1, or 2;

$R^7$ is $C_1$–$C_6$ alkyl, phenyl, or substituted phenyl;

$R^8$ is hydrogen or $CO_2R^1$; and $R^9$, $R^{10}$, and $R^{11}$ are independently at each occurrence hydrogen, halo, $CO_2R^1$, aryl, substituted aryl, thiophene, $C_1$–$C_4$ alkoxy, ($C_1$–$C_3$ alkyl)-phenyl, or $C_2$–$C_6$ alkenyl;

$R^{12}$ is $C_1$–$C_6$ alkyl, ($C_1$–$C_4$ alkyl)-phenyl, aryl, substituted aryl, heterocycle or substituted heterocycle; or a pharmaceutical salt thereof; provided that if $R^9$ and $R^{10}$ are hydrogen and $R^{11}$ is chloro, then het is not

[structure: isoxazole ring with Me substituent]

The present invention further relates to a method of inhibiting MRP1 in a mammal which comprises administering to a mammal in need thereof an effective amount of a compound of formula I.

In another embodiment, the present invention relates to a method of inhibiting a resistant neoplasm, or a neoplasm susceptible to resistance in a mammal which comprises administering to a mammal in need thereof an effective amount of a compound of formula I in combination with an effective amount of an oncolytic agent.

The present invention also relates to a pharmaceutical formulation comprising a compound of formula I in combination with one or more oncolytics, pharmaceutical carriers, diluents, or excipients therefor.

Furthermore, the invention relates to the use of a compound of formula I, or a pharmaceutically acceptable salt thereof, for the manufacture of a medicament for inhibiting a resistant neoplasm, or a neoplasm susceptible to resistance in a mammal.

Furthermore, the invention relates to the use of a compound of formula I, or a pharmaceutically acceptable salt thereof, for the manufacture of a medicament for inhibiting MRP1.

Furthermore, the invention relates to the use of a compound of formula I, or a pharmaceutically acceptable salt thereof, for the manufacture of a medicament for inhibiting MRP1 conferred MDR in a resistant neoplasm, or a neoplasm susceptible to resistance in a mammal.

Furthermore, the invention relates to the use of a compound of formula I in therapy.

DETAILED DESCRIPTION OF THE INVENTION

The current invention concerns the discovery that compounds of formula I are selective inhibitors of multidrug resistant protein (MRP1), and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic agent" refers to an amount of oncolytic agent capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm, which is resistant to chemotherapy where that resistance is conferred in part, or in total, by MRP1. Such neoplasms include, but are not limited to, neoplasms of the bladder, bone, breast, lung (small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm, which is "susceptible to resistance", is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytic agents where at least one oncolytic agent is a substrate of MRP1. A "substrate of MRP1" is an oncolytic that binds to MRP1 and is redistributed away from the oncolytics site of action the nucleus of the neoplasm) and out of the cell, thus, rendering the therapy less effective. Preferred oncolytic agents are doxorubicin, daunorubicin, epirubicin, vincristine, and etoposide.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight or branched saturated hydrocarbon containing from 1 to 6 carbon atoms. Additionally, the term "$C_1$–$C_6$ alkyl" includes $C_1$–$C_4$ alkyl groups and $C_3$–$C_6$ cycloalkyls. The term "$C_1$–$C_6$ alkyl" includes, but is not limited to, cyclopentyl, pentyl, hexyl, cyclohexyl, and the like. The term "$C_3$–$C_6$ cycloalkyl" refers to cyclopropyl, cyclobutyl, cyclopentyl, and cyclohexyl. The term "$C_5$–$C_7$ cycloalkyl" refers to cyclopentyl, cyclohexyl, and cycloheptyl. The term "$C_6$–$C_{10}$ bicycloalkyl" refers to bicyclo-[2.1.1]hexanyl, [2.2.1]heptanyl, [3.2.1]octanyl, [2.2.2]octanyl, [3.2.2] nonanyl, [3.3.1]nonanyl, [3.3.2]decanyl, and [4.3.1]decanyl ring systems.

The terms "$C_1$–$C_4$ alkoxy" and "$C_1$–$C_6$ alkoxy" refer to moieties of the formula O—($C_1$–$C_4$ alkyl) and O—($C_1$–$C_6$ alkyl) respectively.

The term "substituted $C_3$–$C_6$ cycloalkyl" refers to a $C_3$–$C_6$ cycloalkyl substituted once with a phenyl, substituted phenyl, or $CO_2R^1$ group.

The term "halo" or "halide" refers to fluoro, chloro, bromo, and iodo.

The term "aryl" refers to phenyl, benzyl, and naphthyl.

The terms "substituted aryl" refers to a phenyl, benzyl, and naphthyl group respectively substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro.

The term "heterocycle" is taken to mean stable unsaturated and saturated 5- and 6-membered rings containing from 1 to 3 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —$S(O)_m$—($C_1$–$C_4$ alkyl) and —$S(O)_m$-phenyl where m is 0, 1 or 2. Saturated rings include, for example, pyrrolidinyl, piperidinyl, piperazinyl, tetrahydrofuryl, oxazolidinyl, dioxanyl, pyranyl, and the like. Benzofused saturated rings include indolinyl, 1,2,3,4-tetrahydroquinolinyl, 1,2,3,4-tetrahydroisoquinolinyl and the like. Unsaturated rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused unsaturated rings include isoquinolinyl, benzoxazolyl, benzthiazolyl, quinolinyl, benzofuranyl, thionaphthyl, indolyl and the like.

The term "heteroaryl" is taken to mean an unsaturated or benzofused unsaturated heterocycle as defined in the previous paragraph.

The term "substituted heterocycle" refers to a heterocyclic ring substituted 1 or 2 times independently with a $C_1$–$C_6$ alkyl, halo, benzyl, phenyl, trifluoromethyl. Saturated heterocyclic rings may be additionally substituted 1 or 2 times with an oxo group, however, total substitution of the saturated heterocyclic ring may not exceed two substituents.

The term "amino acid" refers to a chemical unit made up of both a basic amino group and an acidic carboxyl group.

Examples of amino acids include alanine, asparagine, cysteine, glutamine, glycine, isoleucine, leusine, methionine, phenylalanine, proline, serine threonine, tryptophan, tyrosine, valine, aspartic acid, glutamic acid, arginine, histidine, and lysine.

The term "amino acid ester" as used in this specification refers to an amino acid where the carboxy group is substituted with a $C_1$–$C_6$ alkyl group. That is, the alkyl group when taken together with the carboxy group forms a $C_1$–$C_6$ alkyl ester. A skilled artisan would appreciate that some amino acids have two carboxy groups that may be substituted with a $C_1$–$C_6$ alkyl group, for example, aspartic acid and glutamic acid. This invention contemplates the possibility of amino acid mono- or diesters in these circumstances.

The term "protecting group" (Pg) refers to an amino protecting group or a hydroxy protecting group. The species of protecting group will be evident from whether the "Pg" group is attached to a nitrogen atom (amino protecting group) or attached to an oxygen atom (hydroxy protecting group).

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reaction (s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, "Protective Groups in Organic Synthesis", John Wiley and Sons, New York, N.Y., 1991, Chapter 7 hereafter referred to as "Greene". A preferred amino protecting group is t-butyloxycarbonyl.

The term "hydroxy protecting group" denotes a group understood by one skilled in the organic chemical arts of the type described in Chapter 2 of Greene. Representative hydroxy protecting groups include, for example, ether groups including methyl and substituted methyl ether groups such as methyl ether, methoxymethyl ether, methylthiomethyl ether, tert-buylthiomethyl ether, (phenyldimethylsilyl) methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)-ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl-, triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono-, di-, and trichloroacetate esters, phenoxyacetate ester, and p-chlorophenoxyacetate and the like. The species of hydroxy protecting group employed is not critical so long as the derivatized hydroxy group is stable to the conditions of subsequent reaction(s) on other positions of the intermediate molecule and can be selectively removed at the appropriate point without disrupting the remainder of the molecule including any other hydroxy protecting group(s).

The term "carbonyl activating group" refers to a substituent of a carbonyl that increases the susceptibility of that carbonyl to nucleophilic addition. Such groups include, but are not limited to, alkoxy, aryloxy, nitrogen containing unsaturated heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenylsulfonate, and the like; and halides especially chloride, bromide, or iodide.

The term "carbonyl activating reagent" refers to a reagent that converts the carbonyl of a carboxylic acid group to one that is more prone to nucleophilic addition and includes, but is not limited to, such reagents as those found in "The Peptides", Gross and Meienhofer, Eds., Academic Press (1979), Ch. 2 and M. Bodanszky, "Principles of Peptide Synthesis", $2^{nd}$ Ed., Springer-Verlag Berlin Heidelberg, 1993, hereafter referred to as "The Peptides" and "Peptide Synthesis" respectively. Specifically, carbonyl activating reagents include thionyl bromide, thionyl chloride, oxalyl chloride, and the like; alcohols such as nitrophenol, pentachlorophenol, and the like; amines such as N-hydroxy-N-methoxyamine and the like; acid halides such as acetic, formic, methanesulfonic, ethanesulfonic, benzenesulfonic, or p-tolylsulfonic acid halide, and the like; and compounds such as 1,1'-carbonyldiimidazole, benzotriazole, imidazole, N-hydroxysuccinimide, dicyclohexylcarbodiimide, and the like.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of formula I prepared by reaction of a compound of formula I with a mineral or organic base. For exemplification of pharmaceutical base addition salts see, e.g., Berge, S. M, Bighley, L. D., and Monkhouse, D. C., *J. Pharm. Sci.*, 66:1, 1977. This invention also contemplates pharmaceutical base addition salts of compounds of formula I. The skilled artisan would appreciate that some compounds of formula I may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of formula I.

While all of the compounds of the present invention are useful, certain of the compounds are particularly interesting and are preferred. The following listing sets out several groups of preferred compounds. It will be understood that each of the listings may be combined with other listings to create additional groups of preferred embodiments.

i. m is 0;
ii. R is at the meta position;
iii. R is $(CH_2)_{m'}CHR^1NHR^2$;
iv. R is $(CH_2)_{m'}COR^3$;
v. R is $(CH_2)_{m'}CHR^1NR^4R^5$;
vi. m' is 0;
vii. m' is 1;
viii. $R^1$ is methyl;
ix. $R^1$ is hydrogen;
x. $R^2$ is 3,4,5-trimethoxyphenylmethyl;
xi. $R^3$ is (3,4,5-trimethoxyphenyl)amino;
xii. $R^3$ is (4-aminosulfonylphenyl)amino;
xiii. $R^3$ is (6-methoxyquinolin-8-yl)amino;
xiv. $R^4$ is hydrogen;
xv. $R^5$ is 5-methylisoxazol-3-yl;

xvi. $R^5$ is 3,5-dimethoxy-4-hydroxybenzyl;
xvii. $R^5$ is 3,4,5-trimethoxyphenyl;
xviii. R' is hydrogen;
xix. $R^9$ is hydrogen;
xx. $R^9$ is halo;
xxi. $R^{10}$ is hydrogen;
xxii. $R^{11}$ is halo;
xxiii. $R^{11}$ is $C_1$–$C_4$ alkoxy;
xxiv. $R^{11}$ is optionally substituted aryl;
xxv. R is $(CH_2)_m CHR^1 NHR^2$;
xxvi. R is $O(CH_2)_2 NHR^2$;
xxvii. R is $(CH_2)_{m'} COR^3$;
xxviii. R is $NHR^2$;
xxix. R is $(CH_2)_m CHR^1 NR^4 R^5$;
xxx. R' is hydroxy;
xxxi. R' is $O(C_1$–$C_6$ alkyl optionally substituted with phenyl or $C_3$–$C_7$ cycloalkyl);
xxxii. m is 1;
xxxiii. m is 2;
xxxiv. m' is 2;
xxxv. $R^1$ is $C_1$–$C_6$ alkyl;
xxxvi. $R^2$ is hydrogen;
xxxvii. $R^2$ is $COR^6$;
xxxviii. $R^2$ is $CH_2 R^{6'}$;
xxxix. $R^2$ is $SO_2 R^7$;
xl. $R^2$ is a moiety of the formula

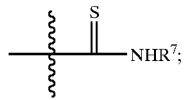

xli. $R^3$ is hydrogen;
xlii. $R^3$ is hydroxy;
xliii. $R^3$ is $C_1$–$C_6$ alkoxy;
xliv. $R^3$ is an amino acid ester,
xlv. $R^3$ is an amino acid;
xlvi. $R^3$ is $NR^4 R^5$;
xlvii. $R^4$ is $C_1$–$C_6$ alkyl;
xlviii. $R^5$ is hydrogen;
xlix. $R^5$ is $C_1$–$C_6$ alkyl;
l. $R^5$ is $C_6$–$C_{10}$ bicycloalkyl;
li. $R^5$ is $(C_1$–$C_4$ alkyl)-phenyl;
lii. $R^5$ is $(C_1$–$C_4$ alkyl)—$CO_2 R^1$;
liii. $R^5$ is $CH_2 CO_2 R^1$;
liv. $R^5$ is aryl;
lv. $R^5$ is substituted aryl;
lvi. $R^5$ is $(CH_2)_n CHR^8 NHC(O)OC(CH_3)_3$;
lvii. $R^5$ is $(CH_2)_n NH_2$;
viii. $R^5$ is $(CH_2)_2 NHCOR^6$;
lix. $R^5$ is $(CH_2)_2 OR^1$;
lx. $R^5$ is $(CH_2)_q$-heterocycle;
lxi. $R^5$ is $(CH_2)_q$-substituted heterocycle;
lxii. $R^4$ and $R^5$, together with the nitrogen to which they are attached, combine to form a pyrrolidin-1-yl, piperidin-1-yl, hexamethyleneimin-1-yl, or morpholin-4-yl ring;
lxiii. n is 1;
lxiv. n is 2;
lxv. n is 3;
lxvi. n is 4;
lxvii. q is 0;
lxviii. q is 1;
lxix. q is 2;
lxx. q is 3;
lxxi. $R^6$ is $C_1$–$C_6$ alkyl;
lxxii. $R^6$ is substituted $C_3$–$C_6$ cycloalkyl;
lxxiii. $R^6$ is aryl;
lxxiv. $R^6$ is substituted aryl;
lxxv. $R^6$ is tert-butoxy;
lxxvi. $R^6$ is $(CH_2)_q$-heterocycle;
lxxvii. $R^6$ is $(CH_2)_q$-substituted heterocycle;
lxxviii. $R^6$ is $(CH_2)_n S(O)_r R^1$;
lxxix. $R^6$ is $C(CH_3)_2 CH_2 N(R^1)_2$;
lxxx. $R^6$ is $(CH_2)_n CHR^8 NHC(O)OC(CH_3)_3$;
lxxxi. $R^6$ is $(CH_2)_n CHR^8 NH_2$;
lxxxii. $R^6$ is $(CH_2)_2 NH$-aryl;
lxxxiii. $R^6$ is $NHR^7$;
lxxxiv. $R^{6'}$ is $C_1$–$C_6$ alkyl;
lxxxv. $R^{6'}$ is substituted $C_3$–$C_6$ cycloalkyl;
lxxxvi. $R^{6'}$ is aryl;
lxxxvii. $R^{6'}$ is substituted aryl;
lxxxviii. $R^{6'}$ is $(CH_2)_q$-heterocycle;
lxxxix. $R^{6'}$ is $(CH_2)_q$-substituted heterocycle;
xc. $R^{6'}$ is $(CH_2)_n S(O)_r R^1$;
xci. $R^{6'}$ is $C(CH_3)_2 CH_2 N(R^1)_2$;
xcii. $R^{6'}$ is $(CH_2)_n CHR^8 NH$—$C(O)OC(CH_3)_3$;
xciii. $R^{6'}$ is $(CH_2)_n CHR^8 NH_2$;
xciv. $R^{6'}$ is $(CH_2)_2 NH$-aryl;
xcv. r is 0;
xcvi. r is 1;
xcvii. r is 2;
xcviii. $R^7$ is $C_1$–$C_6$ alkyl;
xcix. $R^7$ is phenyl;
c. $R^7$ is substituted phenyl;
ci. $R^8$ is hydrogen;
cii. $R^8$ is $CO_2 R^1$;
ciii. $R^9$ is $CO_2 R^1$;
civ. $R^9$ is aryl;
cv. $R^9$ is substituted aryl;
cvi. $R^9$ is thiophene;
cvii. $R^9$ is $C_1$–$C_4$ alkoxy;
cviii. $R^9$ is $(C_1$–$C_3$ alkyl)-phenyl;
cix. $R^9$ is $C_2$–$C_6$ alkenyl;
cx. $R^{10}$ is halo;
cxi. $R^{10}$ is $CO_2 R^1$;
cxii. $R^{10}$ is aryl;
cxiii. $R^{10}$ is substituted aryl;
cxiv. $R^{10}$ is, thiophene;
cxv. $R^{10}$ is $C_1$–$C_4$ alkoxy;
cxvi. $R^{10}$ is $(C_1$–$C_3$ alkyl)-phenyl;
cxvii. $R^{10}$ is $C_2$–$C_6$ alkenyl;
cxviii. $R^{11}$ is hydrogen;
cxix. $R^{11}$ is $CO_2 R^1$;

cxx. $R^{11}$ is aryl;

cxxi. $R^{11}$ is substituted aryl;

cxxii. $R^{11}$ is thiophene;

cxxiii. $R^{11}$ is $C_1$–$C_4$ alkoxy;

cxxiv. $R^{11}$ is ($C_1$–$C_3$ alkyl)-phenyl;

cxxv. $R^{11}$ is $C_2$–$C_6$ alkenyl;

cxxvi. $R^{12}$ is $C_1$–$C_6$ alkyl;

cxxvii. $R^{12}$ is ($C_1$–$C_4$ alkyl)-phenyl;

cxxviii. $R^{12}$ is aryl;

cxxix. $R^{12}$ is substituted aryl;

cxxx. $R^{12}$ is heterocycle;

cxxxi. $R^{12}$ is substituted heterocycle;

cxxxii. Het is

[isoxazole structure with $R^b$]

cxxxiii. Het is

[isoxazole structure with $R^b$]

cxxxiv. Het is

[isothiazole structure with $R^b$]

cxxxv. Het is

[isothiazole structure with $R^b$]

cxxxvi. Het is

[pyrazole structure with $R^a$ and $R^b$]

cxxxvii. Het is

[imidazole structure with $R^a$ and $R^b$]

cxxxviii. Het is

[oxazole structure with $R^b$]

cxxxix. $R^b$ is $C_1$–$C_6$ alkyl;

cxl. $R^b$ is aryl;

cxli. $R^b$ is halo;

cxlii. $R^b$ is —$SR^{12}$;

cxliii. $R^b$ is optionally substituted heterocycle;

cxliv. $R^b$ is —$NR^4R^5$;

cxlv. $R^a$ is t-butyl;

cxlvi. The compound is a pharmaceutical salt; and cxlvii. The compound is the hydrochloride salt.

The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I(a), wherein $R^b$, the substituent from the non-fused carbon, is $C_1$–$C_6$ alkyl, optionally substituted aryl, $CH_2OH$, or $CH_2O$-heterocycle may be prepared from compounds of formula II(a) as illustrated in Scheme 1 below where R, R', $R^9$, $R^{10}$, $R^{11}$, het and m are as described supra.

Scheme 1

[Structure of formula II(a)]

-continued

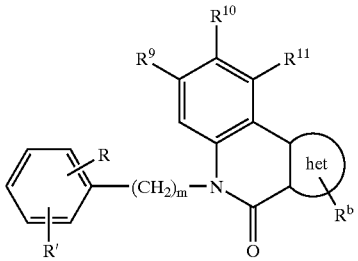

I(a)

$R^b$ is $C_1$—$C_2$ alkyl,
   optionally substituted aryl,
   $CH_2OH$,
   or $CH_2O$-heterocycle.

Compounds of formula I(a) may be prepared by dissolving or suspending a compound of formula II(a) in a suitable solvent, preferably dimethylformamide, and adding a suitable base, including potassium methoxide, potassium tert-butoxide and preferably potassium carbonate. The base is typically employed in a large molar excess, usually in about a 4 to about an 8 molar excess relative to the compound of formula II(a). Preferably, about a 5 to about a 7 molar excess is employed.

The reactants are typically combined at a temperature from about 0° C. to about 100° C. When het is isoxazole, oxazole, or imidazole, the reactants are preferably combined at room temperature and the resulting solution is typically heated from about 30° C. to about the reflux temperature of the mixture for from 30 minutes to about 18 hours. Preferably, the mixture is heated to at least 50° C. for from about 1 to about 6 hours, and is most preferably heated to from about 65° C. to about 75° C. for from about 1.5 hours to about 3 hours. When het is pyrazole the reactants are preferably combined at room temperature and the resulting solution is typically heated to about 100° C. for from 30 minutes to about 18 hours.

Any protecting groups remaining in the cyclized compound of formula I may be removed as taught in Greene to provide the compounds of formula I. Preferred choices of protecting groups and methods for their removal may be found in the Preparations and Examples sections below.

Compounds of formula I(b), wherein het is substituted with halo may be prepared from compounds of formula II(b) as illustrated in Scheme 2 below where R, R', $R^9$, $R^{10}$, $R^{11}$, het and m are as described supra.

Scheme 2

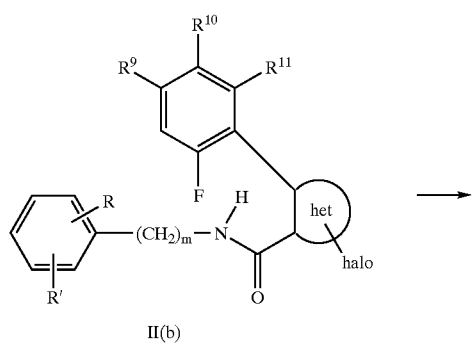

II(b)

-continued

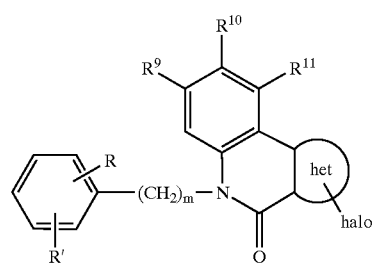

I(b)

Compounds of formula I(b) may be prepared by dissolving or suspending a compound of formula I(b) in a suitable solvent and adding a suitable base, in an inert atmosphere, preferably under $N_2$. Typically a preferred and convenient solvent is dimethylformamide. A preferred base is sodium trimethylsilanolate. The base is typically employed in a slight molar excess, usually in about a 1.05 molar excess relative to the compound of formula II(b). The reactants are typically combined dropwise at room temperature over a period of time from about 2 hours to about 4 hours.

The skilled artisan would appreciate that if other bases are used in the reaction of Scheme 2, the substituent of the het functionality may change. For example if sodium methylthiolate is used as the preferred base, the compound of formula II(b) will be converted into the compound of formula I wherein the het functionality is substituted with —$SCH_3$.

Additionally, the compound of formula I(b) can be prepared according to Scheme 1 wherein the reactants are combined at 0° C. and mixed at −10° C. for approximately three hours. The solution is then warmed to room temperature and mixed for an additional 2 to 3 hours.

Certain compounds of formula I(a) are useful MRP1 inhibitors and are also useful intermediates for the preparation of other compounds of formula I. As is shown in Scheme 3, when $R^b$ of formula I(a) is $CH_2O$-Pg, wherein "Pg" is a protecting group, the compound of formula I(a) may be further reacted by methods known in the art to produce compounds of formula I(c) where $R^b$ is $CH_2OH$, $CH_2N_3$, $CH_2SR^1$, or $CH_2NR^4R^5$, and R, R', $R^1$, $R^4$, $R^5$, $R^9$, $R^{10}$, $R^{11}$, het, and m are as defined above.

Scheme 3

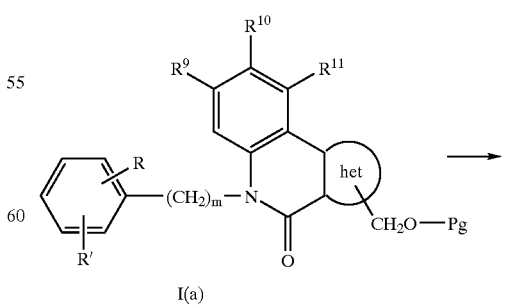

I(a)

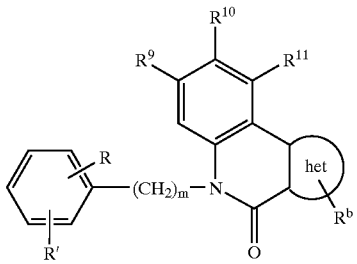

I(c)

R$^b$ is CH$_2$OH,
CH$_2$N$_3$,
CH$_2$SR$^1$,
or CH$_2$NR$^4$R$^5$.

Compounds of formula I(c) wherein het is substituted with CH$_2$OH may be prepared by dissolving or suspending a compound of formula I(a) in a suitable solvent and adding a suitable acid. Typically a preferred and convenient solvent is methanol/dichloromethane (2:1). A preferred acid is p-toluenesulfonic acid hydrate. The acid is typically employed in a slight molar excess, usually in about a 1.05 molar excess relative to the compound of formula I(a). The reactants are typically combined at room temperature and mixed from about 1 hour to about 3 hours.

The skilled artisan would appreciate that the alcohol can be further converted to compounds of formula I(c) where het is substituted with CH$_2$N$_3$, CH$_2$SR$^1$, or CH$_2$NR$^4$R$^5$ by methods well known in the art. For general examples of these procedures, see the Preparations and Example section.

Compounds of formula I(b) when het is substituted with chloro are useful MRP1 inhibitors and are also useful intermediates for the preparation of other compounds of formula I. As is shown in Scheme 4, the compound of formula I(b) may be further reacted with a nucleophile by methods known in the art to produce compounds of formula I(d) where het is substituted with an amino acid ester, OR$^1$, SR$^{12}$, S(CH$_2$)$_n$-phenyl, NR$^4$R$^5$, or an optionally substituted heterocycle attached via a heteroatom and R, R', R$^9$, R$^{10}$, R$^{11}$, R$^1$, R$^{12}$, n, het and m are as defined above.

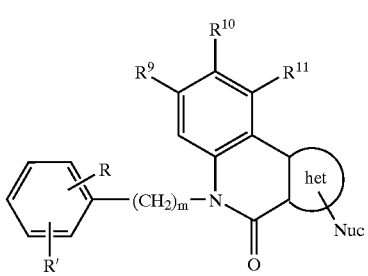

I(o)

Compounds of formula I(o) may be prepared by dissolving or suspending a compound of formula I(b) in a suitable solvent and adding an appropriate nucleophile, in an inert atmosphere, preferably under N$_2$. Typically a preferred and convenient solvent is dimethylformamide. The nucleophile is typically employed in a molar excess, usually in about a 2 to about a 4 molar excess relative to the compound of formula I(b).

The reactants are preferably combined at room temperature and the resulting solution is typically mixed for from about 30 minutes to about 3 hours, until the reaction is complete as measure by the consumption of the compound of formula I(b). The skilled artisan would appreciate that the reaction, depending on the nucleophile used, may require more time to react and may, also require heating. In these instances, it is preferred to mix the reactants for from approximately 15 to approximately 20 hours, then heat the solution to from about 50° C. to about 80° C. and mix for an additional 3 hours or until the reaction is complete as measure by the consumption of the compound of formula I(b).

Compounds of formula I where R is (CH$_2$)$_m$·CHR$^1$NR$^4$R$^5$ may be prepared from compounds of formula I(n) as illustrated in Scheme 5 below where m, m', R', R$^a$, R$^b$, R$^1$, R$^4$, R$^5$, R$^9$, R$^{10}$, and R$^{11}$ are as described supra.

Scheme 4

Scheme 5

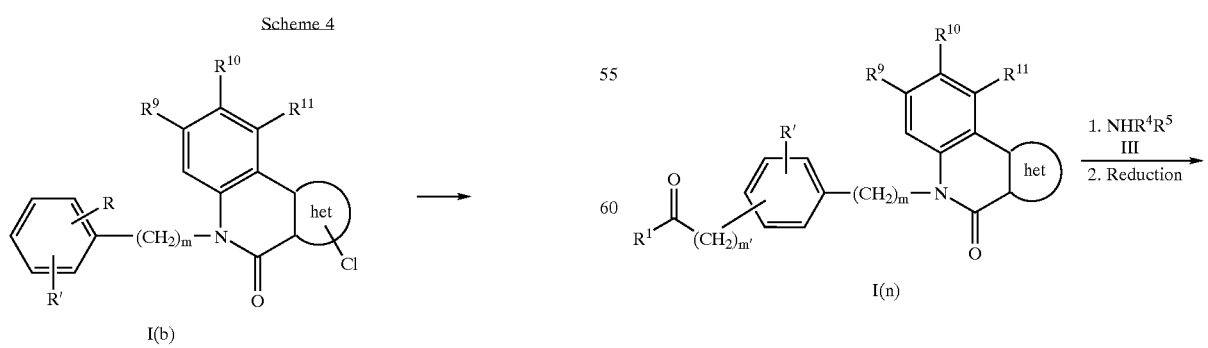

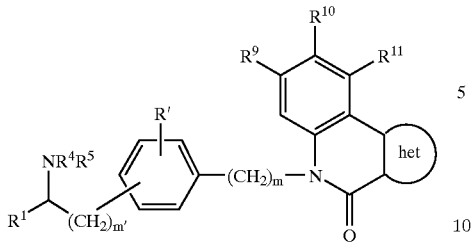

I(e)

The compounds of formula I(n) may be reductively aminated to form the compounds of formula I(e). Reductive aminations are well known transformations, see, e.g., Larock, "Comprehensive Organic Transformations", pg. 421, VCH Publishers, New York, N.Y., 1989, hereafter referred to as "Larock".

Amines of formula III may be dissolved or suspended in a suitable solvent, optionally in the presence of a suitable base, preferably N-methyl morpholine or triethylamine, when the compound of formula III is an acid addition salt to convert the salt to its free amine form, and a compound of formula I(n) is added. A Lewis acid catalyst, such as titanium(IV) isopropoxide, may optionally be employed. Once it is determined that the compound of formula I(d) has been substantially consumed, the intermediate is typically reacted in situ with a suitable reducing agent to provide the compounds of formula I(e). The overall conversion may be performed at about 0° C. to the boiling point of the mixture, but room temperature is a preferred reaction temperature. The formation of the compounds of formula I(e) may take from 15 minutes to 24 hours as measure by the consumption of the compound of formula I(d). Methanol is typically a preferred solvent.

Suitable reducing agents include, but are not limited to, hydrogen over palladium or platinum on carbon, borane or complexes of borane, e.g., borane-pyridine, borane-t-butylamine, and borane-dimethylamine complex; and borohydride reducing agents such as sodium borohydride or sodium cyanoborohydride. Sodium cyanoborohydride is a preferred reducing agent.

Compounds of formula I where R is $(CH_2)_m CHR^1 NHR^2$ or $O(CH_2)_2 NHR^2$ and $R^2$ is $CH_2 R^{6'}$ may be prepared from compounds of formula I(f) and I(h) as illustrated in Scheme 6 below where X is halide and m, m', R', $R^a$, $R^b$, $R^1$, $R^{6'}$, $R^9$, $R^{10}$, and $R^{11}$ are as described supra.

Scheme 6

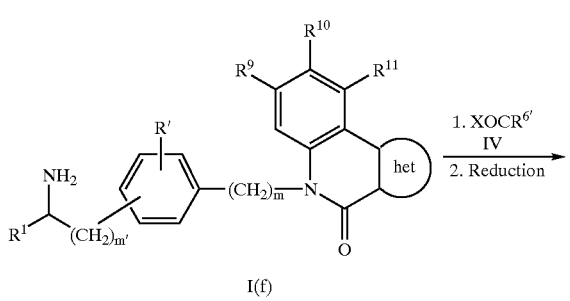

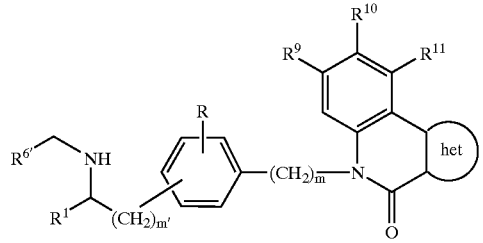

I(g)

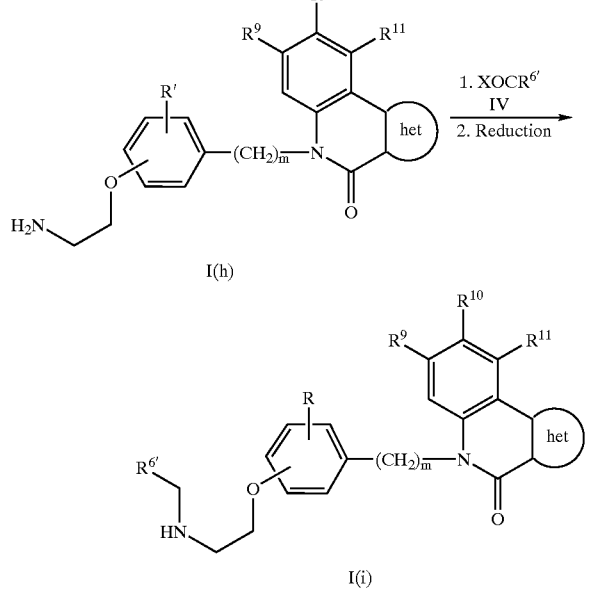

The compounds of formulas I(f) and I(h) may be reductively alkylated to form the corresponding compounds of formulas I(g) and I(i), respectively. Reductive alkylation of primary amines are well known transformations, see, e.g., Larock, pg. 434–435.

The skilled artisan will appreciate that the treatment of acyl halides with amines is a very general reaction for the preparation of amides, see, e.g. March J, *Advanced Organic Chemistry*, 1985, 3rd edition, page 370. The reaction is highly exothermic and must be carefully controlled, usually by cooling.

Once it is determined that the compound of formula IV has been substantially consumed, the intermediate is typically reacted in situ with a suitable reducing agent to provide the compounds of formula I(g) and I(i), respectively. The overall conversion may be performed at about 0° C. to the boiling point of the mixture but room temperature is a preferred reaction temperature. The formation of the compounds of formulas I(g) and I(i) may take from 15 minutes to 24 hours as measure by the consumption of the compound of formula IV.

A base is typically employed when the compound of formula I(f) or I(h) is an acid addition salt in order to convert the salt to its free amine form. Preferred bases for this purpose are N-methylmorpholine and triethylamine. A preferred lewis acid catalyst is titanium(IV) isopropoxide. Suitable reducing agents include, but are not limited to, borane or complexes of borane, e.g., borane-pyridine, borane-t-butylamine, and borane-dimethylamine complex; and lithium aluminum hydride.

The skilled artisan would appreciate that the compounds of formulas I(f) and I(h) may be converted to the corresponding compounds of formulas I(g) and I(i), respectively, by reacting with ketones and aldehydes as is represented in Scheme 5. Reductive alkylation of primary amines are well known transformations, see, e.g., Larock, supra.

Compounds of formula I(h) may be converted to other compounds of the invention by methods well known in the chemical arts. Compounds of formula I where R is $O(CH_2)_2NHR^2$, and $R^2$ is $CONHR^7$ or a moiety of the formula

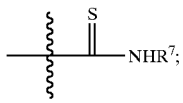

and m, R', $R^7$, $R^9$, $R^{10}$, and $R^{11}$ are prepared as described supra.

Scheme 7

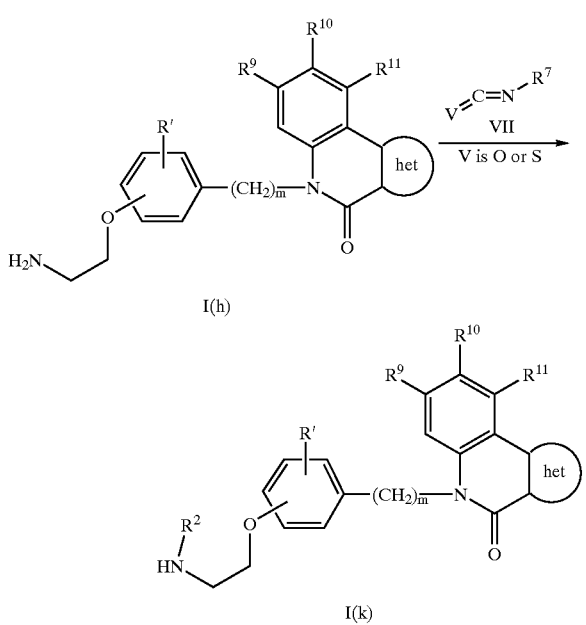

The primary amines of formula I(h) may be reacted with the isocyanates or isothiocyantes of formula VII to prepare the corresponding ureas and thioureas of formula I(k), see March, pages 802–803.

Compounds of formula I where R is $(CH_2)_{m'}CHR^1NHR^2$, and $R^2$ is $SO_2R^7$; and m, m', R', $R^1$, $R^7$, $R^9$, $R^{10}$, and $R^{11}$ are prepared as described supra.

Scheme 8

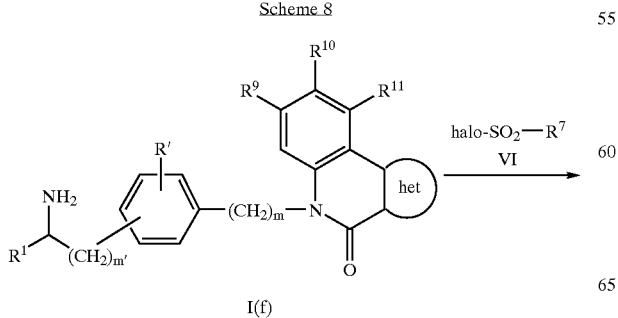

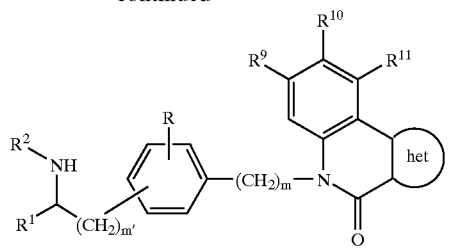

I(j)

Compounds of formula I(f) may be converted to other compounds of the invention via standard combinatorial synthetic techniques. For example, a compound of formula I(f) dissolved or suspended in a suitable solvent, optionally in the presence of a base, may be treated with a compound of formula VI to provide a compound of formula I(j) where $R^2$ is $SO_2R^7$. Typically a preferred and convenient solvent is dichloromethane. When a base is employed, triethylamine is typically preferred. Furthermore, when a base is employed, the base and compound of formula VI are typically employed in a slight stoichiometric excess. For example a 1.01 to 1.40 molar excess, relative to the compound of formula I(f), is generally employed. About 1.15 to about 1.25 molar excess is typically preferred. When a base is not employed, the compound of formula VI is typically employed in a relatively larger stoichiometric excess. For example, about a 1.5 to about a 3 molar excess, relative to the compound of formula I(f), is usually employed. About 1.8 to about 2.2 molar excess is typically preferred. The reaction is usually performed at a temperature range of about 0° C. to about the reflux temperature of the solvent for from 10 minutes to 18 hours. Preferably, the reaction is performed at about 15° C. to about 40° C. for from 5 minutes to about 1 hour.

Compounds of formula I where R is $(CH_2)_{m'}COR^3$ and $R^3$ is $C_1-C_6$ alkoxy, an amino acid ester, or $NR^4R^5$ may be prepared from compounds of formula I(i) as illustrated in Scheme 9 below where $R^{14}$ is $NR^4R^5$, an amino acid ester, or $C_1-C_6$ alkoxy, $R^{13}$ is an activating group, and m, m', R', $R^a$, $R^b$, $R^4$, $R^5$, $R^9$, $R^{10}$, and $R^{11}$ are as described supra.

Scheme 9

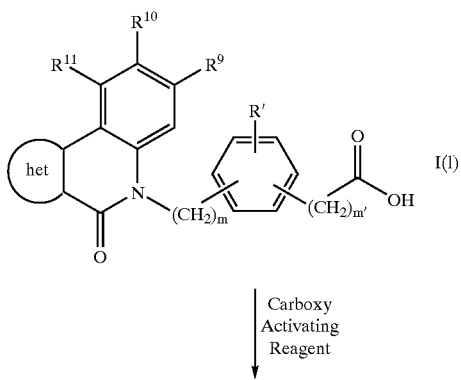

Carboxy Activating Reagent

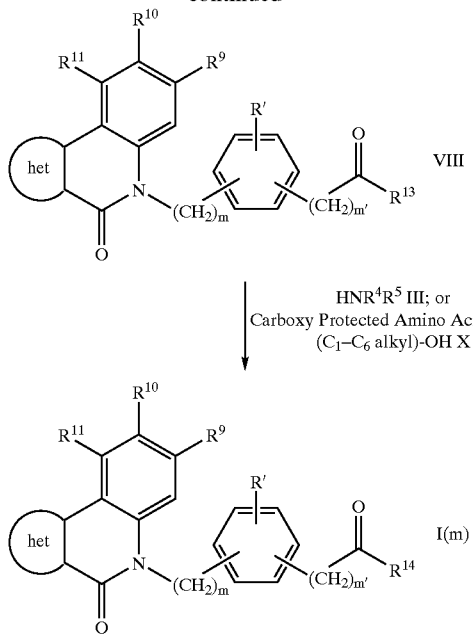

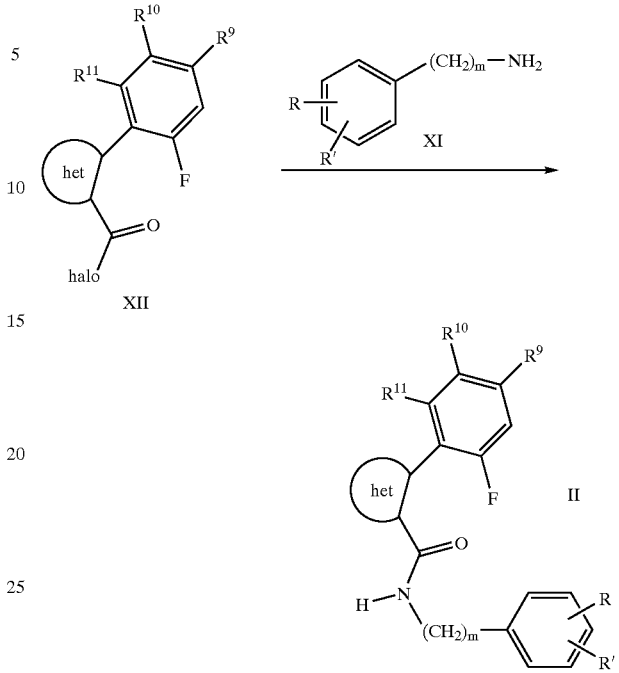

Compounds of formula I(l), prepared as described in Scheme 1, may also be converted to other compounds of the invention via solution or solid phase synthetic techniques. For example, acids of formula I(l) may be treated with activating agents to form the activated carboxylic acid derivatives of formula VIII by methods well known in the chemical arts. See, e.g., The Peptides, Peptide Synthesis and the Examples and Preparations sections below.

Generally, preparation of compounds of formula I(m) where $R^{14}$ is $NR^4R^5$ or an amino acid ester is performed in a manner similar to the reaction of compounds of formula I(f) or I(h) described in Scheme 6. Specifically, such compounds of formula I(m) may be prepared by dissolving or suspending a compound of formula VIII in a suitable solvent, optionally in the presence of a suitable base, and adding an amine of formula III or IX. Typically a preferred and convenient solvent is dichloromethane. Preferred bases are triethylamine and piperidinylmethylpolystyrene resin. The amine is typically employed in a molar excess. For example, about a 1.5 to about a 3 molar excess, relative to the compound of formula VIII is usually employed. About 1.8 to about 2.2 molar excess is typically preferred. The reaction is usually performed in a temperature range of about 0° C. to about the reflux temperature of the solvent for from 10 minutes to 18 hours. Preferably, the reaction is performed at about 15° C. to about 40° C. for from 5 minutes to about 2.5 hours.

The compounds of formula I(m) where $R^{14}$ is $C_1$–$C_6$ alkoxy may be prepared by methods very well known in the chemical arts. For instruction on the conversion of activated carboxylic acid derivatives to esters see, e.g., Larock at 978–979. Alternatively, these compounds of formula I(m) may be prepared directly from the acids of formula I(l) as taught in the Larock reference at pages 966–972.

The starting materials and compounds of the present invention may be obtained by a number of routes. For example, compounds of formula II may be prepared according to the routes shown in Schemes 8 and 9.

Where het, $R^a$, $R^b$, R, R', $R^9$, $R^{10}$, and $R^{11}$, and m are as described supra, compounds of formula II may be prepared according to Scheme 10.

Compounds of formula II may be prepared by dissolving or suspending a compound of formula XII in a suitable solvent and adding a compound of formula XI in a suitable solvent. Dimethylformamide is a convenient solvent and is typically preferred for the compound of formula XII. A 1:1 mixture of DMF and dichloromethane is a convenient solvent and is typically preferred for the amine of formula XI. This amide forming reaction is also preferably run in the presence of dimethylaminopyridine (DMAP).

For compounds in which het is pyrazole, the addition of 1-(3-dimethyl-aminopropyl)-3-ethylcarbodiimide hydrochloride (EDCI) to the reaction is preferred. The compound of formula XII is preferably the corresponding carboxylic acid and is employed in an equimolar amount, relative to the compound of formula XI, but a slight excess (about a 0.05 to about 0.15 molar excess) is acceptable. The DMAP is employed in a catalytic fashion. For example, about 5 molar percent to about 15 molar percent, relative to the compound of formula XI, is typically employed. A 10 molar percent is usually preferred.

Compounds of formula XI where R is $(CH_2)_{m'}COR^1$, $(CH_2)_{m'}NH$-Pg, $O(CH_2)_2NH$-Pg, or $(CH_2)_{m'}CO_2(C_1$–$C_6$ alkyl) which are used to prepare compounds of formula I(d), I(f), I(h), and I(l) respectively, are well known in the art and to the extent not commercially available, are readily synthesized by standard procedures commonly employed in the art. Furthermore, the transformations described in Schemes 3–8 may be performed before the cyclization described in Scheme 1 and 2 to provide the compounds of formula XI with a fully elaborated R substituent.

Additionally, compounds of formula XII may be prepared according to the following routes where, unless otherwise provided, $R^b$ is the substituent from the carbon atom of het, $R^a$ is the substituent from the saturated nitrogen of het, the second heteroatom is an oxygen or sulfur (represented by O in the following routes) and other variables are as described supra.

Compounds of formula XI(a) may be prepared in a manner similar to that described in the literature, for example, see Chen Y P, et. al, Heterocycles, 1995, 41, 175, and Chantegrel B, et. al, *J. Org. Chem.*, 1984, 49, 4419–4424.

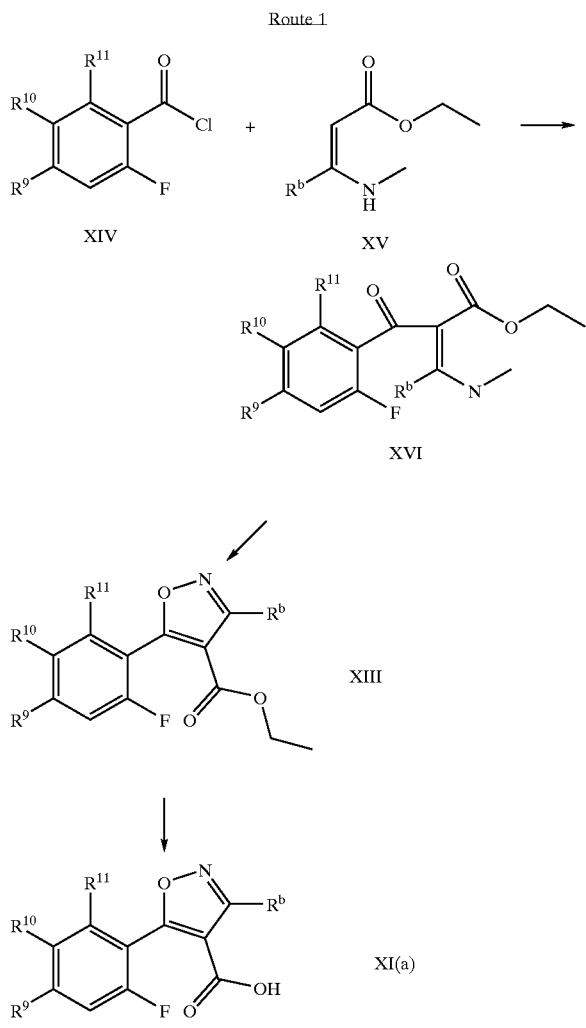

Compounds of formula XVI may be prepared by dissolving or suspending a compound of formula XV and a suitable base in a suitable solvent and adding a compound of formula XIV in a suitable solvent, dropwise. Toluene is a convenient solvent and is typically preferred. Triethylamine is the preferred base. The compound of formula XIV is typically and preferably employed in an equimolar amount, relative to the compound of formula XV, but a slight excess is acceptable.

The reactants are preferably combined at about 0° C. and the resulting solution is typically warmed to room temperature and mixed for from about 18 hours to about 24 hours.

The compound of formula XVI may then be converted to the compound of formula XIII by dissolving or suspending a compound of formula XVI in a suitable acidic solvent and adding hydroxylamine hydrochloride. Glacial acetic acid is a convenient acidic solvent and is typically preferred. The ester group is then hydrolyzed to the corresponding carboxylic acid of formula XI(a) through standard procedures commonly employed in the art.

The reactants are preferably combined at about room temperature then heated to reflux for from about 30 minutes to about 60 minutes. Preferably the reaction is heated to reflux from about 40 to 45 minutes.

The ester group of the compounds of formula XIII is then hydrolyzed to the corresponding carboxylic acid through standard procedures commonly employed in the art, see for example, Larock, pgs 981–985.

Compounds of formula XIV and XV are known in the art and, to the extent not commercially available, are readily synthesized by standard procedures commonly employed in the art.

Compounds of formula XIX may be prepared in a manner similar to that described in the literature, for example, see Liu K, Shelton B R, Howe, R K, *J. Org. Chem.*, 1980, 45, 3916–3918.

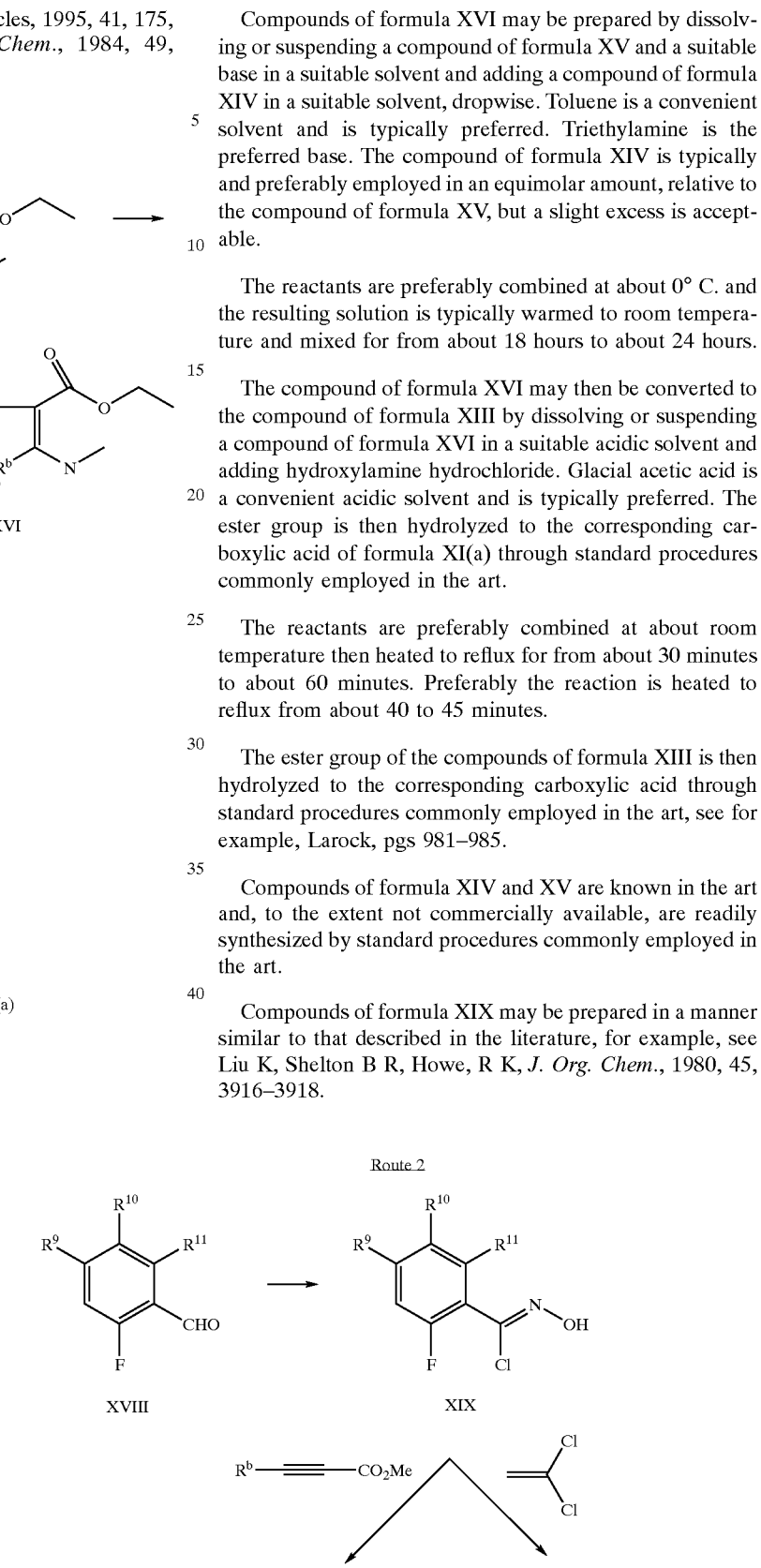

-continued

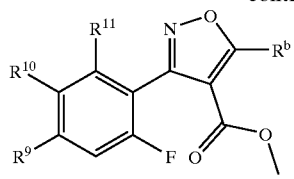

XX

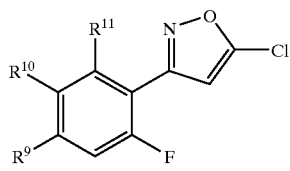

XXI

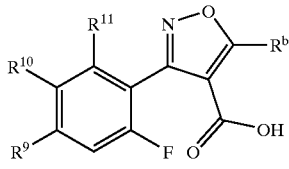

XI(b)

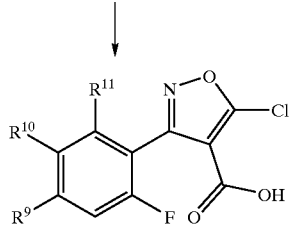

XI(c)

Generically, the compound of formula XVIII and hydroxylamine hydrochloride are suspended or dissolved in a suitable solvent and a suitable base is added. After the reaction is complete, the solution is acidified with a suitable acid and the resulting oxime is purified by known methods. Typically a preferred and convenient solvent is water/methanol. Typically a preferred and convenient base is sodium hydroxide.

The reactants are preferably combined at about 0° C. and the resulting solution is typically mixed for about 1 hour at about 25–30° C., until the reaction is complete. After the reaction is complete, the solution is acidified with a suitable acid, preferably hydrochloric acid, and the resulting oxime is purified by known methods.

The purified oxime is dissolved or suspended in a suitable solvent, preferably DMF, and is then reacted with N-chlorosuccinimide (NCS). Preferably, NCS is added in small portions to control the expected exotherm. The initial NCS addition results in a slight temperature decrease. If the reaction does not self-initiate within about 10 minutes, as indicated by a slight temperature rise, hydrogen chloride may be bubbled into the DMF solution. If the reaction does not begin within about 10 to 15 minutes, heating the solution to about 45–60° C. is desirable. Once the reaction begins, the temperature is preferably maintained below about 35° C. for benzaldoximes with electron-donating substituents and below about 50° C. for strong electron-withdrawing substituents. Completion of the reaction is indicated by cessation of the exotherm.

The compound of formula XIX is then converted to the compound of formula XX by methods well known to the skilled artisan. The compound of formula XIX and an appropriate methyl-2-butynoate are dissolved or suspended in a suitable solvent, preferably ethyl ether, and $Et_3N$ is added. The reactants are combined at about room temperature and mixed from about 12 to 24 hours, until the reaction is complete.

The ester group of the compounds of formula XX is then hydrolyzed to the corresponding carboxylic acid of formula XI(b) through standard procedures commonly employed in the art, see for example, Larock, pgs 981–985.

Compounds of formula XXI may be prepared in a manner similar to that described in the literature, for example, see Stevens R L, Albizati K F, *Tetrahedron Lett*. 1984, 25, 4587. For an example of this transformation, see Preparation 3.

Compounds of formula XI(c) may be prepared from compounds of formula XXI in a manner similar to that described in the literature, for example, see Micetich R G, Chin C G, *Can. J. Chem*. 1970,48, 1371. For an example of this transformation, see Preparation 4.

Compounds of formula XVIII are known in the art and, to the extent not commercially available, are readily synthesized by standard procedures commonly employed in the art.

The isoxazole compounds of formula XI may be converted to the isothiazole by methods well known in the art, for example see McGregor D N, Corbin U, Swigor J E, and Cheney L C, "Synthesis of isothiazoles: The transformation of isoxazoles into isothiazoles," *Tetrahedron*, 1969, 25, 389–395.

Compounds of formula I where het is pyrazolyl may be prepared as illustrated below.

Route 3

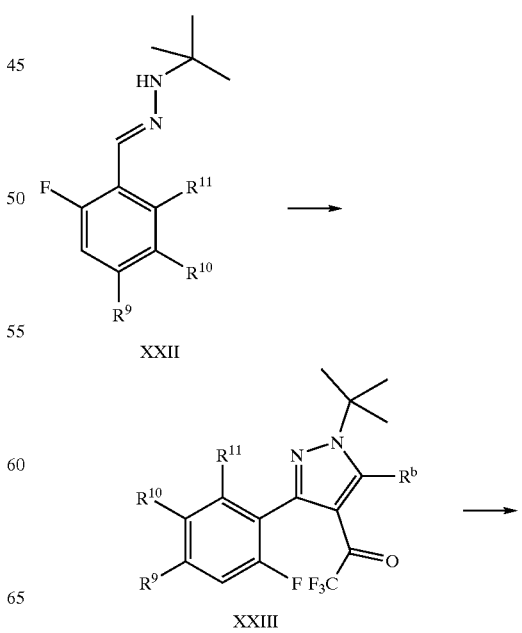

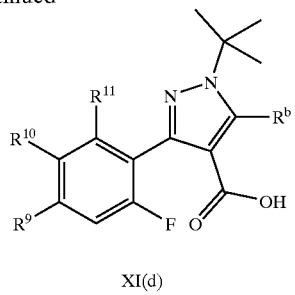

XI(d)

Compounds of formula XXIII may be prepared by combining the compound of formula XXII with ethyl trifluoroacetyl vinyl ether in a manner similar to that described in the literature, for example, see Kamitori et al, *J. Met. Chem.*, 1993, 30, 389. For examples of this transformation, see Preparations 7–8.

Additionally, compounds of formula XXIII may be prepared from aldehyde hydrazones and ethyl propiolate as is further described by Kamitori et al, *Heterocycles*, 1994, 38, 21.

The trifluoromethyl ketone of formula XXIII may be converted to the corresponding carboxylic acid of formula XI(d) in a manner similar to that described in the literature, for example, see Delgado A, Clardy J, *Tetrahedron Lett.* 1992, 33, 2789–2790.

Compounds of formula XXII are known in the art and, to the extent not commercially available, are readily synthesized by standard procedures commonly employed in the art.

Compounds of the invention where het is oxazolyl or imidazolyl may be prepared as illustrated below.

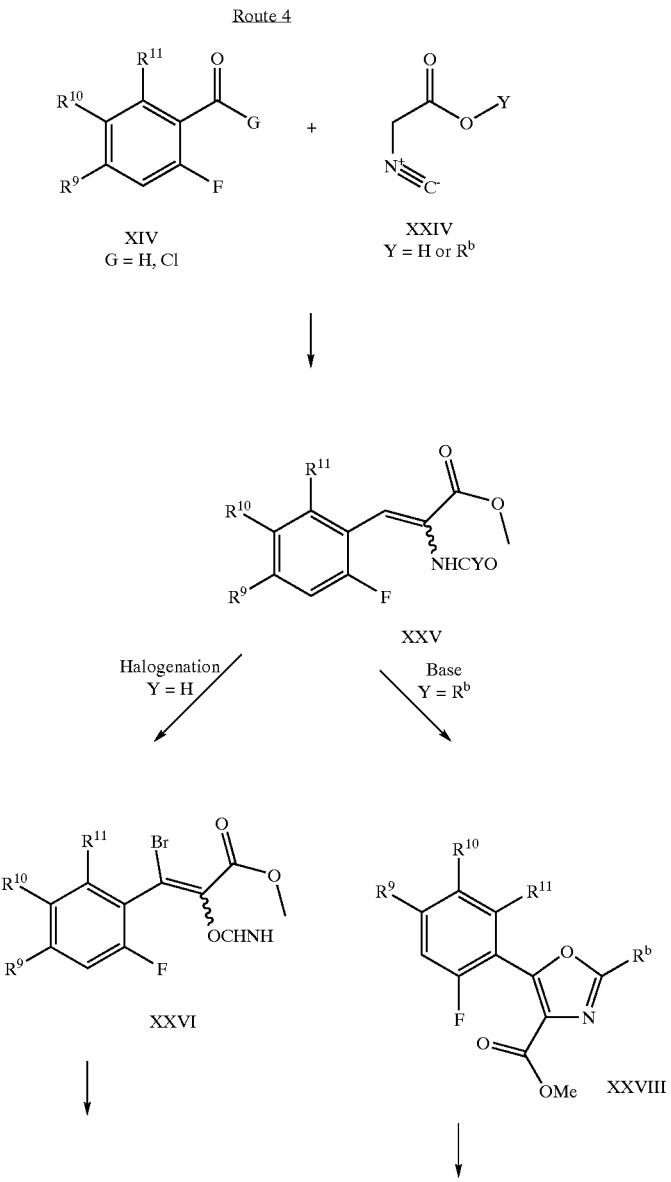

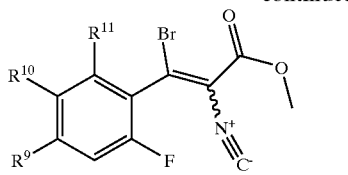

XXVII

1) R$^a$—CH$_2$—NH$_2$
2) Hydrolyze

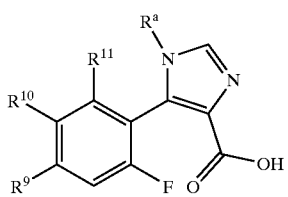    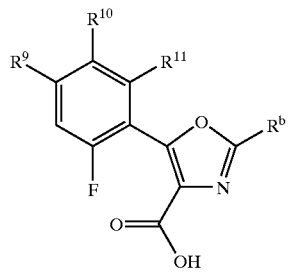

XI(e)                  XI(f)

Compounds of formula XI(e) may be prepared in a manner similar to that described in the literature, for example, see Nunami et al, *J. Org. Chem.* 1994, 59, 7635–7642.

The compound of formula XXV is converted to the compound of formula XXVIII by methods well known to the skilled artisan. The compound of formula XXV is dissolved or suspended in a suitable solvent, preferably tetrahydrofuran, and a base is added, preferably Et$_3$N. The reactants are combined at about room temperature, preferably under an inert atmosphere, and mixed from about 30 minutes to 2 hours, until the reaction is complete.

The ester group of the compounds of formula XXVIII is then hydrolyzed to the corresponding carboxylic acid formula XI(f) through standard procedures commonly employed in the art, see for example, Larock, pgs 981–985.

Compounds of formula XIV and XXV are known in the art and, to the extent not commercially available, are readily synthesized by standard procedures commonly employed in the art.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tataric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The optimal time for performing the reactions of Schemes 1–8 and Routes 1–5 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example "° C.", "N", "mmol", "go", "mL", "M", "HPLC", "IR", "MS (FD)", "MS (IS)", "MS (FIA)", "MS (FAB)", "MS (EI)", "MS (ES)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, electron spray mass spectrometry, ultraviolet spectrometry, and proton nuclear magnetic resonance spectrometry respectively. In addition, the absorption maxima listed for the IR spectra are only those of interest and not all of the maxima observed.

PREPARATIONS

Preparation 1

2-Chloro-5-fluorobenzaldehyde Oxime

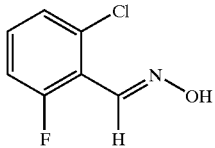

To a mixture of 2-chloro-6-fluorobenzaldehyde (20 g, 0.126 mmoL) in water (30 mL), ethanol (35 mL) and ice (55 g) were added to hydroxylamine hydrochloride (9.64 g, 0.139 mmoL), then NaOH (12.6 g) in water (30 mL) was added with stirring. Enough ice was added to maintain temperature at 25–30° C. After 1 h, the mixture was washed with ether (150 mL) and acidified with concentrated HCl to a pH of 6 (ice was added to keep the temperature at 25–30° C.). The product was extracted with dichloromethane (2×200 mL), dried over MgSO$_4$ and the solvent removed in vacuo to furnish the oxime as a white solid (17.2 g, 79.0%). mp 132.8–134.0° C.

$^1$H NMR (DMSO-d$_6$, 300 MHz) δ; 11.83 (s, 1H, OH), 8.19 (s, 1H, C:CH), 7.26–7.39 (m, 3H)ppm. IR (CHCl$_3$) υ$_{max}$ 3573, 3311, 1603, 1570, 1461, 1449, 1252, 986, 964, 907, 845 cm$^{-1}$. UV (EtOH) λ$_{max}$ 249 (ε=11551)nm. MS (ES) m/z 174.1 [(M+1)$^+$, 100]. Anal. Calcd. for C$_7$H$_5$NOClF; Theoretical: C, 48.44; H, 2.90; N, 8.07, Cl, 20.43; Found: C, 48.46; H, 2.91; N, 8.14, Cl, 20.18%.

Preparation 2

2-Chloro-5-fluorobenzoylchloride Oxime

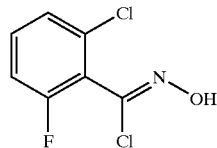

To a solution of alcohol (2 g, 11.53 mmoL) in DMF (20 mL) was added N-chlorosuccinimide (NCS) (300 mg, 2.24 mmoL) at room temperature. After 10 minutes, bubbled 10 mL HCl gas by syringe. When reaction started, cooled at −50° C. Slowly added rest of NCS (1.55 g, 11.61 mmoL). After two hours, the reaction mixture was poured into four volumes (80 mL) of ice water and extracted with ether (50 mL×2). The combined ether extracts were washed with water (20 mL×2), dried, concentrated to give the product as an oil (2.35 g, 98%). Because this compound was unstable, next reaction was carried out immediately.

$^1$H NMR (CDCl$_3$, 300 MHz) δ; 8.31 (s, 1H, OH), 7.37 (m, 1H), 7.27 (d, J=7.7 Hz, 1H), 7.12 (t, 1H)ppm. IR (CHCl$_3$) υ$_{max}$ 3554, 3279, 1629, 1600, 1575, 1452, 1257, 1230, 1180, 993, 939, 898 cm$^{-1}$. UV (EtOH) λ$_{max}$ 295 (ε=1359), 260 (ε=9105), 213 (ε=18662)nm.

Preparation 3

5-Chloro-3-(2-chloro-6-fluorophenyl)isoxazole

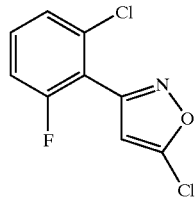

A mixture of triethyl amine (44 mL) in DMF (50 mL) and vinylidene chloride (30 mL) was slowly added to a solution of methanol (26 g, 125 mmoL) in vinylidene chloride (100 mL) and DMF (100 mL) at room temperature under argon. After 15 h, the reaction mixture was poured into ether (700 mL) and washed with water (250 mL×3), dried, and concentrated in vacuo to give crude product, which was purified by flash chromatography (gradient: 0–20% ethyl acetate/hexanes) to produced an oil as a product (23.3 g, 80.3%)

$^1$H NMR (CDCl$_3$, 300 MHz) δ; 7.31–7.44 (m, 2H), 7.13 (t, 1H), 6.40 (s, 1H)ppm. $^{13}$C NMR (DMSO-d$_6$) δ 162.6 (C), 158.6 (C), 157.5 (C), 154.8 (C), 143.6 (C), 131.7 (CH), 125.8 (CH), 114.5 (CH), 103.2 (CH)ppm. IR (CHCl$_3$) υ$_{max}$ 1612, 1560, 1454, 1392, 1253, 900 cm$^{-1}$. UV (EtOH) λ$_{max}$ 275 (ε=1103)nm. MS (FIA) m/z 232.1 (M$^+$, 100). Anal. Calcd. for C$_9$H$_4$NOCl$_2$F; Theoretical: C, 46.59; H, 1.74; N, 6.04; Cl, 30.56; Found: C, 46.45; H, 1.94; N, 6.15; Cl, 30.40%.

Preparation 4

4-Carboxy-5-chloro-3-(2-chloro-6-fluorophenyl)isoxazole

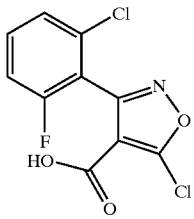

Butyllithium (43.2 mL, 68.4 mmoL) was slowly added to a solution of chloroisoxazolic acid (13.8 g, 59.5 mmoL) in THF (250 mL) at −78° C. The mixture was stirred for 30 minutes and carbon dioxide gas was bubbled through the solution for 10 minutes. The solution was allowed to warm to room temperature in three hours and solvent was removed by vacuo to give a yellow salt which was washed with dry ether (100 mL×2). Addition of ethyl acetate (300 mL) dissolved the salt and concentrated HCl was dropped to the solution until a pH of 2. The product was washed with water (50 mL), dried, and concentrated under the vacuo to give crude product (10.0 g, 91.7%).

mp 163–164° C. $^1$H NMR (CDCl$_3$, 300 MHz) δ; 9.61 (s, 1H, COOH), 7.42 (m, 1H), 7.29 (t, 1H), 7.10 (t, 1H)ppm. IR (CHCl$_3$) $\upsilon_{max}$ 1706, 1613, 1577, 1454, 1422, 1255, 1153, 1147, 902 cm$^{-1}$. UV (EtOH) $\lambda_{max}$ 269 (ε=1505)nm. MS (FIA) m/z 232.1 (M$^+$, 100). Anal. Calcd. for C$_{10}$H$_4$NO$_3$Cl$_2$F; Theoretical: C, 43.51; H, 1.46; N, 5.07; Found: C, 43.99; H, 1.40; N, 5.07%.

Preparation 5

N-[3,4,5-Trimethoxyphenyl)-3-(3-(2-chloro-5-fluorophenyl)-5-chloroisoxazol-4-oyl)aminophenyl-acetamide

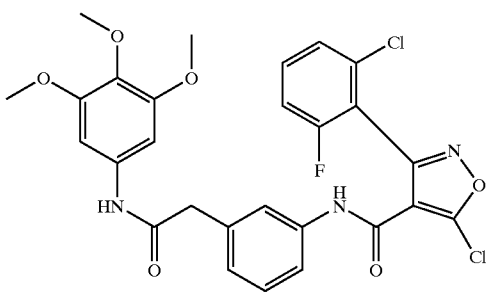

Thionyl chloride (5 mL) was added to a solution of 4-carboxy-5-chloro-3-(2-chloro-6-fluorophenyl)isoxazole (130 mg, 0.471 mmoL) in dry toluene (10 mL). The resulting reaction mixture was stirred at reflux temperature for 4 h under nitrogen and then cooled to room temperature. The solvent was evaporated in vacuo and trace amounts of thionyl chloride removed by coevaporation with toluene (2×25 mL). Resulting crude acid chloride (max. 0.471 mmoL) was dissolved in THF (10 mL) and a solution of amine (176 mg, 0.558 mmoL) in THF:dichloromethane (1:1, 20 mL) was added dropwise and the mixture stirred at room temperature 6 h under nitrogen. The reaction mixture was evaporated to dryness and the solid was titrated with 1N HCl (2×10 mL) to give a brown solid which was further purified by flash chromatography (gradient: 20–70% ethyl acetate/hexanes) to give product as a white solid (237 mg, 89%).

mp 187–188° C. $^1$H NMR (DMSO-d$_6$, 300 MHz) δ; 10.55 (s, 1H, NH), 10.08 (s, 1H, NH), 7.37–7.61 (m, ArH$_5$), 7.25 (m, 1H, ArH), 7.04 (d, J=7.22H, 1H), 6.93 (s, ArH$_2$); 3.68 (s, 6H, CH$_3$), 3.55 (s, 3H, OCH$_3$), 3.53 (s, 2H, CH$_2$)ppm. $^{13}$C NMR DMSO-d$_6$) δ 168.7 (C), 162.1 (C), 158.1 (C), 157.0 (C), 156.3 (C), 154.3 (C), 152.7 (C), 138.14 (C), 136.8 (C), 135.3 (C), 133.7 (C), 133.6 (CH), 133.5 (CH), 132.1 (C), 128.8 (CH), 126.0 (CH), 125.9 (CH), 125.4 (CH), 120.5 (CH), 118.2 (CH), 115.3 (CH), 114.9 (CH), 114.0 (C), 96.9 (CH), 60.1 (CH$_3$), 55.7 (CH$_3$), 43.4 (CH$_2$)ppm. IR (CHCl$_3$) $\upsilon_{max}$ 1687, 1610, 1530, 1508, 1453, 1412, 1132 cm$^{-1}$. UV (EtOH) $\lambda_{max}$ 259 (ε=21847)nm. MS (ES) m/z 574.1 (M$^+$, 92). Anal. Calcd. for C$_{27}$H$_{22}$N$_3$O$_6$Cl$_2$F; Theor.: C, 56.46; H, 3.86; N, 7.32; Cl, 12.32; F, 3.31; Found: C, 56.34; H, 3.86; N, 7.04; Cl, 12.26; F, 3.39%.

Preparation 6

N-(3,4,5-Trimethoxyphenyl) 3-(3-(2-Chloro-5-fluorophenyl)-5-morpholino)isoxazol-4-oyl)aminophenyl Acetamide

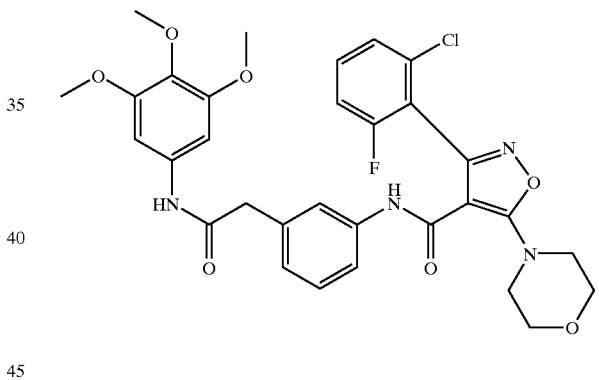

To a solution of 4-[3-(N-3,4,5-trimethoxy-benzylamidomethyl)phenyl-amido-5-chloro-3-(2-chloro-6-fluorophenyl)isoxazole (50 mg, 0.0871 mmol) in DMF (3 mL) was added morpholine (30.4 mg, 0.348 mL). The mixture was stirred at room temperature for three and half hours and then diluted with ethyl acetate (6 mL), washed with 1N HCl (6 mL×3), dried over MgSO$_4$ and concentrated in vacuo to give crude product which was further purified by flash chromatography (gradient: hexanes/ethyl acetate, 8/2 to pure ethyl acetate) to give product as a white solid (37.8 mg, 69.5%); Rf=0.37 (ethyl acetate/hexane, 7/3).

$^1$H NMR (CDCl$_3$, 300 MHz) δ; 6.76–7.43 (m, 6H), 6.74 (s, 2H), 3.87 (m, 4H), 3.81 (m, 9H), 3.71 (m, 4H), 3.63 (s, 2H)ppm. IR (CHCl$_3$) $\upsilon_{max}$ 1671, 1602, 1529, 1508, 1451, 1132 cm$^{-1}$. UV (EtOH) $\lambda_{max}$ 259 (ε=29874)nm. MS (ES) m/z 625.3 (M$^+$, 100). Anal. Calcd. for C$_{31}$H$_{30}$N$_4$O$_7$ClF; Theoretical: C, 59.57; H, 4.84; N, 8.96; F, 3.04; Found: C, 59.29; H, 5.13; N, 8.70; F, 3.30%.

Preparation 7

1-t-Butyl-3-(2-chloro-6-fluoro-phenyl)-4-trifluoroacetyl-pyrazole

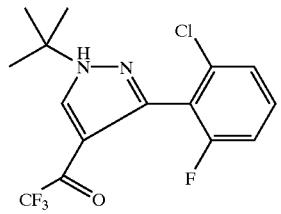

2-Chloro-5-fluorobenzaldehyde tert-butyl hydrazone hydrochloride (4.5 g, 0.017 mole) and sodium acetate (4.5 g, 0.025 mole) were taken in a 250 mL round bottom flask. Acetic acid (100 mL) and DMF (25 mL) were added to the flask and stirred for 5 minutes. Then, ethyl trifluoroacetyl vinyl ether (4.2 g) was added and stirred at 100° C. for one hour. The solvents were removed under vacuum and residue was chromatographed (silica column, 10% ethyl acetate in chloroform). Yield was 2.7 g, 46%.

NMR (CDCl$_3$): δ 1.70 (s, 9H, t-Bu), 7.00–7.15 (m, 1H, Ar), 7.22–7.39 (m, 2H, Ar), 8.19 (s, 1H, pyr). MS (ES): 349 (M$^+$+1).

Preparation 8

1-t-Butyl-3-(2-chloro-6-fluorophenyl)-pyrazole-4-carboxylic Acid

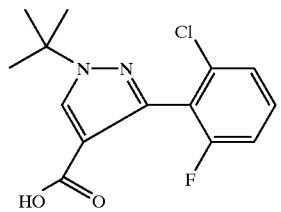

A compound from preparation 7 (2.8 g, 8 mmol) was dissolved in THF (50 ml) and sodium hydride (1.5 g, 60% dispersion, 37 mmol) was added to the solution and stirred for a few minutes. Then water (0.5 ml) was added stirred at 60° C. for one hour. THF was removed under vacuum. The residue was dissolved in water and washed with ethyl acetate to remove any unreacted starting material. Then, the aqueous solution was acidified with 5N HCl and extracted with ethyl acetate (3×100 mL). The combined ethyl acetate extracts were washed with brine, dried over Na$_2$SO$_4$, and evaporated to obtain the pyrazole acid. Yield: 1.7 g, 73%.

NMR (CDCl$_3$): δ 1.62 (s, 9H, t-Bu), 7.05 (t, 1H, Ar), 7.14 (d, 2H, Ar), 8.09 (s, 1H, pyr). MS (ES): 297 (M+1)$^+$, 295 (M−1)$^−$.

Preparation 9

N-(3,4,5-Trimethoxyphenyl) 3-(1-(tert-Butyl)-3-(2-chloro-5-fluoro-phenyl)pyrazol-4-oyl)aminophenyl Acetamide

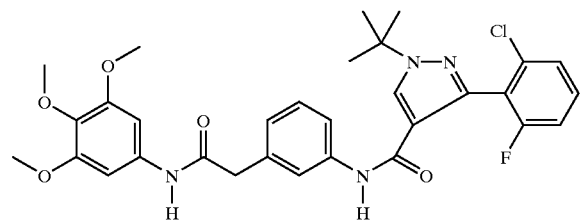

To a solution of a compound from preparation 8 (1 g, 3.37 mmol) dissolved in DMF (20 mL), EDCI (1.3 g, 6.74 mmol), 2-(3-aminophenyl)-N-(3,4,5-trimethoxyphenyl) acetamide (2.13 g, 6.75 mmol) and DMAP (100 mg, catalyst) was added and stirred for 4 h at rt. The reaction mixture was diluted with ethylacetate (200 mL) and washed with water (2×100 mL), acid (1 N HCl, 2×100 mL), brine (2×100 mL), dried over sodium sulfate, evaporated under vacuum and chromatographed (silica column, 50% ethyl acetate in chloroform, isocratic). Yield 1.3 g, 65%.

NMR (CDCl$_3$): δ 1.65 (s, 9H, t-Bu), 3.62 (s, 2H, CH$_2$), 3.70 (s, 3H, OMe), 3.71 (s, 6H, 2 OMe), 6.79 (s, 2H, Ar), 7.00–7.20 (m, 5H, Ar), 7.20–7.50 (m, 2H, Ar), 8.23 (s, 1H, pyr). MS (ES): 629 (M+34), 631 (M+36).

Preparation 10

3-Methyl-5-(2-chloro-6-fluorophenyl)-4-isoxazolecarboxylic Acid Ethyl Ester

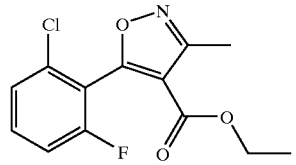

To a solution of ethyl-3-aminomethyl crotonate (4.79 g, 33.5 mmol) in toluene (10 ml), was added triethylamine (3.73 g, 37 mmol). The solution was chilled using an ice bath, and then 2-chloro-5-fluorobenzoyl chloride (6.47 g, 33.5 mmol) was added dropwise over a 20 minute period. The reaction was allowed to warm slowly to room temperature, and stirred for 24 hours. The resulting suspension was then filtered, and the filtrate diluted with ethyl acetate (100 ml) and transferred to a separatory funnel. The organic layer was sequentially washed with water, brine, dried (sodium sulfate), and the volatiles removed under reduced pressure to provide the crude adduct (9.46 g) as a golden solid, and primarily one geometrical isomer:

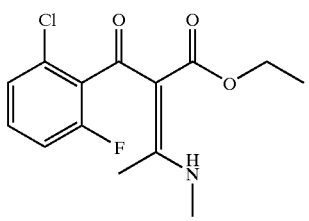

NMR (CDCl₃) δ 6.95–7.4 (3 m, 3H), 3.8 (m, 2H, OEt), 3.12 (d, 3H, —NCH₃), 2.4 (s, 3H, vinyl CH₃), 0.8 (t, OEt). MS (ES) m/z 299.9 (M+H)⁺.

One major side product is acylation of the methylamino group. Crude adduct, however, was then redissolved in glacial HOAc (50 ml) to which was then added NH₂OH.HCl (1.8 g, 1.1 eq). The solution was then heated to reflux for 40–45 minutes to effect isoxazole formation. The reaction mixture was concentrated to an oil, diluted with ether, and transferred to a separatory funnel. The organic phase was washed with saturated bicarbonate, brine, then dried. Filtration and concentration afforded crude isoxazole ethyl ester (7.5 g), which could be used without further purification.

NMR (CDCl₃) δ (7.12, 7.3, 7.43, 3 m), 4.2 (q, 2H), 2.59 (s, 3H, CH₃), 1.1 (t, 3H). MS (ES) m/z 283.9 (M+H)⁺.

Preparation 11

3-Methyl-5-(2-chloro-6-fluorophenyl)-4-isoxazolecarboxylic Acid

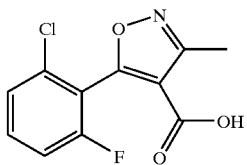

Hydrolysis of the ethyl ester of 3-methyl-5-(2-chloro-6-fluorophenyl)-4-isoxazolecarboxylic acid ethyl ester was accomplished by dissolving the crude ester (7.5 g, approx. 0.027 mol) in THF (250 ml), and adding aqueous LiOH (1.344 g in 100 ml, 2 eq). After stirring overnight at room temperature, the solution was concentrated to ⅔ʳᵈ volume, diluted with EtOAc (200 ml) and 50 ml water, transferred to a separatory funnel, and the aqueous phase collected. The organic phase was washed twice, and the combined aqueous phase was then acidified with 5N HCl. Back extraction with three washings of EtOAc was then followed with a brine wash of the combined organics. After drying over Na₂SO₄, filtration and concentration, clean isoxazole acid was obtained (2.94 g).

NMR (CDCl₃) δ 7.13, 7.32 7.46 (3 m, 3H), 2.58 (s, CH₃). MS (ES) m/z 253.8, 255.8 (M–H)⁻. EA, calc'd for C₁₁H₇ClFNO₃; Theoretical: C, 51.68; H, 1.87; N, 5.48; Found: C, 51.85; H, 1.87; N, 5.20%.

Preparation 12

N-(3,4,5-Trimethoxyphenyl) 3-(3-Methyl-5-(2-chloro-5-fluoro-phenyl)isoxazol-4-oyl)aminophenyl Acetamide

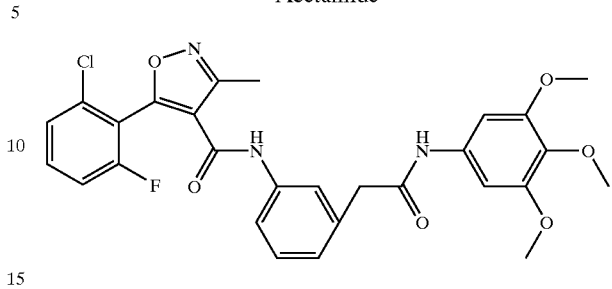

To 3-methyl-5-(2-chloro-5-fluorophenyl)-4-isoxazolecarboxylic acid, (38.4 mg, 0.15 mmol) in DMF (3 ml) was added DMAP (2 mg), followed by EDC.HCl (57 mg, 0.3 mmol). After a few minutes of stirring, 2-(3-aminophenyl)-N-(3,4,5-trimethoxyphenyl)acetamide (94.8 mg, 0.3 mmol) was added, and the reaction proceeded for 18 hr at room temperature. The solution was then diluted with EtOAc (50 ml) and 1N HCl (20 ml), and transferred to a separatory funnel. The aqueous phase was re-extracted twice with EtOAc, and the combined organics were then washed with saturated bicarbonate, brine, and dried. After filtration, the solution was concentrated to afford 20 mg of crude adduct. This material was purified by running the sample through a Bond-Elut Silica cartridge (500 mg) using 1:1 hexane/EtOAc as eluting solvent. Thus, a pure sample (10 mg) of amide was obtained.

NMR (CDCl₃) δ 7.1, 7.2, 7.3, 7.4, 7.55 (5 m, 6H), 6.79 (s, 2H), 3.8 (2s, 9H), 3.64 (s, 2H), 2.6 (s, 3H). MS (ES) m/z 553.8 (M+H)⁺, 570.9 (M+NH3)⁺. EA, calc'd for C₂₈H₂₅ClFN₃O₆; Theoretical: C, 60.71; H, 4.55; N, 7.59; Found: C, 59.83; H, 4.79; N, 6.83%.

Preparation 13

2-Fluorobenzaldehyde Oxime

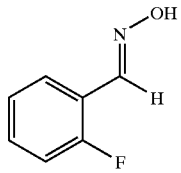

This reaction was carried out in a manner similar to that described in the literature (Liu, K. C.; Shelton, B. R.; Howe, R. K. *J. Org. Chem.* 1980, 45, 3916–3918). To a mixture of 2-fluorobenzaldehyde (5.20 g, 41.9 mmol) and hydroxylamine hydrochloride (3.20 g, 46.1 mmol), EtOH (15 ml), H₂O (15 ml), and ice (25 g) was added 50% NaOH (5.1 g in 5.1 ml H₂O). The reaction was warmed to room temperature and stirred for 1 h. Ice was added to the reaction, followed by addition of 2N HCl until the pH was 2. The mixture was extracted with Et₂O. The organic extract was washed (brine) and dried (MgSO₄). Filtration and concentration gave oxime 2-fluorobenzaldehyde oxime (5.06 g, 87%) as a solid that was used without further purification.

¹H NMR (300 MHz, CDCl₃) δ 9.02 (br s, 1H), 8.02 (m, 1H), 7.73 (m, 1H), 7.35 (m, 1H), 7.20–7.00 (m, 2H)ppm. Anal. calc. for C₇H₆FNO; Theoretical: C, 60.43, H, 4.35, N, 10.07; Found: C, 60.55, H, 4.36, N, 10.24%. MS (m/z) 140.2 [M+1].

Preparation 14

2-Fluorobenzoylchloride Oxime

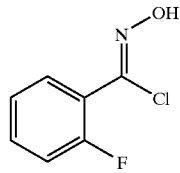

This reaction was carried out in a manner similar to that described in the literature (Liu, K. C.; Shelton, B. R.; Howe, R. K. *J. Org. Chem.* 1980, 45, 3916–3918). To a solution of 2-fluorobenaldehyde oxime (1.00 g, 7.2 mmol), in DMF (6 ml) was added N-chlorosuccinimide (0.99 g, 7.4 mmol). HCl (gas, 5 ml syringe taken from the vapors of a concentrated solution of HCl) was bubbled into the solution. After stirring for 1 h, $Et_2O$ and $H_2O$ were added. The organic layer was separated, washed ($H_2O$ and brine), and dried ($MgSO_4$). Filtration and concentration gave 2-fluorobenzoylchloride oxime (0.96 g, 77%) as an off white solid that was used without further purification. $^1$H NMR (300 MHz, $CDCl_3$) δ 9.18 (s, 1H), 7.71 (dt, 1H, J=1.5, 7.8 Hz), 7.44 (m, 1H), 7.23 (app t, 1H, J=8.8 Hz), 7.16 (ddd, J=1.0, 8.3, 10.7 Hz)ppm.

Anal. calc. for $C_7H_5ClFNO$; Theoretical: C, 48.44, H, 2.90, N, 8.07; Found: C, 48.80, H, 2.72, N, 8.04%. MS (FD) (m/z) 174.0 [M+1].

Preparation 15

4-Methoxycarbonyl-5-methyl-3-(2-fluorophenyl)isoxazole

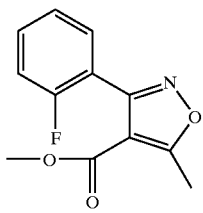

To a solution (0° C., $N_2$) of 2-fluorobenzoylchloride oxime (0.50 g, 2.9 mmol) and methyl-2-butynoate (0.57 g, 5.8 mmol) in $Et_2O$ (15 ml) was added a solution of $Et_3N$ (0.52 ml) in $Et_2O$ (2 ml) over a period of 1 h followed by warming to room temperature while stirring overnight (17 h). The reaction was diluted with $Et_2O$, washed ($H_2O$ then brine), dried ($MgSO_4$), filtered, and concentrated. Column chromatography (silica gel, hexanes/EtOAc gradient) gave the title compound (0.39 g, 58%).

$^1$H NMR (300 MHz, $CDCl_3$) δ 7.44 (m, 2H), 7.20 (m, 1H), 7.17 (m, 1H), 3.68 (s, 3H), 2.70 (s, 3H)ppm. MS (ES) (m/z) 236.0 [M+1].

Preparation 16

4-Carboxy-5-methyl-3-(2-fluorophenyl)isoxazole

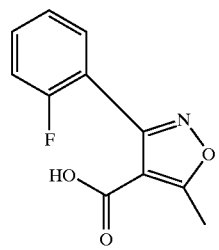

A solution of 4-methoxycarbonyl-5-methyl-3-(2-fluorophenyl)isoxazole (2.20 g, 8.84 mmol), MeOH (25 ml), and 2N NaOH (8.8 ml) was heated at 50° C. overnight (19 h). The reaction was cooled to room temperature, diluted with $H_2O$, and acidified (2N HCl) to less than pH 3. The mixture was extracted with EtOAc (twice) and the combined extracts were washed (brine), dried ($MgSO_4$), filtered, and concentrated to give the title compound (1.88 g, 96%). This material was used without further purification.

$^1$H NMR (300 MHz, $CDCl_3$) δ 7.45 (m, 2H), 7.15 (m, 2H), 2.78 (s, 3H)ppm. Anal. Calc. for $C_{11}H_8FNO_3$; Theoretical: C, 59.73, H, 3.65, N, 6.33; Found: C, 59.38, H, 3.27, N, 6.85%. MS (ES) (m/z) 220.2 [M−1].

Preparation 17

N-(3,4,5-Trimethoxyphenyl) 3-(5-Methyl-3-(2-fluoro-phenyl)isoxazol-4-oyl)aminophenyl Acetamide

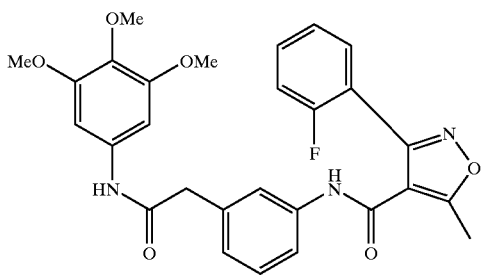

To a solution of 4-methoxycarbonyl-5-methyl-3-(2-fluorophenyl)isoxazole (1.00 g, 4.52 mmol) in $CH_2Cl_2$ (30 ml) was added EDCI (1.51 g, 9.04 mmol), DMAP (0.11 g, 0.90 mmol), and 2-(3-aminophenyl)-N-(3,4,5-trimethoxyphenyl)acetamide (1.70 g, 5.42 mmol). The reaction was allowed to stir for 6 h then applied to a silica gal column eluting first $CH_2Cl_2$ with followed by 10% acetone in $CH_2Cl_2$ to give the title compound (1.44 g, 62%).

$^1$H NMR (400 MHz, $CDCl_3$) δ 7.64–7.54 (m, 2H), 7.42 (br s, 1H), 7.36 (dt, 1H, J=1.0, 7.3 Hz), 7.25 (m, 2H), 7.10 (m, 2H), 6.96 (d, 1H, J=7.8 Hz), 6.75 (s, 2H), 3.80 (s, 6H), 3.78 (s, 3H), 3.64 (s, 2H), 2.78 (s, 3H)ppm. MS (ES) (m/z) 518.2 [M−1].

Preparation 18

2-Chloro-6-fluorobenzaldehyde Oxime

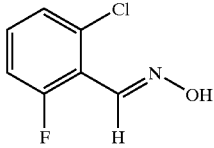

To a solution of 2-chloro-6-fluorobenzaldehyde (15.0 g, 94.6 mmol) and hydroxylamine hydrochloride (7.90 g, 114 mmol) in EtOH (25 ml), H$_2$O (25 ml), and ice (40 g) was added NaOH (19 ml, 50% wt. solution). Ice was added during the addition of the NaOH to maintain the reaction temperature below 40 degrees C. The mixture was stirred at room temperature for 1 h. Ice was added, the pH adjusted to 6 with HCl (2 N), and extracted twice with Et$_2$O. The combined Et$_2$O layers were washed (brine) and dried (MgSO$_4$). Filtration and concentration gave a yellow-brown solid that was recrystallized from Et$_2$O/hexanes to give 2-chloro-5-fluorobenzaldehyde oxime (12.2 g, 74%).

$^1$H NMR (300 MHz, CDCl$_3$) δ 9.82 (br s, 1H), 8.47 (s, 1H), 7.25 (m, 2H), 7.07 (m, 1H)ppm. Anal. calc. for C$_7$H$_5$ClFNO; Theoretical: C, 48.44, H, 2.90, N, 8.07; Found: C, 48.73, H, 2.89, N, 7.95%. MS (ES) (m/z) 174.1 [M+1].

Preparation 19

2-Chloro-6-fluorobenzoylchloride Oxime

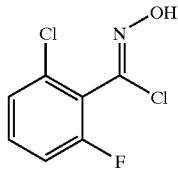

To a solution of 2-chloro-6-fluorobenzaldehyde oxime (5.13 g, 29.6 mmol) in DMF (50 ml) was added a portion of N-chlorosuccinimide followed by a syringe of HCl gas (5 ml from the vapors of a conc. HCl solution). The temperature increased slightly and the rest of the N-chlorosuccinimide (total of 4.07 g, 30.5 mmol) was added. After stirring at room temperature for 1 h, ice was added and the mixture was extracted twice with diethyl ether. The combined organic fractions were washed (brine), dried (MgSO$_4$), filtered, and concentrated. Column chromatography (silica gel, hexane/Et$_2$O gradient) gave 2-chloro-6-fluorobenzoylchloride oxime (4.83 g, 78%).

Preparation 20

4-Methoxycarbonyl-5-phenyl-3-(2-chloro-6-fluorophenyl)isoxazole

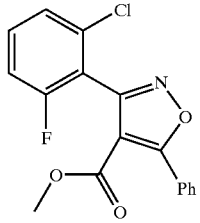

To a solution of 2-chloro-6-fluorobenzoylchloride oxime (1.04 g, 5.00 mmol) and methyl-3-phenyl-2-propynoate (1.20 g, 7.50 mmol) in Et$_2$O (25 ml) at 0° C. under nitrogen was added a solution of triethyl amine (0.834 ml, 6.00 mmol) in Et$_2$O (3 ml) over 1 h. The reaction was allowed to warm to room temperature overnight (17 h). The mixture was diluted with Et$_2$O and H$_2$O, the layers separated, and the organic fraction was dried (MgSO$_4$). Column chromatography (silica gel, hexane/Et$_2$O gradient) gave the title compound (1.53 g, 92%).

$^1$H NMR (300 MHz, CDCl$_3$) δ 8.05 (dd, 2H, J=2.0, 7.7 Hz), 7.55 (m, 3H), 7.45–7.25 (m, 2H), 7.14 (t, 1H, H=8.3 Hz), 3.64 (s, 3H)ppm. IR (CHCl$_3$ solution) v 1725 (CO) cm$^{-1}$. Anal. calc. for C$_{17}$H$_{11}$ClFNO$_3$; Theoretical: C, 61.55, H, 3.34, N, 4.22; Found: C, 61.35, H, 3.42, N, 4.42%. MS (ES) (m/z) 332.1 [M+1].

Preparation 21

4-Carboxy-5-phenyl-3-(2-chloro-6-fluorophenyl)isoxazole

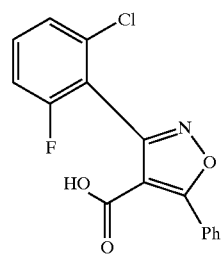

To a solution of 4-methoxycarbonyl-5-phenyl-3-(2-chloro-6-fluorophenyl)isoxazole (0.70 g, 2.1 mmol) in methanol (5 ml) and THF (2 ml) was added a solution of 2N NaOH (4 ml) at room temperature. The mixture was heated to 55° C. for 1.5 h. Upon cooling to room temperature, aqueous HCl was added until the pH was below 4. The mixture was diluted with ethyl acetate and water and the fractions separated. The organic fraction was washed (brine) and dried (MgSO$_4$). Filtration and concentration gave the title compound (0.67 g, 100%), which was used without further purification.

IR (KBr) v 1696 (CO)cm$^{-1}$. MS (ES) (m/z) 316.0 [M−1].

Preparation 22

N-(3,4,5-Trimethoxyphenyl)-3-(5-phenyl-3-(2-chloro-6-fluoro-phenyl)isoxazol-4-oyl)aminophenyl Acetamide

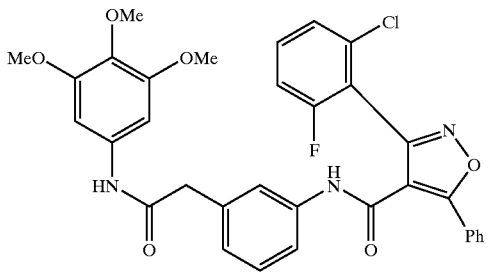

To a solution of 4-carboxy-5-phenyl-3-(2-chloro-6-fluorophenyl)isoxazole (0.135 g, 0.425 mmol) and 2-(3-aminophenyl)-N-(3,4,5-trimethoxyphenyl)acetamide (0.129 g, 0.408 mmol) in dichloromethane (5 ml) was added EDCI (0.082 g, 0.51 mmol) and DMAP (0.062 g, 0.51 mmol) and stirred for 14 h. The mixture was applied to a silica gel chromatography column. Elution with hexanes and ethyl acetate (gradient) gave the title compound (0.162 g, 64%).

$^1$H NMR (400 MHz, CDCl$_3$) δ 7.95 (dd, 1H, J=1.7, 7.5 Hz), 7.57–7.50 (m, 2H), 7.46–7.40 (m, 2H), 7.35–7.04 (m, 9H), 6.73 (s, 2H), 3.79 (s, 6H), 3.77 (s, 3H), 3.64 (s, 2H)ppm. MS (ES) (m/z) 616.2 [M+1].

Preparation 23

2,6-Difluorobenzaldehyde Oxime

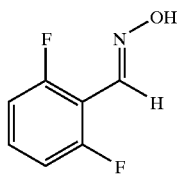

In a fashion similar to that for preparation 13, 2,6-difluorobenzaldehyde (5.00 g, 35.2 mmol), hydroxylamine hydrochloride (2.93 g, 29.6 mmol), NaOH (7.04 g in 7.0 ml of water), ethanol (15 ml), water (15 ml), and ice (30 g) afforded 2,6-difluorobenzaldehyde oxime (5.13 g, 93%).

$^1$H NMR (CDCl$_3$, 300 MHz) δ 9.85 (br s, 1H), 8.33 (s, 1H), 7.32 (m, 1H), 6.95 (t, 2H, J=8.4 Hz)ppm. MS (FD) (m/z) 157.0 [M+].

Preparation 24

2,6-Difluorobenzoylchloride Oxime

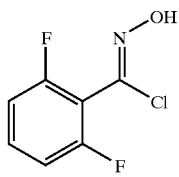

In a fashion similar to that for preparation 14, 2,6-difluorobenzaldehyde oxime (2.00 g, 12.7 mmol), N-chlorosuccinimide (1.75 g, 13.2 mmol), and DMF (20 ml) gave 2,6-difluorobenzoylchloride oxime (1.58 g, 65%) after column chromatography (silica gel, hexanes/diethyl ether gradient).

$^1$H NMR (CDCl$_3$, 300 MHz) δ 8.56 (s, 1H), 7.55–7.37 (m, 1H), 6.95 (app t, 2H, J=7.3 Hz)ppm. MS (FD) (m/z) 191.0 [M+].

Preparation 25

4-Methoxycarbonyl-5-methyl-3-(2,6-difluorophenyl)isoxazole

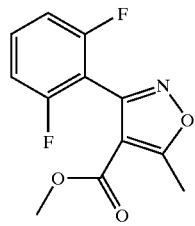

In a fashion similar to that for preparation 15, 2,6-difluorobenzoylchloride oxime (1.00 g, 5.19 mmol), methyl-2-butynoate (1.01 g, 10.4 mmol), triethyl amine (0.94 ml, 6.8 mmol) in diethyl ether (3 ml), and diethyl ether (25 ml) afforded 4-methoxycarbonyl-5-methyl-3-(2,6-difluorophenyl)isoxazole (0.80 g, 61%) after purification by column chromatography (silica gel, hexanes/diethyl ether gradient).

$^1$H NMR (300 MHz, CDCl$_3$). δ 7.43 (m, 1H), 7.00 (app t, 2H, J=7.8 Hz), 3.73 (s, 3H), 2.77 (s, 3H)ppm. IR (KBr) ν 1721 (CO)cm$^{-1}$. MS (ES) (m/z) 254.1 [M+1]. Anal. Calc. for C$_{12}$H$_9$F$_2$NO$_3$; Theoretical: C, 56.92, H, 3.58, N, 5.53; Found: C, 56.76, H, 3.48, N, 5.57%.

Preparation 26

4-Carboxy-5-methyl-3-(2,6-difluorophenyl)isoxazole

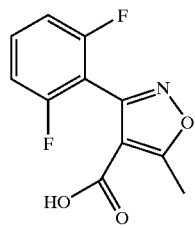

In a manner similar to that for preparation 16, 4-methoxycarbonyl-5-methyl-3-(2,6-difluorophenyl)isoxazole (0.244 g, 0.910 mmol), 5N NaOH (1 ml, 5.0 mmol), and methanol (10 ml) afforded 4-carboxy-5-methyl-3-(2,6-difluorophenyl)isoxazole (0.216 g, 93%) which was used without purification.

$^1$H NMR (400 MHz, CDCl$_3$) δ 7.39 (app tt, 1H, J=6.4, 8.3 Hz), 6.97 (app t, 2H, J=8.3 Hz), 2.74 (s, 3H)ppm. IR (CHCl$_3$ solution) ν 1698 (CO)cm$^{-1}$. MS (ES) (m/z) 240.0 [M+1].

Preparation 27

N-(3,4,5-Trimethoxyphenyl)-3-(5-methyl-3-(2,6-difluoro-phenyl)isoxazol-4-oyl)aminophenyl Acetamide

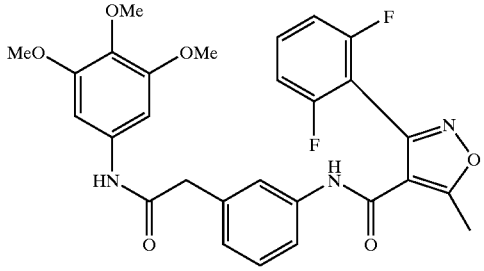

4-Carboxy-5-methyl-3-(2,6-difluorophenyl)isoxazole (0.120 g, 0.50 mmol), 2-(3-aminophenyl)-N-(3,4,5-trimethoxyphenyl)acetamide (0.174 g, 0.55 mmol), EDCI (0.161 g, 1.00 mmol), DMAP (0.012 g, 0.10 mmol), and dichloromethane (5 ml) were allowed to react for 16 h in a fashion similar to that for example 5. Column chromatography (silica gel, hexanes/ethyl acetate gradient) afforded the title compound (0.142 g, 53%).

$^1$H NMR (400 MHz, CDCl$_3$) δ 7.50 (app tt, 1H, J=5.0, 8.8 Hz), 7.39 (br s, 1H), 7.25 (t, 1H, J=7.8 Hz), 7.10–7.02 (m, 5H), 6.98 (d, 1H, J=7.8 Hz), 6.71 (s, 2H), 3.77 (s, 6H), 3.74 (s, 3H), 2.77 (s, 3H). MS (ES) (m/z) 538.2 [M+1].

Preparation 28

4-Methoxycarbonyl-5-hexyl-3-(2-chloro-6-fluorophenyl)isoxazole

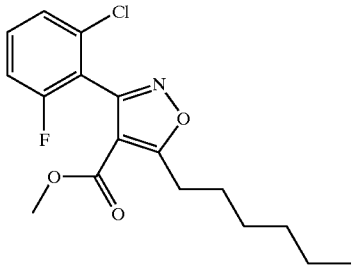

In a fashion similar to that for preparation 15, 2-chloro-5-fluorobenzoylchloride oxime (0.750 g, 3.61 mmol), methyl-2-nonynoate (1.32 ml, 7.21 mmol), Et$_3$N (0.652 ml, 4.69 mmol) in Et$_2$O (3 ml), and Et$_2$O (15 ml) gave 4-methoxycarbonyl-5-hexyl-3-(2,6-difluorophenyl)isoxazole (0.806 g, 66%) after column chromatography (silica gel, hexanes/Et$_2$O gradient).

$^1$H NMR (300 MHz, CDCl$_3$) d 7.39 (dt, 1H, J=5.9, 8.1 Hz), 7.29 (d, 1H, J=8.1 Hz), 7.10 (dt, 1H, J=1.1, 8.4 Hz), 3.68 (s, 3H), 3.17 (t, 2H, J=7.7 Hz), 1.82 (m, 2H), 1.43–1.31 (m, 6H), 0.90 (m, 3H)ppm. IR (CHCl$_3$ solution) ν 1723 (CO)cm$^{-1}$. MS (ES) (m/z) 340.1 [M+1].

Preparation 29

4-Carboxy-5-hexyl-3-(2-chloro-6-fluorophenyl) isoxazole

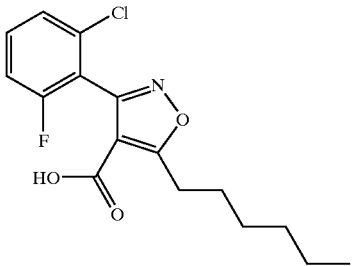

4-Methoxycarbonyl-5-hexyl-3-(2,6-difluorophenyl) isoxazole (0.30 g, 0.88 mmol) was dissolved in methanol (10 ml), 5N NAOH (1 ml) was added, and the mixture was heated at 50° C. for 2 h. Upon cooling to room temperature, HCl was added until pH 1. Extraction with ethyl acetate and subsequent washing of the organic fraction (brine), drying (MgSO$_4$), filtering, and concentrating afforded the desired 4-carboxy-5-hexyl-3-(2,6-difluorophenyl)isoxazole (0.21 g, 72%) that was used without further purification.

$^1$H NMR (400 MHz, CDCl$_3$) δ 7.34 (dt, 1H, J=5.9, 8.3 Hz), 7.24 (d, 1H, J=8.3 Hz), 7.05 (t, 1H, J=8.3 Hz), 3.13 (t, 2H, J=7.8 Hz), 1.78 (quint, 2H, J=7.3 Hz), 1.40–1.25 (m, 6H), 0.85 (m, 3H)ppm. IR (KBr) 3435 (br, OH), 1687 (CO)cm$^{-1}$. MS (ES) (m/z) 324.4 [M−1].

Preparation 30

N-(3,4,5-Trimethoxyphenyl)-3-(5-hexyl-3-(2-chloro-6-fluoro-phenyl)isoxazol-4-oyl)aminophenyl Acetamide

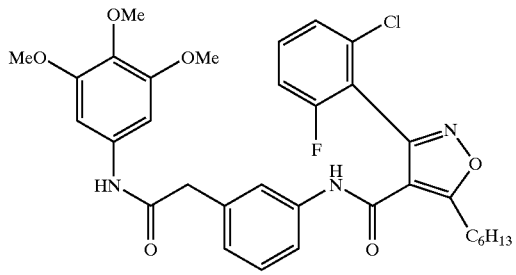

4-Carboxy-5-hexyl-3-(2,6-difluorophenyl)isoxazole (150 mg, 0.46 mmol), 2-(3-aminophenyl)-N-(3,4,5-trimethoxyphenyl)acetamide (160 mg, 0.51 mmol), EDCI (150 mg, 0.78 mmol), DMAP (12 mg, 0.10 mmol) were reacted in CH$_2$Cl$_2$ (5 ml) for 19 h then applied to a silica gel column. Elution with hexanes/EtOAc (gradient) gave the title compound (185 mg, 65%).

$^1$H NMR (400 MHz, CDCl$_3$) δ 7.48 (dt, 1H, J=5.8, 8.3 Hz), 7.38 (d, 1H, J=8.3 Hz), 7.34 (s, 1H), 7.26–7.18 (m, 2H), 7.03 (d, 1H, J=7.8 Hz), 6.98 (s, 1H), 6.95 (s, 1H), 6.90 (d, J=9.3 Hz), 6.70 (s, 2H), 3.77 (s, 6H), 3.75 (s, 3H), 3.61 (s, 2H), 3.19 (t, 2H, J=Hz), 1.82 (m, 2H), 1.38 (m, 2H), 1.29 (m, 4H), 0.85 (m, 3H)ppm. MS (ES) (m/z) 624.2 [M+1].

Preparation 31

2,4-Difluorobenzaldehyde Oxime

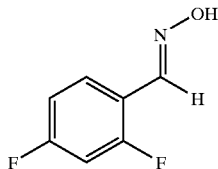

In a fashion similar to that for preparation 13, 2,4-difluorobenzaldehyde (5.00 g, 35.2 mmol), hydroxylamine hydrochloride (2.94 g, 42.3 mmol), NaOH (7.04 g, 88.0 mmol; as a 50% solution by weight in water), ethanol (15 ml), $H_2O$ (15 ml), and ice (30 g) gave 2,4-difluorobenzaldehyde oxime (4.62 g, 84%) which was used without purification.

$^1$H NMR (300 MHz, CDCl$_3$) δ 8.26 (s, 1H), 7.66 (t, 1H, J=8.3 Hz), 7.14–7.07 (m, 2H)ppm. MS (EI) (m/z) 157.0 [M+].

Preparation 32

2,4-Difluorobenzoyl Chloride Oxime

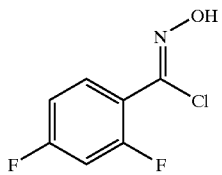

In a fashion similar to that for preparation 14, 2,4-difluorobenzaldehyde oxime (2.52 g, 16.1 mmol), N-chlorosuccinimide (2.21 g, 16.5 mmol), and dimethyl formamide (25 ml) gave 2,4-difluorobenzoyl chloride oxime (2.11 g, 68%) after chromatography (silica gel, hexanes/ether).

$^1$H NMR (400 MHz, CDCl$_3$) δ 8.48 (s, 1H), 7.62 (dt, 1H, J=6.4, 8.3 Hz), 6.93–6.83 (m, 2H)ppm. IR (CHCl$_3$ solution) ν 3555, 1613, 1506, 1429, 1272, 1258 cm$^{-1}$.

Preparation 33

4-Ethoxycarbonyl-5-methyl-3-(2,4-difluorophenyl)isoxazole

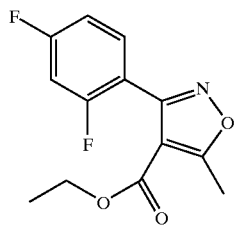

In a fashion similar to that for preparation 15, 2,4-difluorobenzoyl chloride oxime (2.00 g, 10.4 mmol), ethyl 2-butynoate (1.76 g, 15.7 mmol), triethyl amine (2.9 ml, 21 mmol) in diethyl ether (10 ml), and diethyl ether 30 ml) gave 4-ethoxycarbonyl-5-methyl-3-(2,4-difluorophenyl) isoxazole (1.62 g, 58%) after column chromatography (silica gel, hexanes/diethyl ether gradient).

$^1$H NMR (400 MHz, CDCl$_3$) δ 7.43 (1H, dt, J=6.4, 8.3 Hz), 6.93 (1H, app dt, J=2.9, 8.8 Hz), 6.86 (1H, app dt, J=2.4, 9.8 Hz), 4.16 (q, 2H, J=6.9 Hz), 2.70 (s, 3H), 1.14 (t, 3H), J=6.9 Hz)ppm. IR (CHCl$_3$ solution) 1720 (CO)cm$^{-1}$. MS (ES) (m/z) 268.3 [M+1].

Preparation 34

4-Carboxy-5-methyl-3-(2,4-difluorophenyl)isoxazole

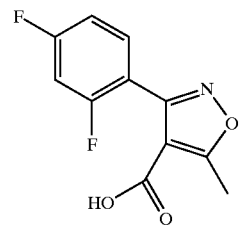

4-Ethoxycarbonyl-5-methyl-3-(2,4-difluorophenyl)isoxazole (305 mg, 1.14 mmol), 5N NaOH (1.0 ml, 5 mmol), methanol (5 ml), and THF (1 ml) were heated at 50° C. for 16 h. Ice was added and the pH was adjusted to 2–3 with 1N HCl. Extraction with EtOAc followed by washing (brine), drying (Na$_2$SO$_4$), filtering, and concentration gave the crude 4-carboxy-5-methyl-3-(2,4-difluorophenyl)isoxazole (286 mg, 99%) which was used without further purification.

Preparation 35

N-(3,4,5-trimethoxyphenyl)-3-(5-methyl-3-(2,4-difluoro-phenyl)isoxazol-4-oyl)aminophenyl Acetamide

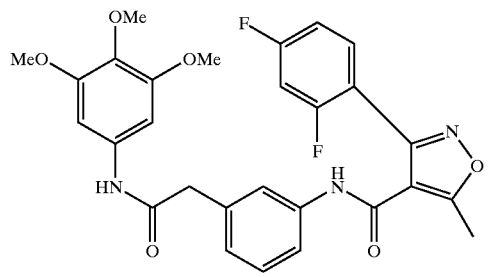

4-Carboxy-5-methyl-3-(2,difluorophenyl)isoxazole (97 mg, 0.41 mmol) was dissolved (room temperature, N$_2$) in dichloromethane (5 ml) followed by addition of DMF (0.005 ml) and oxalyl chloride (0.070 ml, 0.82 mmol). After 1 h, the volatiles were removed. The residue and 2-(3-aminophenyl)-N-(3,4,5-trimethoxyphenyl)acetamide (110 mg, 0.35 mmol) were dissolved in CH$_2$Cl$_2$ (5 ml) and DMF (1 ml) (room temperature, N$_2$), Et$_3$N (0.111 ml, 0.80 ml) and DMAP (5 mg, 0.04 mmol) were added. The reaction was stirred for 3 h. The mixture was applied to a silica gel column and elution (hexanes/EtOAc gradient) gave the title compound (152 mg, 81%).

$^1$H NMR (400 MHz, CDCl$_3$) δ 7.60 (app q, 1H, J=7.8 Hz), 7.45 (s, 1H), 7.28 (t, 1H, J=7.8 Hz), 7.20 (s, 1H), 7.10–7.00 (m, 5H), 6.97–6.92 (m, 1H), 6.72 (s, 2H), 3.77 (s, 6H), 3.75 (s, 3H), 3.63 (s, 2H), 2.73 (s, 3H)ppm. MS (ES) (m/z) 538.2 [M+1].

Preparation 36

2-Fluoro-4-bromobenzaldehyde Oxime

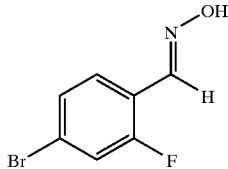

In a fashion similar to that for preparation 13, 4-bromo-2-fluorobenzaldehyde (5.00 g, 24.6 mmol), hydroxylamine hydrochloride (2.05 g, 29.6 mmol), NaOH (4.92 g, 61.5 mmol; in a 50% by weight solution), ethanol (15 ml), water (15 ml), and ice (30 g) gave the title compound (4.12 g, 77%) which was used without purification.

$^1$H NMR (400 MHz, CDCl$_3$) δ 8.26 (s, 1H), 7.57 (t, 1H, J=8.8 Hz), 7.28–7.21 (m, 2)ppm. MS (ES) (m/z) 217.9 [M+1], 219.9 [M+3].

Preparation 37

2-Fluoro-4-bromobenzoyl Chloride Oxime

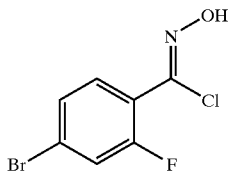

In a fashion similar to that for preparation 14, 2-Fluoro-4-bromo-benzaldehyde oxime (2.77 g, 12.7 mmol), N-chlorosuccinimide (1.76 g, 13.2 mmol), and DMF (25 ml) gave 2-fluoro-4-bromo-benzoyl chloride oxime (2.61 g, 81%) after filtration through a plug of silica gel eluting with hexanes/Et$_2$O.

$^1$H NMR (400 MHz, CDCl$_3$) δ 8.62 (s, 1H), 7.49 (dd, 1H, J=1.5, 7.8 Hz), 7.34–7.29 (m, 2H)ppm. Anal. calc. for C$_7$H$_4$BrClFNO; Theoretical: C, 33.30, H, 1.60, N, 5.55; Found: C, 33.66, H, 1.58, N, 5.45%.

Preparation 38

4-Ethoxycarbonyl-5-methyl-3-(2-fluoro-4-bromophenyl)isoxazole

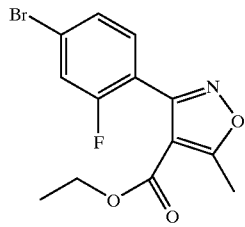

In a fashion similar to that described for preparation 15, 2-fluoro-4-bromo-benzoyl chloride oxime (2.00 g, 7.92 mmol), ethyl-2-butynoate (1.33 g, 11.9 mmol), triethylamine (2.2 ml, 15.8 mmol) in diethyl ether (10 ml), and diethyl ether (20 ml) gave 4-ethoxycarbonyl-5-methyl-3-(2-fluoro-4-bromophenyl)isoxazole (2.16 g, 83%) after column chromatography (silica gel, hexanes/diethyl ether gradient). $^1$H NMR (400 MHz, CDCl$_3$) δ 7.36–7.29 (m, 3H), 4.16 (q, 2H, J=6.8 Hz), 2.70 (s, 3H), 1.15 (t, 3H, J=6.9 Hz)ppm.

IR (KBr) ν 1719 (CO)cm$^{-1}$. Anal. Calc. for C$_{13}$H$_{11}$BrFNO$_3$; Theoretical: C, 47.59, H, 3.38, N, 4.27; Found C, 47.51, H, 3.30, N, 4.26%. MS (ES) (m/z) 328.1 [M+1].

Preparation 39

4-Carboxy-5-methyl-3-(2-fluoro-4-bromophenyl)isoxazole

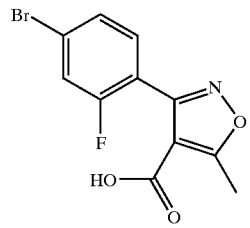

In a fashion similar to that described for preparation 16 (120 mg), 4-ethoxycarbonyl-5-methyl-3-(2-fluoro-4-bromophenyl)isoxazole (350 mg, 1.06 mmol), 5N NaOH (1 ml, 5 mmol), methanol (5 ml), and THF (1 ml) gave 4-carboxy-5-methyl-3-(2-fluoro-4-bromophenyl)isoxazole (320 mg, 100%) that was used without purification.

1H NMR (300 MHz, CDCl$_3$) d 7.43–7.35 (m, 3H), 2.78 (s, 3H)ppm. MS (EI) (m/z) 298.1[M−1], 300.1[M−3].

Preparation 40

N-(3,4,5-Trimethoxyphenyl)-3-(5-methyl-3-(2-fluoro-4-bromo-phenyl)isoxazol-4-oyl)aminophenyl Acetamide

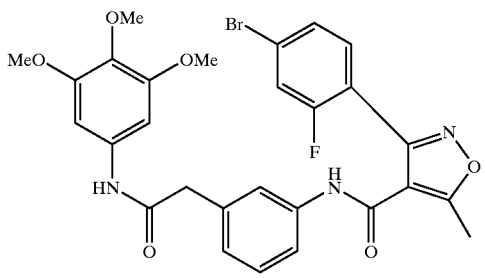

In a fashion similar to that described for preparation 35, 4-carboxy-5-methyl-3-(2-fluoro-4-bromophenyl)isoxazole (119 mg, 0.40 mmol), oxalyl chloride (0.070 ml, 0.80 mmol), dimethylformamide (0.010 ml), dichloromethane (5 ml), 2-(3-aminophenyl)-N-(3,4,5-trimethoxyphenyl)acetamide (110 mg, 0.35 mmol), triethylamine (0.111 ml, 0.80 mmol), DMAP (5 mg), dimethylformamide (1 ml), dichloromethane (5 ml) gave the title compound (138 mg, 66%) after column chromatography (silica gel, hexanes/ethyl acetate gradient).

$^1$H NMR (400 MHz, CDCl$_3$) δ 7.52–7.42 (m, 3H), 7.37 (dd, 1H, J=1.5, 9.3 Hz), 7.29 (t, 1H, J=7.8 Hz), 7.20 (s, 1H), 7.09–7.04 (m, 4H), 6.72 (s, 2H), 3.77 (s, 6H), 3.75 (s, 3H), 3.64 (s, 2H), 2.72 (s, 3H)ppm. MS (ES) (m/z) 598.1 [M+1], 600.1 [M+3].

Preparation 41

4-Methoxycarbonyl-5-methyl(tetrahydropyran-2-yl)-3-(2-chloro-6-fluoro-phenyl)isoxazole

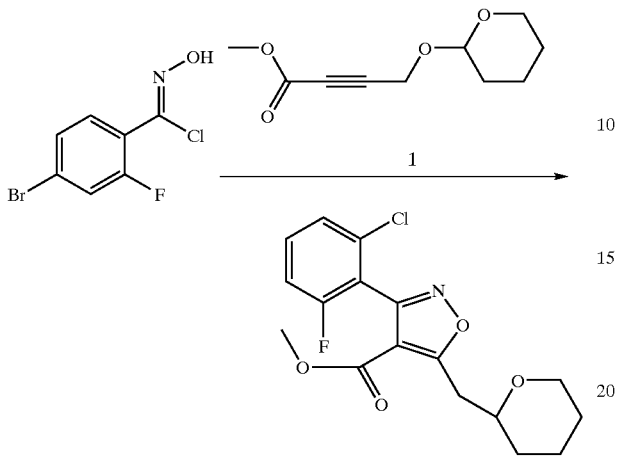

2-Chloro-6-fluoro-benzoyl chloride oxime (3.70 g, 17.8 mmol), alkyne 1 (for preparation see Earl, R. A. and Townsend, L. B. *Organic Synthesis* 1981, 60, 81) (5.20 g, 26.7 mmol), triethyl amine (2.72 ml, 19.6 mmol) in diethyl ether (3 ml), and diethyl ether (50 ml) were reacted in a fashion similar to that for example 3 to provide the title compound (4.32 g, 66%) after column chromatography (silica gel, hexanes/ethyl acetate gradient).

$^1$H NMR (400 MHz, CDCl$_3$) δ 7.36 (dt, 1H, J=5.9, 8.3 Hz), 7.27 (m, 1H), 7.07 (app t, 1H, J=8.9 Hz), 5.12 (½ AB, 1H, J=13.7 Hz), 4.98 (½ AB, 1H, J=13.7 Hz), 4.84 (t, 1H, J=3.4 Hz), 3.85 (m, 1H), 3.67 (s, 3H), 3.55 (m, 1H), 1.90–1.50 (m, 6H)ppm. IR (CHCl$_3$ solution) v 1731 (CO) cm$^{-1}$. Anal. calc. for C$_{17}$H$_{17}$ClFNO$_5$; Theoretical: C, 55.22, H, 4.63, N, 3.79; Found: C, 55.24, H, 4.59, N, 3.78%.

Preparation 42

N-(3,4,5-Trimethoxyphenyl)-3-(5-methyl(tetrahydropyran-2-yl)-3-(2-chloro-6-fluoro-phenyl)isoxazol-4-oyl)aminophenyl Acetamide

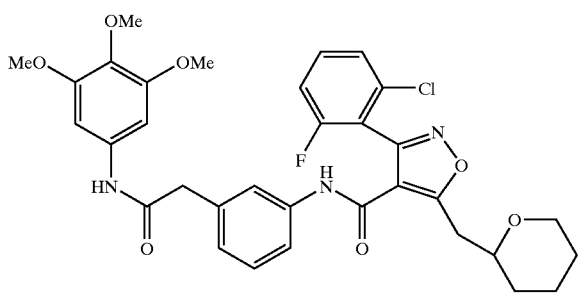

A mixture of 4-methoxycarbonyl-5-methyl(tetrahydropyran-2-yl)-3-(2-chloro-6-fluoro-phenyl)isoxazole (2.95 g, 7.98 mmol), 2N NaOH (8.0 ml, 16.0 mmol), MeOH (20 ml), and THF (10 ml) was heated to 55° C. for 4 h. After cooling to 0° C., HCl (1N) was added until pH 3. The mixture was extracted with ethyl acetate (3×), and the combined extracts were washed (brine), dried (MgSO$_4$), filtered, and concentrated to give the crude acid. The crude acid was dissolved in dichloromethane (50 ml) along with 2-(3-aminophenyl)-N-(3,4,5-trimethoxyphenyl)acetamide (3.80 g, 12.0 mmol), EDCI (3.33 g, 17.4 mmol), HOAt (2.72 g, 20.00 mmol), and DMAP (0.10 g, 0.80 mmol) and stirred at room temperature overnight. The mixture was applied to a silica gel column and eluted with dichloromethane/acetone (gradient) to give the title compound (2.61 g, 41%).

$^1$H NMR (400 MHz, CDCl$_3$) δ 9.39 (s, 1H), 7.61 (s, 1H), 7.39–7.24 (m, 4H), 7.09–7.04 (m, 2H), 6.69 (s, 2H), 5.00 (AB, 2H, J=14.2 Hz), 4.87 (app t, 1H, J=3.0 Hz), 3.75 (s, 6H), 3.73 (s, 3H), 3.68 (m, 1H), 3.61 (s, 2H), 3.55 (m, 1H), 1.80–1.40 (m, 6H)ppm. MS (ES) (m/z) 652.3 [M–1].

Preparation 43

2-Iodo-6-fluorobenzaldehyde

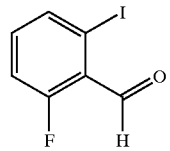

To a solution of diisopropylamine (6.94 ml, 49.5 mmol, 1.1 eq.) in THF (90 ml) under N$_2$, stirring at 0–5° C., was added dropwise over 10 minutes n-BuLi (28.12 ml, 45 mmol) and stirred at this temperature for 10 min. The reaction mixture was cooled to −78° C. in a dry ice/acetone bath and 1-iodo-5-fluorophenyl (5.29 ml, 45 mmol) was added dropwise over 5 min. The reaction was stirred at this temperature for 1 h, then dropwise DMF (4.15 ml, 49.5 ml, 1.1 eq.) was added over 5 minutes, and stirred for 10 minutes. Acetic acid (9 ml) was added, followed by H$_2$O, and extracted with Et$_2$O. The combined organic solution was washed with 0.1 N HCl, brine, dried (MgSO$_4$), filtered and concentrated. The crude 2-iodo-6-fluorobenzaldehyde (9.65 g) was taken onto the next step without purification. $^1$H NMR (400 MHz, CDCl$_3$) δ 10.13 (s, 1H), 7.80 (d, 1H), 7.31–7.21 (m, 2H).

GC[100 C (5 min.)→180 C (5 min.) @ 20 C/min], Rt=8.067.

Preparation 44

2-Iodo-6-fluorobenzaldehyde Oxime

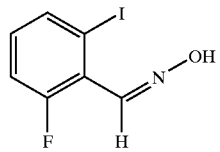

To a mixture of 2-iodo-6-fluorobenzaldehyde (45 mmol) in H$_2$O (22.5 ml), EtOH (22.5 ml), and ice (20 g) was added hydroxylamine hydrochloride (3.19 g, 49.5 mmol, 1.1 eq.). Then, 112.5 mmol of 50% NaOH (4.5 g in 4.5 ml H$_2$O, 2.5 eq.) was added with stirring. Enough ice to keep the temperature at 25–30° C. was added. The reaction was stirred for 2 h, acidified with conc. HCl to pH 4 (ice was added to keep the temperature at 25–30° C.), and extracted with Et$_2$O. The combined organic solution was washed with brine, dried (MgSO$_4$), filtered, and concentrated. The residue was chromatographed on silica gel using ethyl acetate in hexanes (5%–10%) to give 2-iodo-6-fluorobenzaldehyde oxime (7.06 g, 59% over 2 steps) as an oil that solidified over time.

¹H NMR (400 MHz, CDCl₃) δ 8.67 (br s, 1H), 8.29 (s, 1H), 7.71 (d, 1H) 7.14 (t, 1H), 7.06–7.01 (m, 1H). MS (ES) (m/z) 265.9 [M+1].

Preparation 45

2-Iodo-6-fluorobenzoyl Chloride Oxime

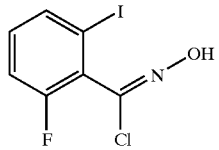

To a stirred solution of 2-iodo-6-fluorobenzaldehyde oxime (7.06 g, 26.6 mmol) in DMF (40 ml) at 25–30° C. was added about ⅕ of 26.6 mmol (3.56 g) of NCS. The initial NCS addition results in a slight temperature decrease. If the reaction does not self-initiate within 10 min., as indicated by a slight temperature rise, 5 pipette volumes of gas from the headspace of a conc. HCl reagent bottle is bubbled into the DMF solution. Careful addition of the rest of the NCS led to a temperature increase of 45–55° C. Once the reaction cools to R.T. (about 1 h), ice H₂O was added and the mixture was extracted with Et₂O. The combined organic solution was washed with brine, dried (MgSO₄), filtered, and concentrated. The crude 2-iodo-6-fluorobenzoyl chloride oxime (8.1 g) was taken on to the next step without purification.

¹H NMR (400 MHz, CDCl₃) δ 8.34 (s, 1H), 7.68 (d, 1H), 7.16–7.12 (m, 2H). IR (KBr) 3573.39, 3313.25, 1596.58, 1560.15, 1455.53, 1441.90, 1250.77, 979.18, 956.22, 889.04, 820.56 cm⁻¹.

Preparation 46

4-Ethoxycarbonyl-5-methyl-3-(2-iodo-6-fluoro-phenyl)isoxazole

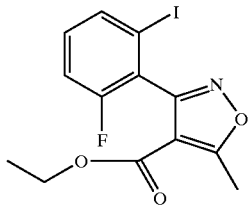

To a solution of 2-iodo-6-fluorobenzoyl chloride oxime (26.6 mmol) and ethyl-2-butynoate (3.72 ml, 31.92 ml, 1.2 eq.) in Et₂O (106 ml) under N₂, stirring at 0–5° C. added dropwise a solution of Et₃N (4.81 ml, 34.6 mmol, 1.3 eq) in Et₂O (13 ml) over 1 h. The reaction was allowed to warm to room temperature and stirred overnight. Et₂O was added and then washed with H₂O, brine, dried (MgSO₄), filtered, and concentrated. The crude residue was chromatographed on silica gel using ethyl acetate in hexanes (1–20%) to give the title compound (8.21 g, 82%).

¹H NMR (400 MHz, CDCl₃) δ 7.71 (d, 1H), 7.17–7.13 (m, 2H), 4.16 (q, 2H), 2.78 (s, 3H), 1.05 (t, 3H). IR (KBr) 1719.58, 1610.33, 1565.58, 1445.69, 1309.24, 1250.19, 1130.60, 1104.46, 858.18 cm⁻¹.

Preparation 47

4-Carboxy-5-methyl-3-(2-iodo-6-fluoro-phenyl)isoxazole

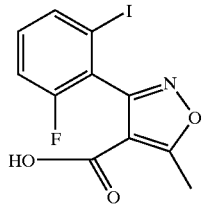

To a solution of 4-ethoxycarbonyl-5-methyl-3-(2-iodo-6-fluoro-phenyl)isoxazole (7.15 g, 19 mmol) in EtOH (100 ml) was added 5N NaOH (7.6 ml, 38 mmol, 2 eq.), and stirred in a 50° C. oil bath for 4 hrs. The reaction was cooled to room temperature, poured into ice H₂O and extracted with Et₂O. The aqueous layer was then acidified to pH 3 using conc. HCl and extracted with ethyl acetate. The organic solution was washed with brine, dried (MgSO₄), filtered, and concentrated to give the title compound (6.08 g, 92%).

¹H NMR (400 MHz, CDCl₃) δ 7.71 (d, 1H), 7.17–7.16 (m, 2H), 2.79 (s, 3H). IR (KBr) 1698.15, 1606.56, 1567.35, 1446.24, 1250.53, 858.75 cm⁻¹.

Preparation 48

N-(3,4,5-Trimethoxyphenyl)-3-(5-methyl-3-(2-iodo-6-fluoro-phenyl)isoxazol-4-oyl)aminophenyl Acetamide

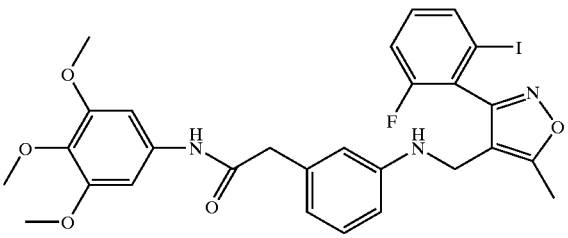

To a solution of 4-carboxy-5-methyl-3-(2-iodo-6-fluoro-phenyl)isoxazole (1.75 g, 5 mmol) in dichloromethane (30 ml) and THF (1 ml) was added oxalyl chloride (0.88 ml, 10 mmol, 2 eq.) under N₂, then DMF (3 drops) to initiate the reaction. The reaction was stirred for 2 h, concentrated, and re-dissolved in dichloromethane (50 ml) under N₂. A solution of 2-(3-aminophenyl)-N-(3,4,5-trimethoxyphenyl) acetamide (1.59, 5 mmol) in THF (14 ml) was added, cooled to 0° C., and then added triethylamine (0.7 ml, 5 mmol), and stirred for 17 h. Crude reaction was partitioned between ethyl acetate and 1N HCl. The organic layer was washed with H₂O and brine, dried (MgSO₄), filtered and concentrated. The crude material was titrated with diethyl ether (3×) and purified by flash chromatography (silica gel) using 1–10% acetone in dichloromethane to give the title compound (1.67 g, 51%).

MS (ES) (m/z) 646.19 [M+1]. IR (KBr) 1706.18, 1666.12, 1608.97, 1561.18, 1548.78, 1507.10, 1491.46, 1451.15, 1409.43, 1243.72, 1225.47, 1214.50, 1177.72, 1129.46, 854.90, 779.41 cm⁻¹.

Preparation 49

2-Fluoro-5-iodobenzaldehyde

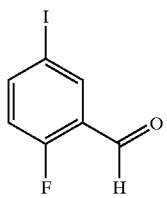

To a solution of diisopropylamine (1.54 ml, 11 mmol, 1.1 eq.) in THF (20 ml) under $N_2$ stirring at 0–5° C. was added dropwise over 10 minutes 1.6M n-BuLi (6.25 ml, 10 mmol) and stirred at this temperature for 10 min. The reaction mixture was cooled to –78° C. in a dry ice/acetone bath and dropwise added 1-iodo-4-fluorophenyl (1.12 ml, 10 mmol) over 5 min. The reaction was stirred at this temperature for 1 h, and DMF (0.8 ml, 11 mmol, 1.1 eq.) was added dropwise over 5 minutes, and stirred for 10 minutes. Acetic acid (2 ml) was added, followed by $H_2O$ and extracted with $Et_2O$. The combined organic solution was washed with 0.1 N HCl, brine, dried (MgSO$_4$), filtered and concentrated. The crude 2-fluoro-5-iodobenzaldehyde (2.36 g) was taken onto the next step without purification.

$^1$H NMR (400 MHz, CDCl$_3$) δ 10.26 (s, 1H), 8.14 (d, 1H), 7.89–7.86 (m, 1H), 6.95 (t, 1H). GC[100 C (5 min.)→180 C (5 min.) @ 20 C/min], Rt=7.375.

Preparation 50

2-Fluoro-5-iodobenzaldehyde Oxime

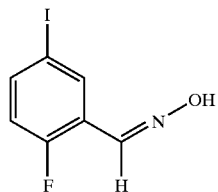

To a mixture of 2-fluoro-5-iodobenzaldehyde (9.4 mmol) in $H_2O$ (5 ml), EtOH (5 ml), and ice (4.5 g) was added hydroxylamine hydrochloride (0.67 g, 10.3 mmol, 1.1 eq.). Then, 23.6 mmol of 50% NaOH (1 g in 1 ml $H_2O$, 2.5 eq.) was added with stirring. Enough ice to keep the temperature at 25–30° C. was added. The reaction was stirred for 2 h, acidified with conc. HCl to pH 4 (ice was added to keep the temperature at 25–30° C.), and extracted with $Et_2O$. The combined organic solution was washed with brine, dried (MgSO$_4$), filtered, and concentrated. The residue was chromatographed on silica gel using (1–10%) ethyl acetate in hexanes to give 2-fluoro-5-iodobenzaldehyde oxime (2.06 g, 78% over 2 steps).

MS (ES) (m/z) 264.0 [M–1]. IR (KBr) 3575.39, 1478.30, 1262.00, 1238.75, 1109.23, 964.08, 810.03, 809.87 cm$^{-1}$.

Preparation 51

2-Fluoro-5-iodobenzoyl Chloride Oxime

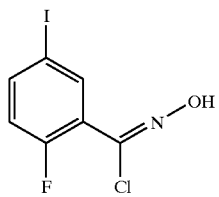

To a stirred solution of 2-fluoro-5-iodobenzaldehyde oxime (2.06 g, 7.77 mmol) in DMF (10 ml) at 25–30° C. was added about ⅕ of 7.77 mmol (1.04 g) of NCS. The initial NCS addition results in a slight temperature decrease. If the reaction does not self-initiate within 10 min., as indicated by a slight temperature rise, 5 pipette volumes of gas from the headspace of a conc. HCl reagent bottle is bubbled into the DMF solution. The rest of the NCS was carefully added, and the temperature rose to 35–40° C. Once the reaction cooled to R.T. (about 2 h), ice $H_2O$ was added and the crude was extracted with $Et_2O$. The combined organic solution was washed with brine, dried (MgSO$_4$), filtered, and concentrated. The crude product 2-fluoro-5-iodobenzoyl chloride oxime (2.24 g) was taken on to the next step without purification.

MS (FD) (m/z) 298.9. IR (KBr) 3553.03, 3258.13, 1601.51, 1484.38, 1396.69, 1266.05, 1241.83, 1122.00, 1000.66, 954.27, 820.20 cm$^{-1}$.

Preparation 52

4-Ethoxycarbonyl-5-methyl-3-(2-fluoro-5-iodophenyl)isoxazole

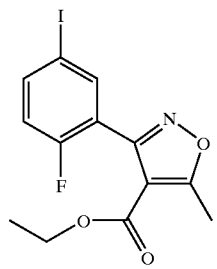

To a solution of 2-fluoro-5-iodobenzoyl chloride oxime (2.24 g, 7.48 mmol) and ethyl-2-butynoate (1.74 ml, 14.96 mmol, 2 eq.) in $Et_2O$ (28 ml) under $N_2$ stirring at 0–5° C., was added dropwise a solution of $Et_3N$ (1.35 ml, 9.72 mmol, 1.3 eq) in $Et_2O$ (3.6 ml) over 1 h. Reaction was allowed to warm to room temperature and stirred overnight. It was then partitioned between $Et_2O$ and $H_2O$, washed with brine, dried (MgSO$_4$), filtered, and concentrated. The crude residue was chromatographed on silica gel using (1–10%) ethyl acetate in hexanes to give the title compound (2.06 g, 73%).

MS (ES) (m/z) 376.2 [M+1]. IR (KBr) 1719.10, 1606.15, 1454.85, 1311.13, 1261.44, 1233.84, 1122.63, 1099.04, 819.26 cm$^{-1}$.

Preparation 53

4-Carboxy-5-methyl-3-(2-fluoro-5-iodophenyl)isoxazole

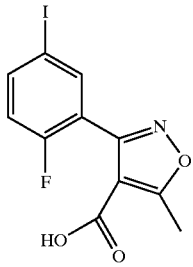

To a solution of 4-ethoxycarbonyl-5-methyl-3-(2-fluoro-5-iodophenyl)isoxazole (1.04 g, 2.77 mmol) in EtOH (14 ml) was added 5N NaOH (1.11 ml, 5.6 mmol, 2 eq.) and stirred in a 50° C. oil bath for 1 hr. Rxn was cooled to room temperature, poured into ice $H_2O$ and extracted with $Et_2O$. Acidified aqueous layer to pH 2 using conc. HCl and extracted with ethyl acetate. The combined organic solution was washed with brine, dried ($MgSO_4$), filtered, and concentrated to give the title compound (0.85 g, 86%).

MS (ES) (m/z) 348.0 [M+1]. (KBr) 1698.84, 1602.67, 1465.80, 1261.94, 1234.74, 819.32 cm$^{-1}$.

Preparation 54

N-(3,4,5-Trimethoxyphenyl)-3-(5-methyl-3-(2-fluoro-5-iodo-phenyl)isoxazol-4-oyl)aminophenyl Acetamide

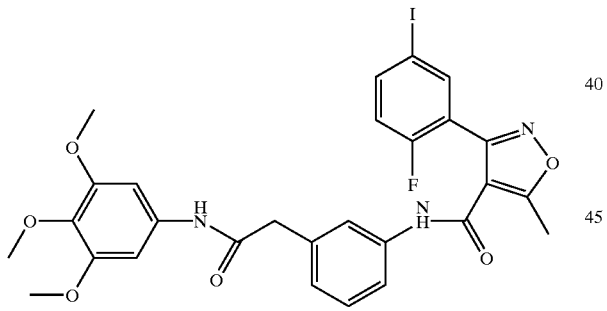

To a solution of 4-carboxy-5-methyl-3-(2-fluoro-5-iodophenyl)isoxazole (0.85 g, 2.45 mmol) in dichloromethane (15 ml) was added oxalyl chloride (0.5 ml, 4.9 mmol, 2 eq.) under $N_2$, then DMF (3 drops) to catalyze the reaction. Reaction was stirred for 1 h, concentrated, and dissolved in dichloromethane (25 ml) under $N_2$. 2-(3-aminophenyl)-N-(3,4,5-trimethoxyphenyl)acetamide was added (0.77 g, 2.45 mmol), reaction cooled to 0° C., added triethylamine (0.33 ml, 2.45 mmol), and then stirred for 2 h 30 min. Crude was partitioned between ethyl acetate and 1N HCl. Organic layer was washed with $H_2O$ and brine, dried ($MgSO_4$), filtered and concentrated. The crude material was triturated with $Et_2O$ (3×) to give the title compound (1.0 g, 63%).

MS (ES) (m/z) 646.4 [M+1]. IR (KBr) 1681.31, 1605.86, 1508.01, 1452.11, 1132.40 cm$^{-1}$.

Preparation 55

3-[9-chloro-3-mesylmethyl-isoxazolo[4,5-c]quinoline-4(5H)-one]-N-3,4,5-trimethoxyphenyl-benzene Acetamide

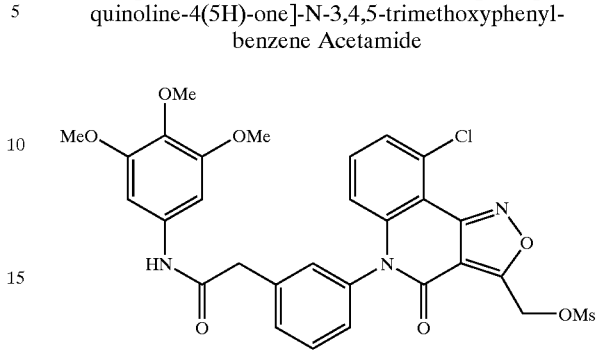

Under the conditions described for example 20, alcohol 3-[9-chloro-3-methoxy-isoxazolo[4,5-c]quinoline-4(5H)-one]-N-3,4,5-trimethoxyphenyl-benzene acetamide (226 mg, 0.41 mmol), methanesulfonyl chloride (0.16 ml, 2.1 mmol), triethyl amine (0.45 ml, 3.2 mmol), and dichloromethane (6 ml) gave the crude title compound (241 mg, 94%) which was used without further purification.

Preparation 56

4-Methoxycarbonyl-5-(2-chloro-6-fluorophenyl)oxazole

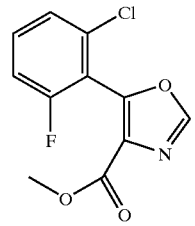

To a solution of 2-chloro-6-fluorobenzoic acid (2.14 g, 12.3 mmol), $CH_2Cl_2$ (50 ml), and DMF (2 drops) at room temperature under $N_2$ was added oxalyl chloride (9.2 ml, 18.4 mmol) dropwise. The mixture was stirred for 3 h and the volatiles were removed under reduced pressure to give the crude acid chloride. The crude acid chloride and methyl isocyanoacetate (1.23 g, 12.3 mmol) were dissolved in THF (20 ml) at room temperature under $N_2$ and $Et_3N$ (6.8 ml, 49.2 mmol) was added dropwise over a period of 30 minutes. The reaction was allowed to stir for 22 h followed by dilution with $Et_2O$, extraction with $H_2O$, 1N HCl, $H_2O$, brine, dried ($MgSO_4$), filtered, and concentrated. Column chromatography (silica gel, hexanes/$Et_2O$ gradient) gave 4-methoxycarbonyl-5-(2-chloro-6-fluorophenyl)oxazole (0.74 g, 24%).

$^1$H NMR (400 MHz, $CDCl_3$) d 8.01 (s, 1H), 7.41 (dt, 1H, J=5.9, 8.3 Hz), 7.29 (ap d, 1H, J=8.3 Hz), 7.09 (ap t, 1H, J=8.3 Hz), 3.81 (s, 3H)ppm.

Preparation 57

N-(3,4,5-trimethoxyphenyl)-3-(5-(2-chloro-6-fluoro-phenyl)oxazol-4-oyl)aminophenyl Acetamide

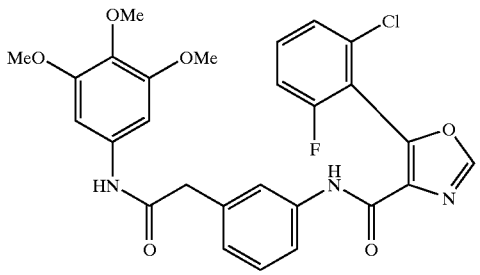

A mixture of 4-methoxycarbonyl-5-(2-chloro-6-fluorophenyl)oxazole (236 mg, 0.927 mmol), MeOH (5 ml), THF (1 ml), and 2N NaOH (1.5 ml, 3.00 mmol) was heated to 50° C. for 30 minutes. The mixture was cooled to room temperature and $H_2O$ and ice were added followed by acidification to pH 2 and extraction with EtOAc. The organic fraction was washed (brine), dried ($Na_2SO_4$), filtered, and concentrated to give the crude carboxylic acid. The crude carboxylic acid, 2-(3-aminophenyl)-N-(3,4,5-trimethoxyphenyl)acetamide (292 mg, 0.927 mmol), EDCI (354 mg, 1.85 mmol), and DMAP (11 mg, 0.093 mmol) were allowed to react in $CH_2Cl_2$ (5 ml) for 15 h at room temperature under $N_2$. The mixture was applied directly to a silica gel column and elution with hexanes/EtOAc (gradient) gave the title compound (193 mg, 39%).

$^1$H NMR (400 MHz, $CDCl_3$) d 8.88 (s, 1H), 8.02 (s, 1H), 7.72 (s, 1H), 7.48 (d, 1H, J=8.3 Hz), 7.40 (dt, 1H, J=5.9,7.3 Hz), 7.33–7.28 (m, 2H), 7.12–7.03 (m, 2H), 6.68 (s, 2H), 3.75 (s, 6H), 3.74 (s, 3H), 3.64 (s, 2H)ppm. Mass spectrum (ES) (m/z) 540.1 [M+1].

Preparation 58

3-(2-Chloro-6-fluoro-phenyl)-5-methyl-4H-pyrazole-4-carboxylic Acid Ethyl Ester

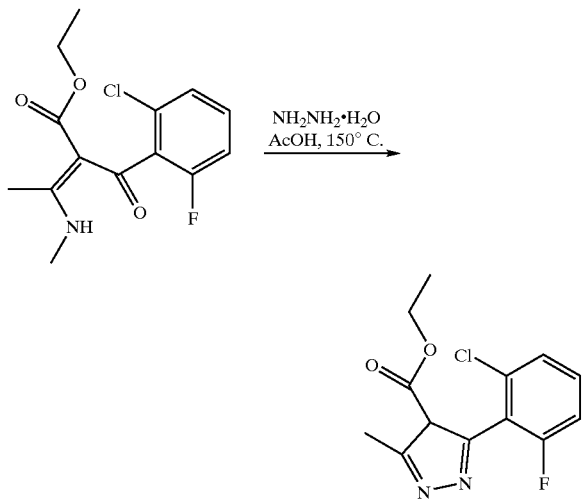

2-(2-Chloro-6-fluoro-benzoyl)-3-methylamino-but-2-enoic acid ethyl ester (500 mg, 1.6 mmol) was taken in acetic acid (10 mL) and was treated with hydrazine hydrate at 150° C. overnight. Acetic acid is removed under reduced pressure and the residue was dissolved in ethyl acetate (20 mL) and washed with water, (2×10 mL), brine (2×10 mL), dried over sodium sulfate, filtered and evaporated to yield the title compound (588 mg, crude).

MS (ES): 283 (M)$^+$, 284 (M+1)$^+$, 281 (M−1)$^−$. H NMR ($CDCl_3$): 1.03–1.06 (t, 3H), 2.55 (s, 3H), 7.03–7.07 (t, 1H), 7.21–7.35 (m, 2H).

Preparation 59

Methyl-2-(formylamino)-3-(2-chloro-6-fluorophenyl)acrylate

NaH (60% in oil, 2.4 g, 0.06 mol, approx. 1.2 eq) was placed in a dry 50 ml flask and heated to 35 degrees. To it was slowly added 50 ml of a THF solution containing 2-chloro-6-fluorobenzaldehyde (7.93 g, 0.05 mol) and methyl isocyanoacetate (5 g, 0.05 mol). The reaction was then cooled to RT, and stirred for 3 hr. At that time, 10 ml of 10% HOAc was added. After 10 min, the contents were concentrated in vacuo to a dark brown oil, then diluted with $CHCl_3$, and transferred to a sep funnel. The aqueous phase was reextracted (3×) with $CHCl_3$, and the combined extracts were washed with brine, dried over $Na_2SO_4$, filtered, and concentrated to crude product. Purification over a pad of silica gel was accomplished by elution with 10:1 $CHCl_3$/EtOAc to afford the title compound, clean Z/E olefins (1:1 mix, 8.24 g, 64%).

NMR ($CDCl_3$) δ 8.48 (s, vinyl H), 8.09 (s, vinyl H), 7.8 (brd s, HCO), 7.1 (m), 7.0 (m), 3.65 (s, E-$CH_3$), 3.6 (Z-$CH_3$). MS (+ES) 257.9/259.9 (M+H)+.

Preparation 60

Methyl-2-(formylamino)-3-bromo-3-(2-chloro-6-fluorophenyl)acrylate

To the chilled (0°) olefin mixture (3.723 g, 14.5 mmol) in $CCl_4$ (40 ml) was added N-bromosuccinimide (3.874 g, 21.8 mmol) slowly over a 5 min period. After 4 hr, the reaction was complete, and $Et_3N$ (1.52 g, 15 mmol) was added dropwise with vigorous stirring. The resulting mixture was diluted with EtOAc (250 ml, total) and transferred to a separatory funnel. The organic phase was washed with saturated aqueous bicarbonate, then brine, and dried over Na2SO4. Following filtration and concentration, the crude product (predominantly Z olefin) was obtained, and purified by filtration over a pad of silica gel (2:1 hex/EtOAc) to afford the title compound (2.4 g, 50%).

NMR ($CDCl_3$) δ 8.25 (brd s, HCO), 7.1–7.2 (m), 6.98 (app t), 3.5 (s, $CH_3$). MS (−ES) 333.8/335.8 (M−H)−.

Preparation 61

Z-Methyl-2-isocyano-3-bromo-3-(2-chlorofluorophenyl)acrylate

To the olefin (1.2 g, 3.58 mmol) and $Et_3N$ (0.896 g, 8.96 mmol) in 10 ml MeCl2 chilled to −20° was added $POCl_3$ (0.37 ml, 3.94 mmol) dropwise. The reaction mixture was then warmed to 0°, and stirred for 3.5 hr. At that time, the reaction was poured into a separatory funnel containing 20% aq. $K_2CO_3$ (50 ml) and $MeCl_2$ (50 ml). The basic aqueous solution was then washed with additional organic solvent, and the combined extracts were washed with brine, dried over $Na_2SO_4$, filtered, and concentrated to afford crude product. Purification (silica gel chrom., $MeCl_2$) afforded clean isonitrile (0.325 g, 45%).

NMR (CDCl$_3$) δ 7.0–7.3 (3 m), 3.72 (s, CH$_3$). IR (CHCl$_3$) 2117 cm$^{-1}$.

EXAMPLES

Example 1

N-(3,4,5-Trimethoxyphenyl) 3-(5-Chloroisoxazol[3,4-c]-1,2-dihydro-6-chloroquinolin-2-on-1-yl)phenylacetamide

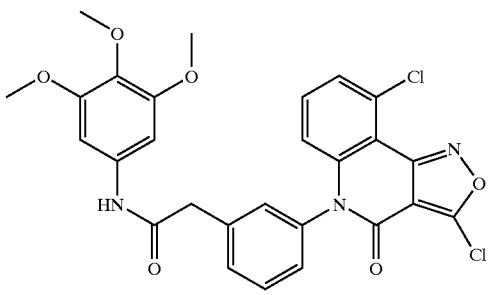

To a solution of N-[3,4,5-trimethoxyphenyl)-3-(3-(2-chloro-5-fluorophenyl)-5-chloroisoxazoloyl)aminophenyl-acetamide (100 mg, 0.1742 mmol) in DMF (40 mL) was added potassium carbonate (70 mg, 0.522 mmol) at 0° C. The mixture was stirred at −10° C. for three hours. The solution was allowed to warm to room temperature and stirred for three more hours. The reaction mixture was diluted with ethyl acetate (50 mL) and washed with 1N HCl (100, 80, 40 mL), dried and concentrated in vacuo to give crude product which was further purified by flash chromatography (silica gel) (gradient: hexanes/ethyl acetate) to give product as a white solid (30 mg, 31.1%); Rf=0.68 (ethyl acetate/hexane, 7/3).

$^1$H NMR (CDCl$_3$, 300 MHz) δ; 10.18 (s, 1H, NH), 7.38–7.69 (m, ArH$_7$), 6.95 (s, ArH$_2$); 3.68 (s, 6H, 2OCH$_3$), 3.67 (s, 2H, CH$_2$), 3.58 (s, 3H, OCH$_3$)ppm.

Example 2

N-(3,4,5-Trimethoxyphenyl)-3-(5-morpholin-4-ylisoxazolo[3,4-c]-1,2-dihydro-6-chloroquinolin-2-on-1-yl)phenylacetamide

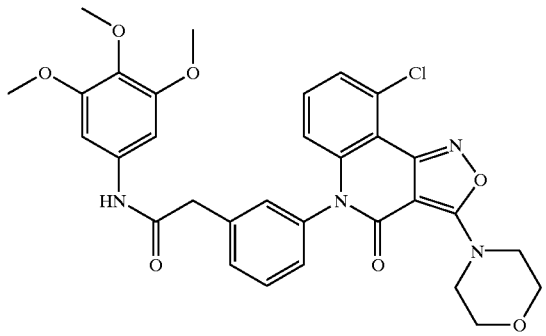

To a solution of N-(3,4,5-trimethoxyphenyl) 3-(3-(2-chloro-5-fluorophenyl)-5-morpholino)isoxazol-4-oyl)aminophenyl acetamide (140 mg, 0.224 mmol) in DMF (6.9 mL) was added potassium carbonate (247.5 mg, 1.79 mmol). The mixture was stirred at room temperature for four hours and then diluted with ethyl acetate (20 mL), washed with water (6 mL×3), dried over MgSO$_4$ and concentrated to give crude product, which was further purified by flash chromatography to give product as a white solid (131 mg, 97%).

IR (CHCl$_3$) υ$_{max}$ 3010, 1663, 1601, 1594, 1497, 1451, 1412, 1263, 1132 cm$^{-1}$; UV (EtOH) λ$_{max}$ 298 (ε=16442), 289 (ε=15852), 256 (ε=34088), 249 (ε=31992), 215 (ε=51994)nm. MS (ES) m/z 605.3 (M$^+$, 100); Anal. Calcd. for C$_{31}$H$_{29}$N$_4$O$_7$Cl; Requires: C, 61.54; H, 4.83; N, 9.26; Found: C, 61.55; H, 5.09; N, 9.14%.

Example 3

N-(3,4,5-Trimethoxyphenyl)-3-(1-t-butyl-pyrazolo[3,4-c]-1,2-dihydro-6-chloroquinolin-2-on-1-yl)phenylacetamide

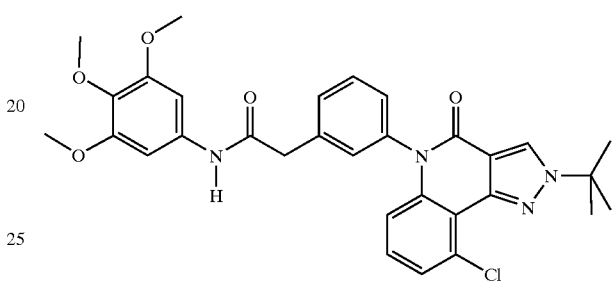

To a solution of N-(3,4,5-trimethoxyphenyl) 3-(1-(tert-butyl)-3-(2-chloro-5-fluoro-phenyl)pyrazol-4-oyl) aminophenyl acetamide (595 mg, 1 mmol) in DMF (10 mL) powdered potassium carbonate (500 mg) was added and stirred at 100° C. overnight. The reaction mixture was diluted with ethyl acetate (200 ml) and washed with water (3×100 ml), brine, dried over sodium sulfate, evaporated and chromatographed (silica column, 50% ethyl acetate in chloroform). Yield 500 mg, 86%.

NMR (CDCl$_3$): δ 1.70 (s, 9H, t-Bu), 3.78 (s, 2H, CH$_2$), 3.80 (s, 6H, 2 OMe), 3.81 (s, 3H, OMe), 6.59 (d, 1H, Ar), 6.91 (s, 2H, (OMe)$_3$Ar), 7.09 (t, 1H, Ar), 7.19 (d, 2H, Ar), 7.28 (t, 1H, Ar), 7.40 (d, 1H, Ar), 7.52 (t, 1H, Ar), 8.25 (s, 1H, pyr). MS (ES): 575 (M), 576 (M+1), 593 (M+18), MS (ES): 634 (M+59).

Example 4

N-(3,4,5-Trimethoxyphenyl)-3-(pyrazolo[3,4-c]-1,2-dihydro-6-chloroquinolin-2-on-1-yl)phenylacetamide

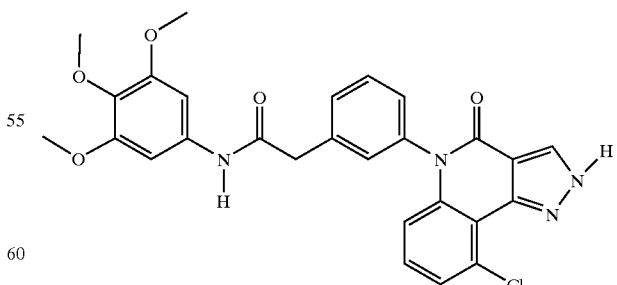

A solution of N-(3,4,5-trimethoxyphenyl)-3-(1-t-Butyl-pyrazolo[3,4-c]-1,2-dihydro-6-chloroquinolin-2-on-1-yl)phenylacetamide (46 mg, 0.8 mmol) in TFA reagent (2.5% anisole, 2.5% triisopropyl silane, 2.5% water and 92.5%

TFA, 2 mL) was refluxed overnight. The reaction mixture was evaporated and azeotroped with toluene, and the residue was chromatographed (silica column, ethyl acetate). Yield 40 mg, 100%.

NMR (CDCl₃): δ 3.70 (s, 2H, CH₂), 3.80 (s, 3H, OMe), 3.82 (s, 6H, 2OMe), 6.79 (d, 1H, Ar), 6.91 (s, 2H, (OMe)₃Ar), 7.20–7.30 (m, 2H, Ar), 7.39 (d, 1H, Ar), 7.49 (d, 1H, Ar), 7.60 (t, 1H, Ar), 7.89 (s, 1H, Ar), 8.29 (s, 1H, pyr). DMSOd-6 (80° C.): δ 3.60 (s, 3H, OMe), 3.72 (s, 6H, 2OMe), 3.72, 2H, CH₂), 6.56 (d, 1H, Ar, adjacent to chloro), 7.25 (d, 1H, Ar), 7.28 (s, 1H, Ar), 7.37 (t, 1H, Ar), 7.42 (d, 1H, Ar), 7.52 (d, 1H, Ar), 7.59 (t, 1H, Ar), 8.41 (s, 1H, pyr), 10.16 (s, 1H, NH), 14.10 (br s, 1H, NH); ¹³C NMR (DMSOd-6, 80° C.): δ 42.8, 55.6, 60.0, 96.7, 115.8, 123.7, 127.7, 129.3, 129.7, 130.0, 130.0, 133.5, 134.6, 135.2, 137.9, 138.0, 141.6, 152.7, 168.1, 168.5, MS (ES): 519 (M), 520 (M+1), 537 (M+18); MS (ES): 517 (M–2), 518 (M–1), 519 (M).

Example 5

N-Methyl-N-3,4,5-trimethoxyphenyl-3-(1-t-butyl-pyrazolo[3,4-c]-1,2-dihydro-6-chloroquinolin-2-on-1-yl)phenylacetamide

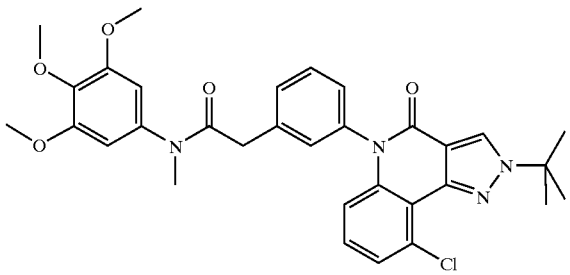

To a suspension of NaH (30 mg, 0.6 mmol, 60% oil dispersion) in DMF (5 mL) a solution of N-(3,4,5-trimethoxyphenyl)-3-(1-t-butyl-pyrazolo[3,4-c]-1,2-dihydro-6-chloroquinolin-2-on-1-yl)phenylacetamide (180 mg, 0.31 mmol) in DMF (10 mL) was added and heated at 100° C. for 30 min and cooled to room temperature. Then methyl iodide (84 mg, 0.6 mmol) was added and the reaction was stirred overnight. The reaction mixture was diluted with ethylacetate (100 mL), and quenched with water. The ethyl acetate solution was washed with water, brine, dried over sodium sulfate, filtered, evaporated and the residue was chromatographed (silica column, ethyl acetate). Yield 50 mg, 27%.

NMR (CDCl₃): δ 1.75 (s, 9H, t-But), 3.22 (s, 3H, N-Me), 3.70 (s, 6H, 2OMe). 3.80 (s, 5H, OMe and CH₂), 6.30 (s, 2H, (OMe)₃Ar), 6.55 (d, 1H, Ar), 7.09 (s, 1H, Ar), 7.10 (s, 1H, Ar), 7.11 (s, 1H, Ar), 7.18 (d, 1H, Ar), 7.25 (d, 1H, Ar), 7.22 (1H, Ar), 7.42 (t, 1H, Ar), 8.40 (s, 1H, Pyr). MS (ES): 589 (M), 590 (M+1), 607 (M+18).

Example 6

N-Methyl-N-3,4,5-trimethoxyphenyl-3-(pyrazolo[3,4-c]-1,2-dihydro-6-chloroquinolin-2-on-1-yl)phenylacetamide

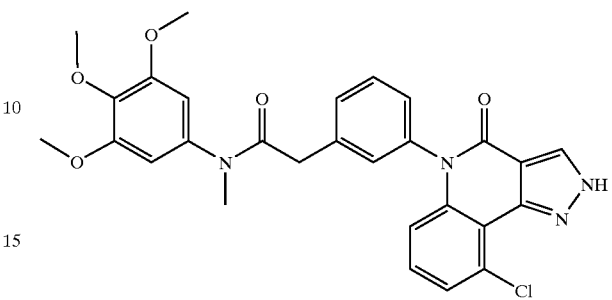

A solution of N-methyl-N-3,4,5-trimethoxyphenyl-3-(1-t-butyl-pyrazolo[3,4]-1,2-dihydro-6-chloroquinolin-2-on-1-yl)phenylacetamide in TFA reagent (2.5% anisole, 2.5% triisopropyl silane, 2.5% water and 92.5% TFA, 3 mL) was refluxed for 4 hours. The reaction mixture was evaporated and the residue was azeotroped with toluene and triturated with hexane to yield a white solid. The solid was dissolved in chloroform and filtered through a cation exchange column (6 cc, Varian Bond Elute, SCX) and eluted with methanol. Methanolic fractions containing the product were evaporated. Yield 35 mg, 83%.

NMR (CD₃OD): δ 3.22 (s, 3H, N-Me), 3.64 (s, 2H), 3.70 (s, 6H, 2OMe), 3.71 (s, 3H, OMe), 6.25 (s, 2H, (OMe)₃Ar), 6.62 (d, 1H, Ar), 7.08 (d, 1H, Ar), 7.06 (s, 1H, Ar), 7.14 (d, 1H, Ar), 7.21 (d, 1H, Ar), 7.31–7.36 (m, 1H, Ar), 7.49 (t, 1H, Ar), 8.65 (s, 1H, pyr), 7.70–7.75 (m, 1H, Ar), 11.60 (br s, pyr-NH). MS (ES)+: 533 (M), 551 (M+18).

Example 7

N-Methyl-N-3,4,5-trimethoxyphenyl-3-(1-methyl-pyrazolo[3,4-c]-1,2-dihydro-6-chloroquinolin-2-on-1-yl)phenylacetamide

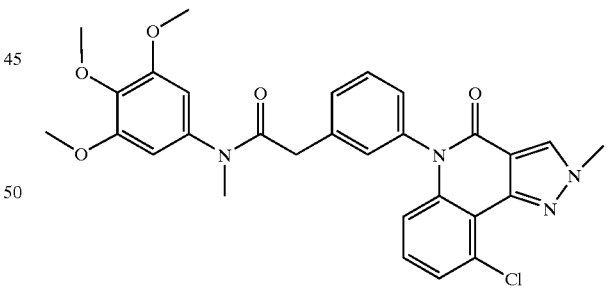

To a suspension of sodium hydride (0.15 mmol, 6 mg, 60% dispersion) in DMF (5 mL), a solution of N-methyl-N-3,4,5-trimethoxyphenyl-3-(pyrazolo[3,4]-1,2-dihydro-6-chloroquinolin-2-on-1-yl)phenylacetamide (20 mg, 0.037 mmol) was added and stirred at room temperature for 4 hours, methyl iodide (1 mL, 3 mmol) was added, and the reaction was stirred for 3 hours. The reaction mixture was diluted with ethyl acetate and (100 mL) washed with water (2×50 mL), dilute HCl (2×50 mL), brine (2×50 mL), dried over sodium sulfate, filtered, evaporated and chromatographed (purified by silica TLC, 20×20 cm, 250 m thickness, 30% ethyl acetate in chloroform). Yield 3.5 mg, 17%.

NMR (CDCl$_3$): δ 3.25 (s, 3H, N-Me), 3.59 (s, 2H, CH$_2$), 3.73 (s, 6H, 2OMe), 3.83 (s, 3H, OMe), 4.22 (s, 3H, pyr-N-Me), 6.33 (s, 2H, (OMe)$_3$Ar), 6.59 (d, 1H, Ar), 7.10–7.17 (m, 2H, Ar), 7.21–7.31 (m, 3H, Ar), 7.46 (t, 1H, Ar), 8.23 (s, 1H, pyr). MS (ES)+: 547 (M), 548 (M+1), 549 (M+2).

Example 8

N-3,4,5-Trimethoxyphenyl-3-(1-methyl-pyrazolo[3,4-c]-1,2-dihydro-6-chloroquinolin-2-on-1-yl) phenylacetamide

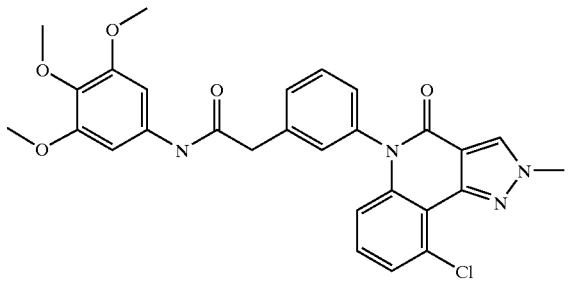

To a solution of N-3,4,5-trimethoxyphenyl-3-(pyrazolo[3,4-c]-1,2-dihydro-6-chloroquinolin-2-on-1-yl)-phenylacetamide (100 mg, 0.19 mmol) in DMF (10 mL), cesium carbonate (100 mg, 0.3 mmol), was added and stirred for 3 h. At the end of three hours, methyl iodide (42 mg, 0.3 mmol) was added and reaction was stirred overnight. The reaction mixture was diluted with ethyl acetate and washed with water, brine, dried over sodium sulfate, filtered and evaporated. The residue was chromatographed (HPLC using Technikrom, 10 micron, silica column 50.8×250 mm, 5% methanol in 95% chloroform to 100% methanol, flow rate 75 mL/min). Yield 9 mg (9%) following unoptimized prep HPLC.

NMR (CD$_3$OD): δ 3.64 (s, 2H), 3.70 (s, 6H, 2OMe), 3.71 (s, 3H, OMe), 4.21 (s, 3H, N-me), 6.25 (s, 2H, (OMe)$_3$Ar), 6.62 (d, 1H, Ar), 6.95 (s, 1H, Ar), 7.08 (d, 1H, Ar), 7.14 (d, 1H, Ar), 7.18 (d, 1H, Ar), 7.20–7.30 (m, 1H, Ar), 7.38 (t, 1H, Ar), 7.50–7.65 (m, 1H, Ar), 8.50 (s, 1H, pyr). MS (ES): 533 (M+1).

Example 9

N-3,4,5-trimethoxyphenyl-3-[3-methyl-isoxazolo[4,5-c]-1,2-dihydro-6-chloroquinolin-2-on-1-yl] phenylacetamide

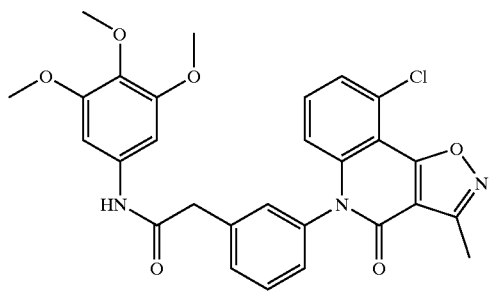

To N-(3,4,5-trimethoxyphenyl) 3-(3-methyl-5-(2-chloro-5-fluoro-phenyl)isoxazol-4-oyl)aminophenyl acetamide (20 mg, 0.036 mmol) in DMF (1 ml) was added finely powdered K$_2$CO$_3$ (200 mg, 1.4 mmol). The suspension was rapidly stirred at room temperature. Workup involved dilution with EtOAc and 1 N HCl, transfer to a separatory funnel, and extraction of the aqueous 3X (EtOAc). The combined organics were washed with saturated bicarbonate, brine, then dried. Filtration and concentration afforded the crude tricycle (16 mg). Purification (Bond-Elut silica cartridge, 0.5 g, 2:1 EtOAc/hexane) provided a pure sample (7.5 mg) of final product.

NMR (CDCl$_3$) δ 7.2, 7.3, 7.47, 7.6 (4 m, 6H), 6.8 (s, 2H), 6.65 (dd, 1H), 3.76, 3.78 (2s+m, 11H), 2.6 (s, 3H). MS (+ES) m/z 533.8 (M+H)$^+$, 550.8 (M+NH$_3$)$^+$.

Example 10

N-3,4,5-Trimethoxyphenyl-3-[3-methyl-isoxazolo[4,5-c]-1,2-dihydroquinolin-2-on-1-yl]phenylacetamide

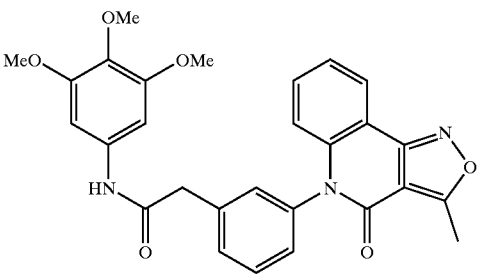

A solution from preparation 17 (0.27 g, 0.50 mmol), DMF (5.0 ml), and NaOH in MeOH (2.5 ml, 2N) was heated to 60° C. for 2 h then cooled to room temperature. EtOAc and H$_2$O were added and the layers separated. The organic fraction was washed (H$_2$O and brine), dried (MgSO$_4$), filtered, and concentrated. Column chromatography (silica gel, acetone/CH$_2$Cl$_2$) gave the title compound (0.19 g, 73%).

$^1$H NMR (400 MHz, CDCl$_3$) δ 8.22 (dd, 1H, J=1.4, 7.8 Hz), 7.61 (t, 1H, J=7.8 Hz), 7.35 (m, 2H), 7.27 (m, 2H), 6.82 (s, 2H), 6.64 (d, 1H, J=8.5 Hz), 3.82 (s, 3H), 3.79 (s, 3H), 3.78 (s, 3H), 3.76 (s, 2H), 2.86 (s, 3H)ppm. Anal. calc. for C$_{28}$H$_{25}$N$_3$O$_6$; C, 67.33%, H, 5.04%, N, 8.41%; found C, 67.25%, H, 5.27%, N, 8.30%. MS (FAB) (m/z) 500.3 [M+1].

Example 11

N-3,4,5-Trimethoxyphenyl-3-[3-phenyl-isoxazolo[4,5-c]-1,2-dihydro-6-chloroquinolin-2-on-1-yl] phenylacetamide

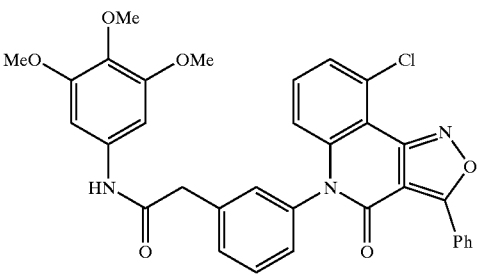

A mixture of the product from preparation 22 (0.160 g, 0.27 mmol), DMF (5 ml), and NaOH (2.5 ml, 2N in methanol) were reacted overnight. Dilution with ethyl acetate, washing (H$_2$O then brine), drying (MgSO$_4$), filtration and concentration gave the crude product. Purification by column chromatography (silica gel, hexanes/ethyl acetate gradient) afforded the title compound (0.102 g, 66%).

$^1$H NMR (400 MHz, CDCl$_3$) δ 8.46 (dd, 1H, J=1.0, 8.3 Hz), 7.60 (t, 1H, J=7.8 Hz), 7.51–7.42 (m, 5H), 7.34–7.21 (m, 5H), 6.74 (s, 2H), 6.55 (dd, 1H, J=1.0, 8.3 Hz), 3.74 (s, 6H), 3.72 (s, 5H)ppm. MS (FAB) (m/z) 595.4 [M+1].

Examples 12 and 13

N-3,4,5-Trimethoxyphenyl-3-[3-methyl-isoxazolo[4,5-c]-1,2-dihydro-6-fluoroquinolin-2-on-1-yl]phenylacetamide & N-3,4,5-Trimethoxyphenyl-3-[3-methyl-isoxazolo[4,5]-1,2-dihydro-6-methoxyquinolin-2-on-1-yl]phenylacetamide

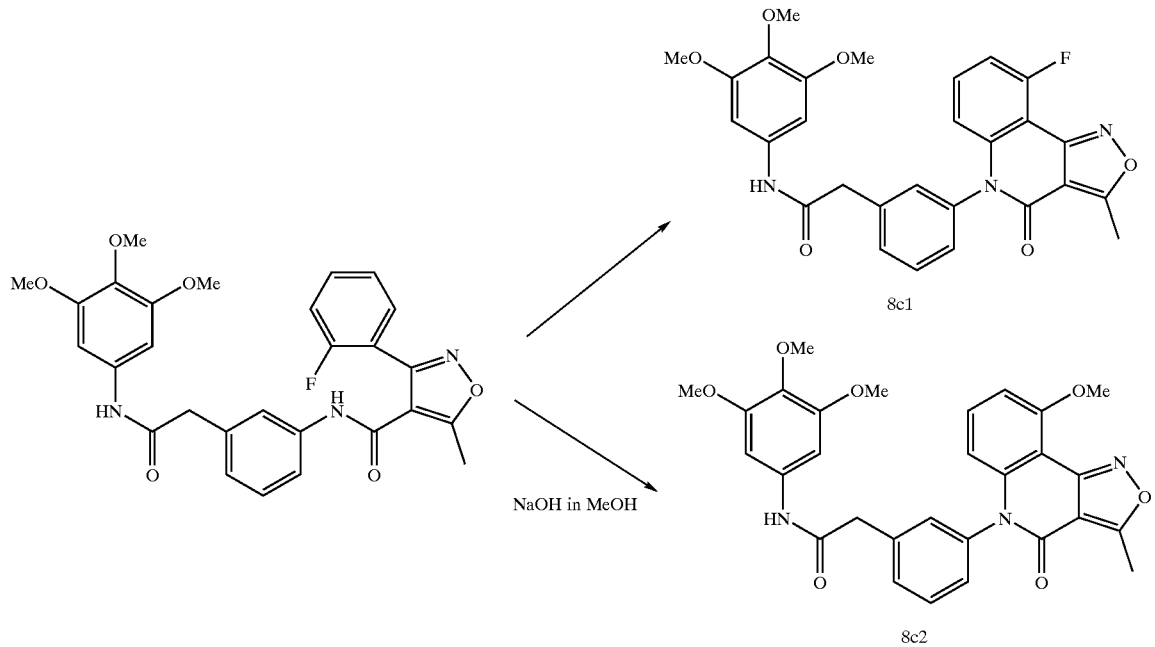

In a manner similar to that in example 10, the product from preparation 27 (0.109 g, 0.20 mmol), 2N NaOH in MeOH (2 ml), and DMF (4 ml) provided 8c1 (35 mg, 34%) and 8c2 (10 mg, 9%) after radial chromatography (silica gel, CH$_2$Cl$_2$/acetone gradient).

N-3,4,5-Trimethoxyphenyl-3-[3-methyl-isoxazolo[4,5c]-1,2-dihydro-6-fluoroquinolin-2-on-1-yl]phenylacetamide:

$^1$H NMR (400 MHz, CDCl$_3$) δ 7.60 (t, 1H, J=7.8 Hz), 7.48 (d, 1H, J=7.8 Hz), 7.29–7.20 (m, 4H), 7.00 (t, 1H, J=8.8 Hz), 6.78 (s, 2H), 6.41 (d, 1H, J=8.8 Hz), 3.79 (s, 6H), 3.75 (s, 5H), 2.84 (s, 3H)ppm. MS (FAB) Calc. 518.1727, found 518.1727.

N-3,4,5-Trimethoxyphenyl-3-[3-methyl-isoxazolo[4,5-c]-1,2-dihydro-6-methoxyquinolin-2-on-1-yl]phenylacetamide:

$^1$H NMR (400 MHz, CDCl$_3$) δ 7.60 (t, 1H, J=7.8 Hz), 7.47 (m, 1H), 7.27–7.15 (m, 5H), 6.78 (s, 2H), 6.21 (d, 1H, J=8.3 Hz), 4.06 (s, 3H), 3.80 (s, 6H), 3.77 (s, 2H), 3.75 (s, 3H), 2.83 (s, 3H)ppm. MS (FAB) Calc. 530.1927, found 530.1922.

Example 14

N-3,4,5-Trimethoxyphenyl-3-[3-hexyl-isoxazolo[4,5-c]-1,2-dihydro-6-chloroquinolin-2-on-1-yl]phenylacetamide

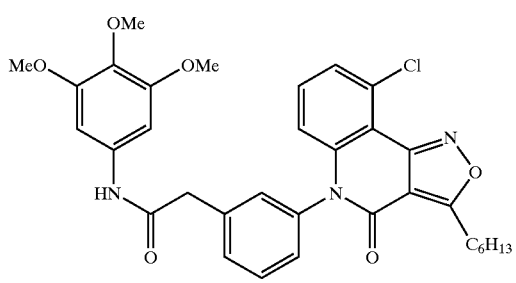

Treatment of the product from preparation 30 (0.175 g, 0.28 mmol) in DMF (6 ml) was treated with 2N NaOH in MeOH (3 ml) for 18 h. Dilution with EtOAc followed by washing (H$_2$O then brine), drying (MgSO$_4$), filtration, and concentration gave the crude product that was purified by column chromatography (silica gel, CH$_2$Cl$_2$/acetone gradient) to give the title compound (0.102 g, 60%).

¹H NMR (400 MHz, CDCl₃) δ (7.60 (t, 1H, J=7.8 Hz), 7.48 (d, 1H, J=7.8 Hz), 7.30 (d, 1H, J=6.8 Hz), 7.22–7.16 (m, 4H), 6.77 (s, 2H), 6.55 (d, 1H, J=7.8 Hz), 3.79 (s, 6H), 3.76 (s, 2H), 3.75 (s, 3H), 3.24 (dt, 2H, J=2.5, 7.3 Hz), 1.80 (quintet, 2H, J=7.3 Hz), 1.30–1.20 (m, 4H), 0.82 (t, 3H, J=6.8 Hz)ppm. MS (FAB) calc. 604.2214, found 604.2218.

Examples 15 and 16

N-3,4,5-Trimethoxyphenyl-3-[3-methyl-isoxazolo[4,5-c]-1,2-dihydro-4-fluoroquinolin-2-on-1-yl]phenylacetamide & N-3,4,5-Trimethoxyphenyl-3-[3-methyl-isoxazolo[4,5-c]-1,2-dihydro-4-methoxyquinolin-2-on-1-yl]phenylacetamide

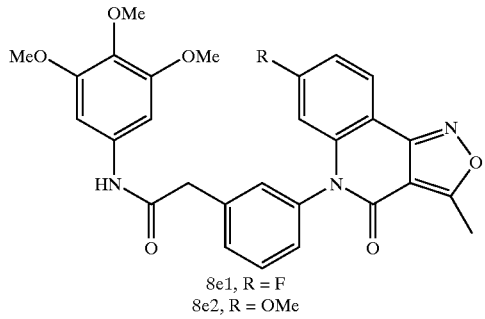

8e1, R = F
8e2, R = OMe

In a fashion similar to that for example 10, compound from preparation 35 (70 mg, 0.13 mmol), dimethylformamide (7 ml), and 2 N NaOH in methanol (3.5 ml) were reacted to give 8e1 (30 mg, 45%) and 8e2 (6 mg, 9%) after column chromatography (silica gel, CH₂Cl₂/acetone gradient).

N-3,4,5-Trimethoxyphenyl-3-[3-methyl-isoxazolo[4,5-c]-1,2-dihydro-4-fluoroquinolin-2-on-1-yl]phenylacetamide:

¹H NMR (400 MHz, CDCl₃) δ 8.17 (dd, 1H, J=5.9, 8.3 Hz), 7.62 (t, 1H, J=7.8 Hz), 7.50 (d, 1H, J=7.3 Hz), 7.25–7.20 (m, 2H), 7.08 (s, 1H), 6.94 (dt, 1H, J=7.8 Hz), 6.78 (s, 2H), 6.31 (dd, 1H, J=2.4, 10.7 Hz), 3.80 (s, 6H), 3.77 (s, 2H), 3.75 (s, 3H), 2.84 (s, 3H)ppm. MS (ES) (m/z) 517.9 [M+1].

N-3,4,5-Trimethoxyphenyl-3-[3-methyl-isoxazolo[4,5-c]-1,2-dihydro-4-methoxyquinolin-2-on-1-yl]phenylacetamide:

¹H NMR (400 MHz, CDCl₃) δ 8.10 (d, 1H, J=8.8 Hz), 7.60 (t, 1H, J=7.8 Hz), 7.46 (d, 1H, J=7.8 Hz), 7.25–7.20 (m, 2H), 7.10 (s, 1H), 6.78 (m, 3H), 6.08 (d, 1H, J=2.0 Hz), 3.79 (s, 6H), 3.76 (m, 2H), 3.75 (s, 3H), 3.65 (s, 3H), 2.80 (s, 3H)ppm. MS (ES) (m/z) 529.9 [M+1].

Example 17

N-3,4,5-Trimethoxyphenyl-3-[3-methyl-isoxazolo[4,5-c]-1,2-dihydro-4-bromoquinolin-2-on-1-yl]phenylacetamide

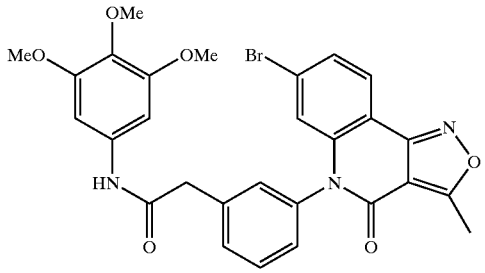

In a fashion similar to that described for example 10, the product from preparation 40 (50 mg, 0.084 mmol), 2N NaOH in methanol (2.5 ml), and dimethylformide (5.0 ml) were reacted to give (32 mg, 67%) after column chromatography (silica gel, hexanes/ethyl acetate gradient).

¹H NMR (400 MHz, CDCl₃) δ 8.04 (d, 1H, J=8.8 Hz), 7.61 (t, 1H, J=7.8 Hz), 7.50 (d, 1H, J=7.3 Hz), 7.35 (dd, 1H, J=2.0, 8.3 Hz), 7.24 (m, 2H), 7.12 (s, 1H), 6.79 (s, 2H), 6.76 (d, 1H, J=2.0 Hz), 3.79 (s, 6H), 3.78 (s, 2H), 3.75 (s, 3H), 2.82 (s, 3H)ppm. MS (ES) (m/z) 578.0 [M+1], 580.0 [M+3].

Example 18

N-3,4,5-Trimethoxyphenyl-3-[3-methyl(tetrahydropyran-2-yl)-isoxazolo[4,5-c]-1,2-dihydro-6-chloroquinolin-2-on-1-yl]phenylacetamide

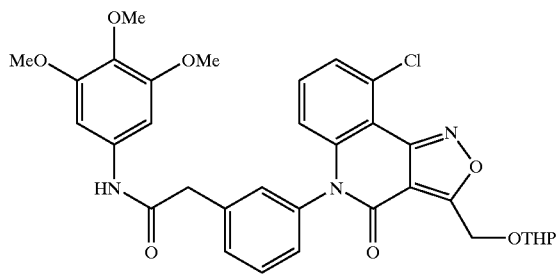

To a solution from preparation 42 (1.05 g, 1.60 mmol) in DMF (30 ml) was added powdered K₂CO₃ (2 g) at room temperature. After stirring 18 h, ethyl acetate was added and the mixture was washed (H₂O then brine), dried (MgSO₄), filtered, and concentrated. Chromatography (silica gel, hexanes/dichloromethane/ethyl acetate gradient) gave the title compound (0.84 g, 83%).

¹H NMR (400 MHz, CDCl₃) δ 7.60 (t, 1H, J=7.8 Hz), 7.48 (d, 1H, J=7.8 Hz), 7.32 (dd, 1H, J=1.0, 7.8 Hz), 7.30–7.20 (m, 4H), 6.78 (s, 2H), 6.56 (1H, dd, J=1.0, 8.8 Hz), 5.21 (dd, 1H, J=2.9, 14.2 Hz), 5.10 (dd, 1H, J=2.9, 14.2 Hz), 4.85 (t, 1H, J=3.4 Hz), 3.86 (ddd, 1H, J=2.9, 9.3, 12.2 Hz), 3.79 (s, 6H), 3.75 (s, 5H), 3.50 (ddd, 1H, J=3.9, 5.4, 10.7 Hz), 1.80–1.40 (m, 6H)ppm. MS (ES) (m/z) 632.2 [M−1].

Example 19

N-3,4,5-Trimethoxyphenyl-3-[3-hydroxymethyl-isoxazolo[4,5-c]-1,2-dihydro-6-chloroquinolin-2-on-1-yl]phenylacetamide

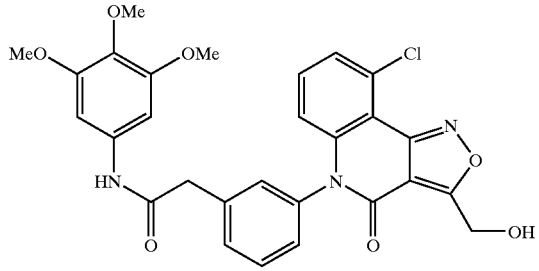

To a solution from example 18 (0.830 g, 1.3 mmol) in methanol (50 ml) and dichloromethane (25 ml) was added p-toluenesulfonic acid hydrate (0.070 g). After stirring 2 h, ethyl acetate was added and the mixture washed with $H_2O$, saturated sodium bicarbonate, brine, dried ($MgSO_4$), filtered, and concentrated. Column chromatography (silica gel, dichloromethane/acetone) gave the title compound (0.702 g, 98%).

$^1$H NMR (400 MHz, $CDCl_3$) δ 7.63 (t, 1H, J=7.8 Hz), 7.53 (d, 1H, J=7.8 Hz), 7.37 (dd, 1H, J=1.0, 7.8 Hz), 7.28 (d, 1H, 8.3 Hz), 7.27–7.17 (m, 3H), 6.75 (s, 2H), 6.61 (d, 1H, J=7.8 Hz), 5.43 (t, 1H, J=6.8 Hz), 5.07 (d, 2H, J=6.8 Hz), 3.78 (s, 6H), 3.77 (s, 2H), 3.75 (s, 3H)ppm. MS (EI) (m/z) 548.2 [M−1].

Example 20

N-3,4,5-Trimethoxyphenyl-3-[3-azidomethyl-isoxazolo[4,5-c]-1,2-dihydro-6-chloroquinolin-2-on-1-yl)phenylacetamide

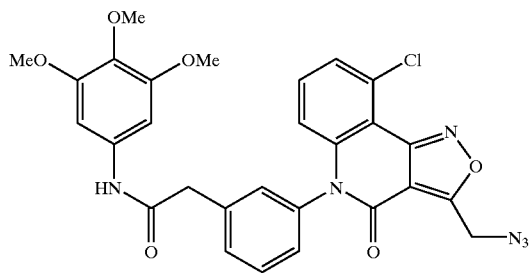

To a solution of example 19 (106 mg, 0.193 mmol) and triethyl amine (0.161 ml, 1.16 mmol) in dichloromethane ($N_2$, 0° C.) was added methane sulfonyl chloride (0.075 ml, 0.77 mmol). The reaction was warmed to room temperature after 10 minutes and diluted with dichloromethane and water. The separated organic fraction was washed (brine), dried ($MgSO_4$), filtered, and concentrated to give the crude mesylate which was stripped down with toluene (twice). The mesylate and sodium azide (75 mg, 1.2 mmol) were dissolved in DMF (3 ml) at room temperature. After 5 minutes ethyl acetate was added and the mixture washed with saturated $NaHCO_3$, $H_2O$, brine, filtered, and concentrated. Column chromatography (silica gel, 10% acetone in dichloromethane) gave the title compound (83 mg, 72%).

$^1$H NMR (400 MHz, $CDCl_3$) δ 7.60 (t, 1H, J=7.8 Hz), 7.50 (d, 1H, 7.8 Hz), 7.34 (m, 2H), 7.26 (d, 1H, J=8.3 Hz), 7.21 (m, 2H), 6.78 (s, 2H), 6.59 (d, 1H,J=8.2 Hz), 4.89 (s, 2H), 3.78 (s, 6H), 3.75 (s, 5H)ppm. MS (ES) (m/z) 575.2 [M+1].

Example 21

N-3,4,5-Trimethoxyphenyl-3-[3-t-butoxycarbonylaminomethyl-isoxazolo[4,5]-1,2-dihydro-6-chloroquinolin-2-on-1-yl]phenylacetamide

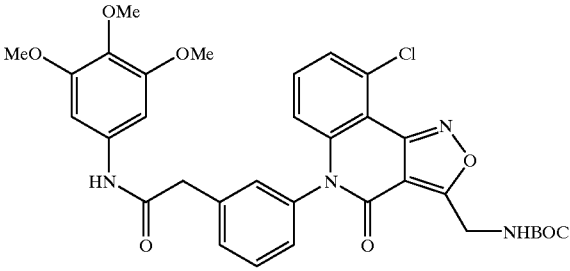

A mixture of example 20 (75 mg, 0.130 mmol), $(BOC)_2O$ (34 mg, 0.16 mmol), Lindlar's catalyst (25 mg), and ethyl acetate (2 ml) was stirred under one atmosphere of hydrogen gas (balloon) for 6 h, filtered through celite, and concentrated. Column chromatography (silica gel, dichloromethane/acetone gradient) gave the title compound (61 mg, 73%).

$^1$H NMR (400 MHz, $CDCl_3$) δ 7.60 (t, 1H, J=7.3 Hz), 7.50 (d, 1H, J=7.8 Hz), 7.31 (d, 1H, J=7.8 Hz), 7.29 (m, 1H), 7.24–7.16 (m, 4H), 6.77 (s, 2H), 6.56 (d, J=8.3 Hz), 5.90 (br s, 1H), 4.83 (m, 2H), 3.77 (s, 6H), 3.75 (s, 2H), 3.74 (s, 3H), 1.38 (s, 9H)ppm. MS (ES) (m/z) 647.5 [M−1].

Example 22

N-3,4,5-Trimethoxyphenyl-3-[3-amidylmethyl-isoxazolo[4,5-c]-1,2-dihydro-6-chloroquinolin-2-on-1-yl]phenylacetamide

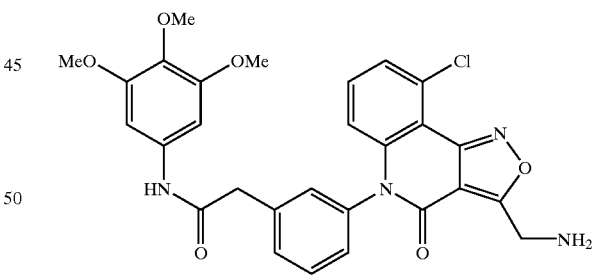

To a solution of example 21 (5.0 mg, 0.0077 mmol) in dichloromethane (0.5 ml) at room temperature was added trifluoroacetic acid (0.5 ml). After 5 minutes the volatiles were removed and the residue was applied to a SCX cation exchange cartridge. Elution with dichloromethane/methanol followed by 2M ammonia in methanol afforded the title compound (2.4 mg, 57%).

$^1$H NMR (400 MHz, $CDCl_3$) δ 7.60 (t, 1H, J=7.8 Hz), 7.51 (d, 1H, J=7.3 Hz), 7.36 (s, 1H), 7.32 (d, 1H, J=7.8 Hz), 7.23–7.18 (m, 3H), 6.78 (s, 2H), 6.57 (d, 1H, J=8.3 Hz), 4.34 (s, 2H), 3.79 (s, 6H), 3.77 (s, 2H), 3.75 (s, 3H)ppm. MS (ES) (m/z) 549.2 [M+1].

Example 23

N-3,4,5-Trimethoxyphenyl-3-[3-mesylmethyl-isoxazolo[4,5]-1,2-dihydro-6-chloroquinolin-2-on-1-yl]phenylacetamide

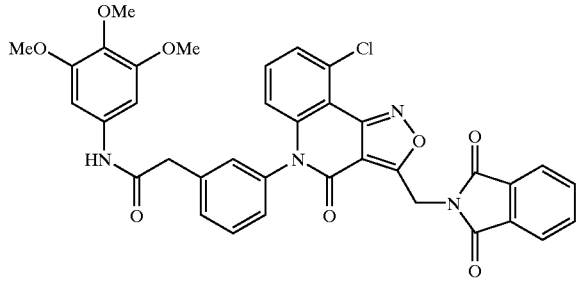

A solution of the product from preparation 55 (47 mg, 0.075 mmol), potassium phthalimide (50 mg, 0.27 mmol), and DMF (2 ml) were allowed to react (17 h) at room temperature. The mixture was diluted with EtOAc then washed (H$_2$O, brine) and dried (MgSO$_4$). Column chromatography (silica gel, CH$_2$Cl$_2$/acetone gradient) gave the title compound (27 mg, 53%).

$^1$H NMR (400 MHz, CDCl$_3$) δ 7.82 (m, 2H), 7.70 (m, 2H), 7.56 (t, 1H, J=7.8 Hz), 7.48 (d, 1H, J=7.8 Hz), 7.36 (s, 1H), 7.26 (d, 1H, J=6.8 Hz), 7.24–7.18 (m, 3H), 6.76 (s, 2H), 6.55 (d, 1H, J=8.3 Hz), 5.41 (s, 2H), 3.76 (s, 6H), 3.72 (s, 5H)ppm. MS (ES) (m/z) 679.2 [M+1].

Example 24

N-3,4,5-Trimethoxyphenyl-3-[3-methylthiomethyl-isoxazolo[4,5-c]-1,2-dihydro-6-chloroquinolin-2-on-1-yl]phenylacetamide

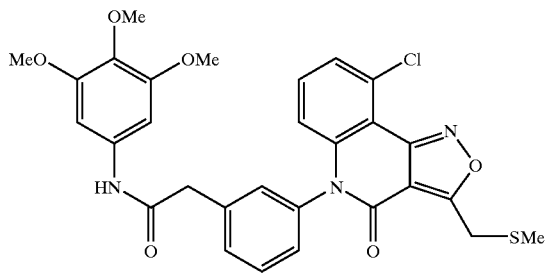

A solution of the product from preparation 55 (50 mg, 0.080 mmol), sodium thiomethoxide (20 mg, 0.29 mmol), and DMF (2 ml) were allowed to react (17 h) at room temperature. The mixture was diluted with EtOAc then washed (H$_2$O, brine) and dried (MgSO$_4$). Column chromatography (silica gel, CH$_2$Cl$_2$/acetone gradient) gave the title compound (41 mg, 82%).

$^1$H NMR (400 MHz, CDCl$_3$) δ 7.70–7.50 (m, 3H), 7.36 (t, 1H, J=7.8 Hz), 7.28–7.21 (m, 3H), 6.83 (s, 2H), 4.23 (s, 2H), 3.81 (s, 6H), 3.79 (s, 5H), 2.25 (s, 3H)ppm. MS (ES) (m/z) 578[M−1], 532 [M−SMe].

Example 25

N-3,4,5-Trimethoxyphenyl-3-[3-thiazol-3-ylmethyl-isoxazolo[4,5-c]-1,2-dihydro-6-chloroquinolin-2-on-1-yl]phenylacetamide

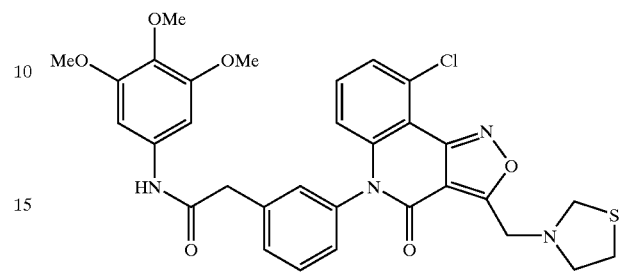

A solution of preparation 55 (26 mg, 0.041 mmol), thiazolidine (0.025 ml, 0.28 mmol), and DMF (2 ml) were allowed to react (17 h) at room temperature. The mixture was diluted with EtOAc then washed (H$_2$O, brine) and dried (MgSO$_4$). Column chromatography (silica gel, CH$_2$Cl$_2$/acetone gradient) gave the title compound etamide (8.6 mg, 34%).

$^1$H NMR (400 MHz, CDCl$_3$) δ 7.58 (t, 1H, J=7.8 Hz), 7.50 (d, 1H, J=7.8 Hz), 7.32 (dd, 1H, J=1.0, 7.8 Hz), 7.27–7.21 (m, 4H), 6.76 (s, 2H), 6.56 (dd, 1H, J=1.0, 8.8 Hz), 4.19 (s, 2H), 4.16 (s, 2H), 3.78 (s, 6H), 3.75 (s, 5H), 3.15 (t, 2H, J=6.8 Hz), 2.91 (t, 2H, J=6.8 Hz)ppm. MS (ES) (m/z) 621.1 [M+1].

Example 26

N-3,4,5-Trimethoxyphenyl-3-[3-methyl-isoxazolo[4,5-c]-1,2-dihydro-6-iodoquinolin-2-on-1-yl]phenylacetamide

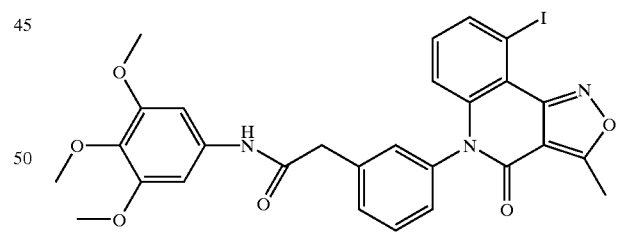

To a solution of preparation 48 (200 mg, 0.32mmol) in DMF (5 ml) was added powdered K$_2$CO$_3$ (88 mg, 0.64 mmol, 2 eq.) and stirred for 48 h. Partitioned between ethyl acetate and 0.1N HCl. Washed organic layer with H$_2$O and brine, dried (MgSO$_4$), filtered and concentrated. The crude material was purified by flash chromatography using 1–15% acetone in dichloromethane to give the title compound (170 g, 88%).

MS (ES) (m/z) 626.1 [M+1]. IR (KBr) 1679.56, 1632.05, 1606.52, 1587.85, 1508.40, 1411.66, 1132.34 cm$^{-1}$.

Example 27

N-3,4,5-Trimethoxyphenyl-3-[3-methyl-isoxazolo[4,5-c]-1,2-dihydro-6-(thien-2-yl)-quinolin-2-on-1-yl]phenylacetamide

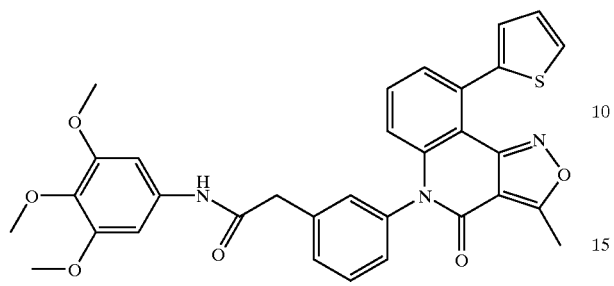

To a mixture of example 26 (100 mg, 0.16 mmol) and tetrakis(triphenylphosphine)-palladium (37 mg, 0.03 mmol, 20% mol) in THF (5 ml) under $N_2$, was added thiophene-2-boronic acid (51 mg, 0.4 mmol, 2.5 eq.) dissolved in minimal ethanol and 2M $Na_2CO_3$ (0.16 ml, 2 eq.), and refluxed for 17 h. The mixture was cooled to room temperature, filtered, concentrated, and partitioned between ethyl acetate and $H_2O$. The organic layer was washed with brine, dried ($MgSO_4$), filtered and concentrated. The crude material was filtered through a silica gel plug using 1–10% acetone in dichloromethane to elute product then further purified by HPLC (hexanes/ethyl acetate gradient) to give the title compound (29 mg, 31%).

MS (ES) (m/z) 582.2 [m+1]. IR (KBr) 1673.21, 1632.48, 1607.11, 1590.64, 1508.38, 1412.20, 1132.29 $cm^{-1}$.

Example 28

N-3,4,5-Trimethoxyphenyl-3-[3-methyl-isoxazolo[4,5-c]-1,2-dihydro-6-(naphth-1-yl)-quinolin-2-on-1-yl]phenylacetamide

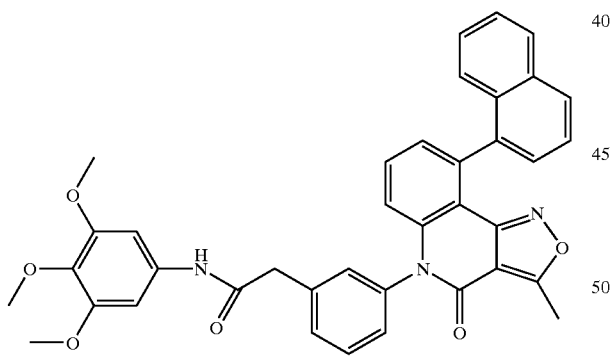

To a mixture of example 26 (100 mg, 0.16 mmol) and tetrakis(triphenylphosphine)-palladium (37 mg, 0.03 mmol, 20% mol), in THF (5 ml) under $N_2$ was added 1-napthylboronic acid (69 mg, 0.4 mmol, 2.5 eq.) dissolved in minimal ethanol and 2M $Na_2CO_3$ (0.16 ml, 2 eq.), and refluxed for 17 h. The mixture was cooled to room temperature, filtered, concentrated, and partitioned between ethyl acetate and $H_2O$. The organic layer was washed with brine, dried ($MgSO_4$), filtered and concentrated. The crude material was filtered through a silica gel plug using 1–10% acetone in dichloromethane to elute then purified by HPLC (hexanes/ethyl acetate gradient) to give the title compound (15 mg, 15%).

MS (ES) (m/z) 626.2 [M+1]. IR (KBr) 1671.79, 1633.18, 1606.98, 1590.77, 1508.30, 1412.31, 1132.32 $cm^{-1}$.

Example 29

N-3,4,5-Trimethoxyphenyl-3-[3-methyl-isoxazolo[4,5-c]-1,2-dihydro-6-(4-methoxyphenyl)-quinolin-2-on-1-yl]phenylacetamide

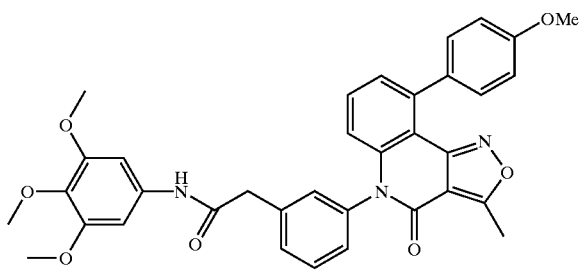

To a mixture of example 26 (100 mg, 0.16 mmol), tetrakis(triphenylphosphine)-palladium (28 mg, 0.024 mmol, 15% mol), in THF (5 ml) under $N_2$ was added 4-methoxyphenylboronic acid (49 mg, 0.32 mmol, 2 eq.) dissolved in minimal ethanol, 2M $Na_2CO_3$ (0.16 ml, 2 eq.), and reaction was refluxed for 17 h. It was then cooled to room temperature, filtered, concentrated, and partitioned between ethyl acetate and $H_2O$. The organic phase was washed with brine, dried ($MgSO_4$), filtered and concentrated. The crude material was run through a silica gel plug using 1–10% acetone in dichloromethane to elute then purified by HPLC (hexanes/ethyl acetate gradient) (2×) to give the title compound (24 mg, 25%).

MS (ES) (m/z) 606.3 [M+1]. IR (KBr) 1672.10, 1632.51, 1608.78, 1592.28, 1508.30, 1245.67, 1245.67, 1132.33 $cm^{-1}$.

Example 30

N-3,4,5-Trimethoxyphenyl-3-[3-methyl-isoxazolo[4,5-c]-1,2-dihydro-6-(4-chlorophenyl)-quinolin-2-on-1-yl]phenylacetamide

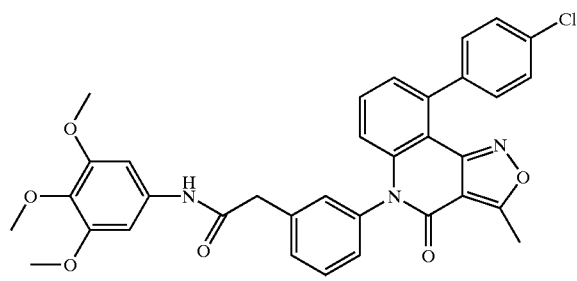

To a mixture of example 26 (100 mg, 0.16 mmol), tetrakis-(triphenylphosphine)-palladium (28 mg, 0.024 mmol, 15% mol), in THF (5 ml) under $N_2$ was added 4-chlorophenylboronic acid (50 mg, 0.32 mmol, 2 eq.) dissolved in minimal ethanol, 2M $Na_2CO_3$ (0.16 ml, 2 eq.), and the reaction was refluxed for 17 h. It was then cooled to room temperature, filtered, concentrated, and partitioned between ethyl acetate and $H_2O$. The organic layer was washed with brine, dried ($MgSO_4$), filtered and concentrated. The crude material was run through a silica gel plug using 1–10% acetone in dichloromethane to elute then

Example 31

N-3,4,5-Trimethoxyphenyl-3-[3-methyl-isoxazolo[4,5-c]-1,2-dihydro-6-(ethylenyl)-quinolin-2-on-1-yl]phenylacetamide

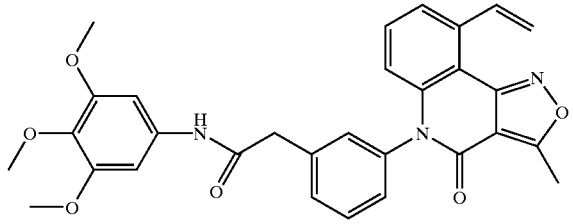

To a mixture of example 26 (100 mg, 0.16 mmol) and PdCl$_2$(PPh$_3$)$_4$ (17 mg, 0.024 mmol, 15%mmol) in THF (3 ml) was added tributylvinyl tin (0.05 ml, 0.18 mmol, 1.1 eq.), and the reaction was refluxed for 24 h. After cooling to room temperature, it was partitioned between ethyl acetate and H$_2$O and the organic layer was washed with brine, dried (MgSO$_4$), and concentrated. The crude material was run through a silica gel plug using ethyl acetate, then purified by HPLC(hexanes/ethyl acetate gradient) to give the title compound (10 mg, 12%).

MS (ES) (m/z) 526.3 [M+1]. IR (KBr) 3286.85, 2933.78, 1668.15, 1606.59, 1543.09, 1507.12, 1410.36, 1329.45, 1231.00, 1128.87, 1008.70 cm$^{-1}$.

Example 32

N-3,4,5-Trimethoxyphenyl-3-[3-methyl-isoxazolo[4,5-c]-1,2-dihydro-6-benzylquinolin-2-on-1-yl]phenylacetamide

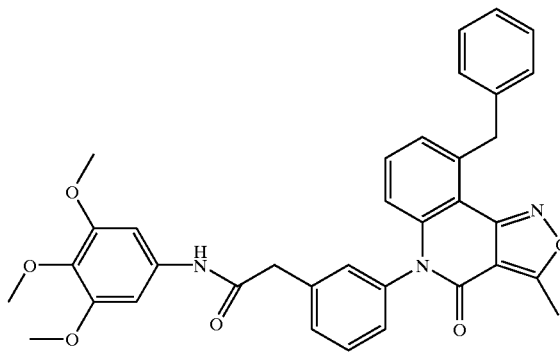

To a mixture of 0.5M benzyl-9-BBN (1 ml) in DMF (2 ml) under N$_2$ was added PdCl$_2$ (26 mg, 0.032 mmol, 20%mmol), the product from example 26 (100 mg, 0.16 mmol), and powdered K$_2$CO$_3$ (44 mg, 0.32 mmol, 2 eq.). It was then heated at 50° C. for 24 h. then cooled to room temperature. Ice H$_2$O was added and extracted with ethyl acetate (2×). The combined organic layers were washed with H$_2$O brine, dried (MgSO$_4$), filtered and concentrated. The crude material was run through a silica gel plug using 1–10% acetone in dichloromethane then purified by HPLC (hexanes/ethyl acetate gradient) to give the title compound (4 mg, 4%).

purified by HPLC (hexanes/ethyl acetate gradient) (2×) to give the title compound (28 mg, 29%).

MS (ES) (m/z) 610.3 [M+1]. IR (KBr) 1675.84, 1632.45, 1606.41, 1591.95, 1508.06, 1477.21, 1411.64, 1132.01 cm$^{-1}$.

$^1$H NMR (400 MHz, CDCl$_3$) δ 7.63 (t, 1H), 7.50 (d, 1H), 7.30–7.21 (m, 8H), 6.97 (d, 1H), 6.82 (s, 2H), 6.53 (d, 1H), 4.72 (s, 2H), 3.82 (s, 6H), 3.79 (s, 3H), 2.86 (t, 3H)ppm. MS (ES) (m/z) 590.4 [M+1].

Example 33

N-3,4,5-Trimethoxyphenyl-3-[3-methyl-isoxazolo[4,5c]-1,2-dihydro-6-methoxycarbonyl-quinolin-2-on-1-yl]phenylacetamide

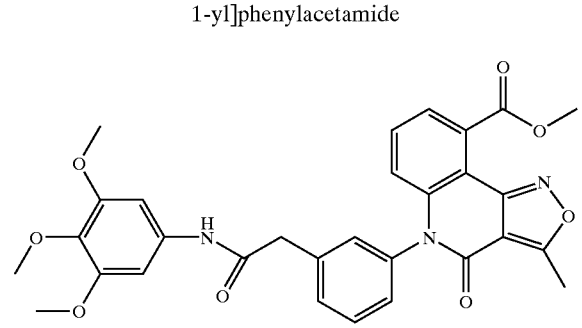

A mixture of example 26 (200 mg, 032 mmol), Pd(OAc)$_2$ (22.5 mg), methanol (7 ml), acetonitrile (30 ml), and triethylamine (0.16 ml) was heated to 60° C. for 24 h with 60 psi Carbon monoxide. After celite filtration and concentration, the crude material was run through a silica gel plug using 1–10% acetone in dichloromethane, then purified by HPLC (hexanes/ethyl acetate gradient) to give the title compound (44 mg, 25%).

MS (ES) (m/z) 558.1 [M+1]. IR (KBr) 1735.99, 1685.23, 1632.98, 1605.89, 1507.07, 1486.61, 1450.39, 1410.73, 1313.11, 1290.07, 1231.18, 1127.96 cm$^{-1}$.

Example 34

N-3,4,5-Trimethoxyphenyl-3-[3-methyl-isoxazolo[4,5-c]-1,2-dihydro-6-carboxy-quinolin-2-on-1-yl]phenylacetamide

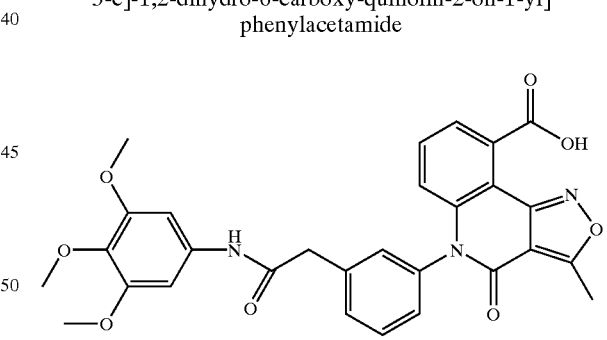

A solution of example 33 (20 mg, 0.04 mmol) in methanol (0.5 ml) was treated with 1N NaOH (0.07 ml, 2 eq.) and heated at 50° C. for 24 h. The reaction was cooled to room temperature and ice H$_2$O was added. Organic impurities were removed with hexanes, then the solution was acidified to pH 2 and extracted with ethyl acetate (2×). The organic layer was washed with H$_2$O, then brine, dried (MgSO$_4$), filtered, and concentrated to give the title compound (18 mg, 92%).

MS (ES) (m/z) 544.3 [M+1]. IR (KBr) 3271.51, 2935.24, 1717.49, 1672.13, 1632.11, 1595.29, 1536.64, 1506.49, 1451.73, 1412.95, 1332.17, 1225.33, 1129.35, 1007.60, 813.62 cm$^{-1}$.

Example 35

N-3,4,5-Trimethoxyphenyl-3-[3-methyl-isoxazolo[4,5-c]-1,2-dihydro-5-iodoquinolin-2-on-1-yl]phenylacetamide

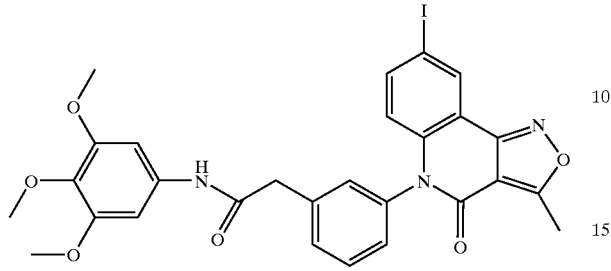

To a solution of preparation 54 (200 mg, 0.32 mmol) in DMF (5 ml) was added powdered $K_2CO_3$ (88 mg, 0.64 mmol, 2 eq.) and stirred for 17 h. The reaction was partitioned between ethyl acetate and 0.1N HCl, and washed organic layer with $H_2O$ and brine, dried ($MgSO_4$), filtered and concentrated. The crude material was purified by flash chromatography (silica) using 1–20% acetone in dichloromethane to give the title compound (168 g, 87%).

MS (ES) (m/z) 626.1 [M+1]. IR (KBr) 1678.85, 1630.32, 1603.94, 1508.59, 1484.62, 1132.20 cm$^{-1}$.

Example 36

N-3,4,5-Trimethoxyphenyl-3-[3-methyl-isoxazolo[4,5-c]-1,2-dihydro-5-(4-trifluoromethylphenyl)-quinolin-2-on-1-yl]phenylacetamide

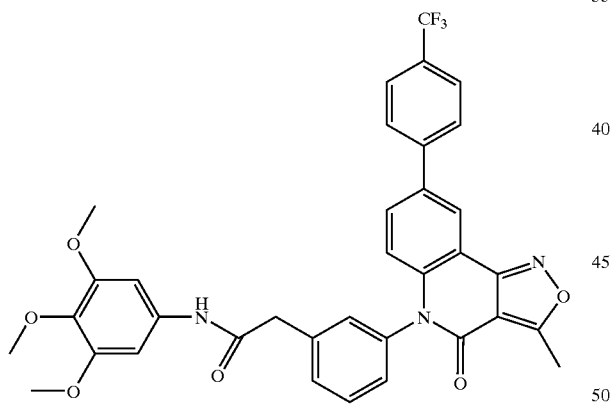

To a mixture of example 35 (100 mg, 0.16 mmol), tetrakis(triphenylphosphine)-palladium (28 mg, 0.024 mmol, 15% mol), in THF (5 ml) under $N_2$ was added 4-Trifluoromethylphenylboronic acid (50 mg, 0.32 mmol, 2 eq.) dissolved in minimal ethanol, 2M $Na_2CO_3$ (0.16 ml, 2 eq.), and refluxed for 24 h. Rxn was cooled to room temperature, filtered, concentrated, and partitioned between ethyl acetate and $H_2O$. The organic layer was washed with brine, dried ($MgSO_4$), filtered and concentrated. The crude material was run through a silica gel plug using 1–15% acetone in dichloromethane to elute then purified by HPLC (hexanes/ethyl acetate gradient) to the title compound (46 mg, 45%).

MS (ES) (m/z) 644.3 [M+1]. IR (KBr) 1679.00, 1617.95, 1508.45, 1325.99, 1132.03 cm$^{-1}$.

Example 37

N-3,4,5-Trimethoxyphenyl-3-[3-methyl-isoxazolo[4,5-c]-1,2-dihydro-5-naphthyl-quinolin-2-on-1-yl]phenylacetamide

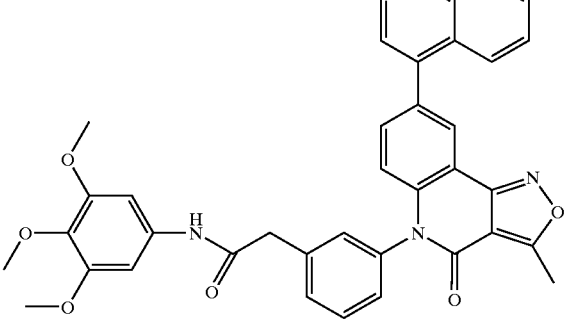

To a mixture of example 35 (100 mg, 0.16 mmol), tetrakis(triphenylphosphine)-palladium (28 mg, 0.024 mmol, 15% mol), in THF (5 ml) under $N_2$ was added 1-napthylboronic acid (50 mg, 0.32 mmol, 2 eq.) dissolved in minimal ethanol, 2M $Na_2CO_3$ (0.16 ml, 2 eq.), and refluxed for 24 h. The reaction was cooled to room temperature, filtered, concentrated, and partitioned between ethyl acetate and $H_2O$. Washed organic layer with brine, dried ($MgSO_4$), filtered and concentrated. The crude material was run through a silica gel plug using 1–15% acetone in dichloromethane, then purified by HPLC (hexanes/ethyl acetate gradient) to give the title compound (70 mg, 70%).

MS (ES) (m/z) 610.3 [M+1]. IR (KBr) 1672.33, 1634.42, 1619.23, 1607.85, 1508.41, 1498.70, 1452.75, 1412.20, 1237.11, 1132.15 cm$^{-1}$.

Example 38

N-3,4,5-Trimethoxyphenyl-3-[3-methyl-isoxazolo[4,5-c]-1,2-dihydro-5-(thien-2-yl)-quinolin-2-on-1-yl]phenylacetamide

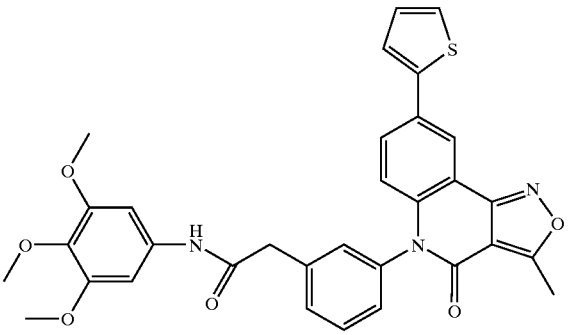

To a mixture of example 35 (100 mg, 0.16 mmol), tetrakis(triphenylphosphine)-palladium (28 mg, 0.024 mmol, 15% mol), in THF (5 ml) under N2 was added thiophene-2-boronic acid (41 mg, 0.32 mmol, 2 eq.) dissolved in minimal ethanol, 2M Na₂CO₃ (0.16 ml, 2 eq.), and refluxed for 24 h. The reaction was cooled to room temperature, filtered, concentrated, and partitioned between ethyl acetate and H₂O. The mixture was washed with brine, dried (MgSO₄), filtered and concentrated. The crude material was run through a silica gel plug using 1–15% acetone in dichloromethane, then purified by HPLC (hexanes/ethyl acetate gradient) to give the title compound (52 mg, 56%)].

MS (ES) (m/z) 582.2 [M+1]. IR (KBr) 1675.07, 1619.94, 1607.44, 1508.48, 1495.78, 1132.25 cm⁻¹.

Example 39

N-3,4,5-Trimethoxyphenyl-3-[3-methyl-isoxazolo[4,5-c]-1,2-dihydro-5-(4-methoxyphenyl)-quinolin-2-on-1-yl]phenylacetamide

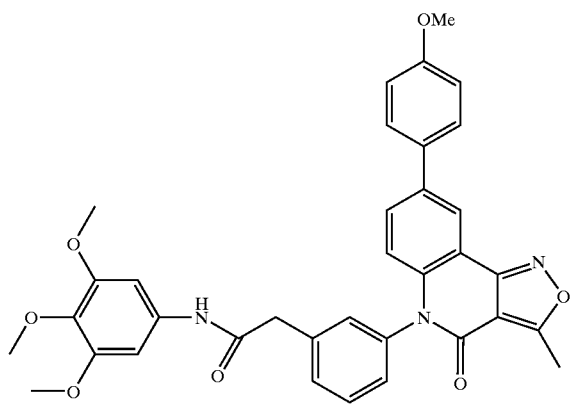

To a mixture of example 35 (10 mg, 0.16 mmol), tetrakis(triphenylphosphine)-palladium (6 mg, 0.006 mmol, 3% mol), in THF (4 ml) under N₂ was added 4-methoxyphenylboronic acid (27 mg, 0.18 mmol, 1.1 eq.) dissolved in minimal ethanol, 2M Na₂CO₃ (0.18 ml, 1.1 eq.), and refluxed for 24 h. The reaction was cooled to room temperature, filtered, concentrated, and partitioned between ethyl acetate and H₂O. The organic layer was washed with brine, dried (MgSO₄), filtered and concentrated. The crude material was run through a silica gel plug using 1–15% acetone in dichloromethane, then purified by HPLC (hexanes/ethyl acetate gradient) to give the title compound (33 mg, 34%).

MS (ES) (m/z) 606.3 [M+1]. IR (KBr) 1674.98, 1619.77, 1608.84, 1508.35, 1491.99, 1132.22 cm⁻¹.

Example 40

N-3,4,5-Trimethoxyphenyl-3-[3-methyl-isoxazolo[4,5-c]-1,2-dihydro-5-(4-chlorophenyl)-quinolin-2-on-1-yl]phenylacetamide

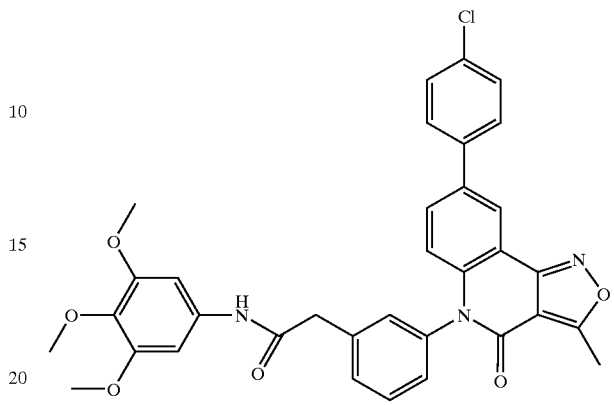

To a mixture of example 19 (100 mg, 0.16 mmol), tetrakis(triphenylphosphine)-palladium (6 mg, 0.006 mmol, 3% mol), in THF (4 ml) under N₂ was added 4-chlorophenylboronic acid (28 mg, 0.18 mmol, 1.1 eq.) dissolved in minimal ethanol, 2M Na₂CO₃ (0.18 ml, 1.1 eq.), and refluxed for 24 h. The reaction was cooled to room temperature, filtered, concentrated, and partitioned between ethyl acetate and H₂O. The organic layer was washed with brine, dried (MgSO₄), filtered and concentrated. The crude material was run through a silica gel plug using 1–10% acetone in dichloromethane, then purified by HPLC (hexanes/ethyl acetate gradient) to give the title compound (38 mg, 39%).

MS (ES) (m/z) 610.1 [M+1]. IR (KBr) 1675.47, 1619.83, 1508.75, 1485.81 cm⁻¹.

Example 41

N-3,4,5-Trimethoxyphenyl-3-[3-methyl-isoxazolo[4,5-c]-1,2-dihydro-5-(methoxycarbonyl)-quinolin-2-on-1-yl]phenylacetamide

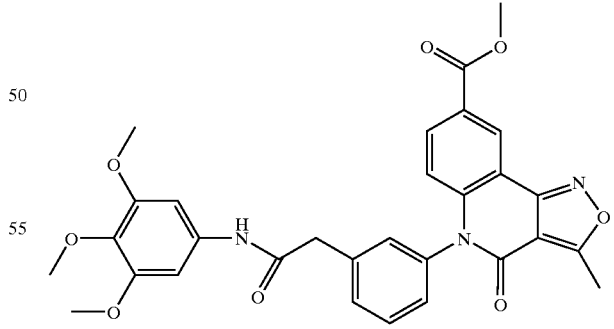

A mixture of example 35 (100 mg, 016 mmol), Pd(OAc)₂ (18 mg), methanol (5 ml), acetonitrile (25 ml), and triethylamine (0.13 ml) was heated to 60° C. for 24 h under 60 psi Carbon monoxide. The crude was filtered through a celite plug and concentrated. The crude material was purified by flash chromatography using 1–10% acetone in dichloromethane to give the title compound (41 mg, 46%).

MS (ES) (m/z) 558.2 [M+1]. IR (KBr) 1721.23, 1684.85, 1608.69, 1619.50, 1508.33, 1412.22, 1274.85, 1412.22, 1274.85, 1233.15, 1131.68 cm$^{-1}$.

Example 42

N-3,4,5-Trimethoxyphenyl-3-[3-methyl-isoxazolo[4,5-c]-1,2-dihydro-5-carboxy-quinolin-2-on-1-yl]phenylacetamide

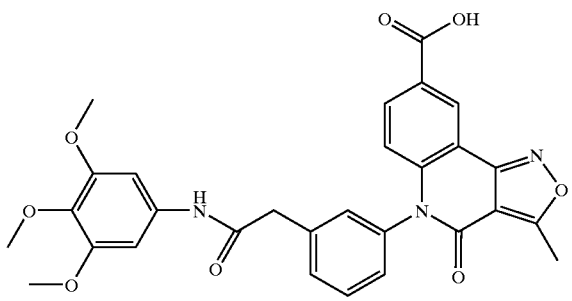

A solution of example 41 (25 mg, 0.05 mmol) in methanol (0.5 ml) and THF (0.25 ml) was treated with 1N NaOH (0.17 ml, 2 eq.) and heated at 50° C. for 2 h 30 min. The reaction was cooled to room temperature, diluted with ice H$_2$O, and organic impurities were extended with hexanes. The aqueous layer was acidified to pH 2, then extracted with ethyl acetate (2×). The organic layer was washed with H$_2$O, brine, dried (MgSO$_4$), filtered, and concentrated to give the title compound (24 mg, 100%). MS (ES) (m/z) 542.3 [M-1]. IR (KBr) 3356.3, 2945.2, 1675.05, 1618.10, 1506.87, 1234.68, 1128.89 cm$^{-1}$.

Example 43

N-3,4,5-Trimethoxyphenyl-3-[3-methylthioisoxazolo[4,5-c]-1,2-dihydro-6-chloroquinolin-2-on-1-yl]phenylacetamide

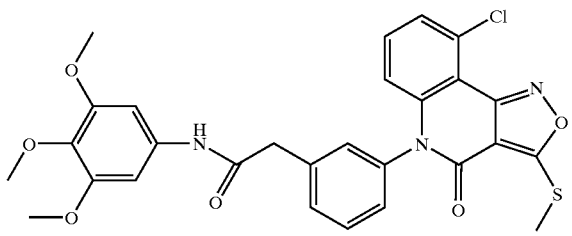

To a solution of preparation 5 (17 mg, 0.03 mmol) in DMF (3 ml) under N$_2$ was added sodium methylthiolate (11 mg, 0.15 mmol, 5 eq.). The solution was stirred for 45 min., partitioned between ethyl acetate and H$_2$O. The organic layer was washed with brine, dried (MgSO$_4$), filtered and concentrated. The crude material was purified by flash chromatography using 1–10% acetone in dichloromethane to give the title compound (6 mg, 35%).

MS (FAB) (m/z) 561.1. IR (KBr) 1679.98, 1656.59, 1600.17, 1578.25, 1507.22, 1460.51, 1455.02, 1410.12, 1229.79, 1136.54.

Example 44

N-3,4,5-Trimethoxyphenyl-3-[3-chloroisoxazolo[4,5-c]-1,2-dihydro-6-chloroquinolin-2-on-1-yl]phenylacetamide

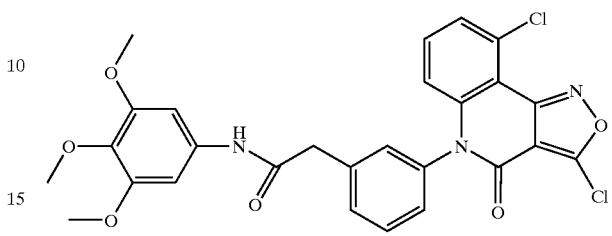

To a solution of preparation 5 (0.5 g, 0.88 mmol) in DMF (50 ml) under N$_2$ was added dropwise 1.0M sodium trimethylsilanolate (0.9 ml, 1.05 eq.) over 3.6 h. The mixture was partitioned between ethyl acetate and 0.1N HCl, and the organic layer was washed with H$_2$O, brine, dried (MgSO$_4$), filtered and concentrated. The crude material was purified by flash chromatography using 10–75%ethyl acetate in dichloromethane to give the title compound (224 mg, 46%).

Anal. Calc. for C$_{27}$H$_{21}$Cl$_2$N$_3$O$_6$; Theoretical: C, 58.50, H, 3.82, N, 7.58; Found: C, 58.84, H, 5.05, 7.87%. IR (KBr) 1673.09, 1593.79, 1459.25, 1132.05 cm$^{-1}$.

Example 45

N-3,4,5-Trimethoxyphenyl-3-[3-(diethylamidyl)-isoxazolo[4,5]-1,2-dihydro-6-chloroquinolin-2-on-1-yl]phenylacetamide

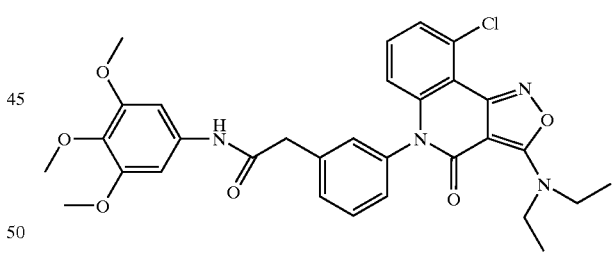

To a solution of example 44 (50 mg, 0.09 mmol) in DMF (5 ml) under N$_2$ was added diethylamine (28 ul, 0.27 mmol, 3 eq.). The solution was stirred at room temperature for 30 min, then partitioned between ethyl acetate and 0.1N HCl. The organic layer was washed with H$_2$O, brine, dried (MgSO$_4$), filtered and concentrated. The crude material was purified by flash chromatography using 1–10% acetone in dichloromethane to give the title compound (32 mg, 60%).

$^1$H NMR (400 MHz, CDCl$_3$) δ 7.58 (t, 1H), 7.47 (d, 1H), 7.44 (s, 1H), 7.23–7.19 (m, 3H), 7.13 (t, 1H), 6.79 (s, 2H), 6.40 (d, 2H), 3.89 (q, 4H), 3.79 (s, 6H), 3.78 (s, 3H), 3.73 (s, 2H), 1.26 (t, 6H)ppm. MS (ES) (m/z) 591.4 [M+1].

Example 46

N-3,4,5-Trimethoxyphenyl-3-[3-(dipropylamidyl)-isoxazo)o[4,5-c]-1,2-dihydro-6-chloroquinolin-2-on-1-yl]phenylacetamide

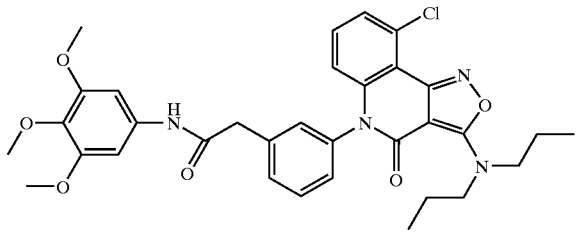

To a solution of example 44 (50 mg, 0.09 mmol) in DMF (5 ml) under N$_2$ was added dipropylamine (37 ul, 0.27 mmol, 3 eq.). The solution was stirred at room temperature for 30 min, then partitioned between ethyl acetate and 0.1N HCl. The organic layer was washed with H$_2$O, brine, dried (MgSO$_4$), filtered and concentrated. The crude material was purified by flash chromatography using 1–10% acetone in dichloromethane to give the title compound (20 mg, 36%).

$^1$H NMR (400 MHz, CDCl$_3$) δ 7.59 (t, 1H), 7.47 (d, 1H), 7.41 (s, 1H), 7.23–7.19 (m, 3H), 7.13 (t, 1H), 6.79 (s, 2H), 6.40 (d, 2H), 3.85–3.79 (m, 4H), 3.80 (s, 6H), 3.78 (s, 3H), 3.75 (s, 2H), 1.70–1.64 (m, 4H), 0.88 (t, 6H)ppm. MS (ES) (m/z) 619.5 [M+1].

Example 47

N-3,4,5-Trimethoxyphenyl-3-[3-(4-methoxyanilino)-isoxazolo[4,5-c]-1,2-dihydro-6-chloroquinolin-2-on-1-yl]phenylacetamide

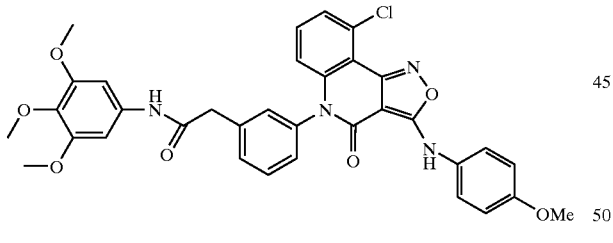

To a solution of example 44 (50 mg, 0.09 mmol) in DMF (5 ml) under N$_2$ was added p-anisidine (55 mg, 0.45 mmol, 5 eq.). The solution was stirred at room temperature for 1 h 45 min, then partitioned between ethyl acetate and 0.1N HCl. The organic layer was washed with H$_2$O, brine, dried (MgSO$_4$), filtered and concentrated. The crude material was purified by flash chromatography using 1–15% acetone in dichloromethane to give the title compound (26 mg, 45%).

$^1$H NMR (400 MHz, CDCl$_3$) δ 8.61 (s, 1H), 7.59 (t, 1H), 7.56 (s, 1H), 7.53 (d, 1H), 7.32 (d, 2H), 7.27 (s, 1H), 7.22–7.18 (m, 3H), 6.87 (d, 2H), 6.83 (s, 2H), 6.58 (d, 2H), 3.79 (s, 9H), 3.78 (s, 3H), 3.74 (s, 2H)ppm. MS (ES) (m/z) 663.162 [M+Na].

Example 48

N-3,4,5-Trimethoxyphenyl-3-[3-(thiazol-3-yl)-isoxazolo[4,5-c]-1,2-dihydro-6-chloroquinolin-2-on-1-yl]phenylacetamide

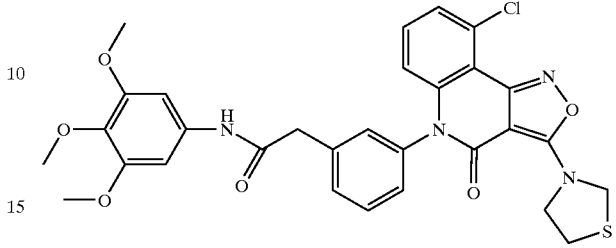

To a solution of example 44 (20 mg, 0.04 mmol) in DMF (2 ml) under N$_2$ was added thiazolidine (18 ul, 0.24 mmol, 6 eq.). The solution was stirred at room temperature for 1 h, then partitioned between ethyl acetate and H$_2$O. The organic layer was washed with brine, dried (MgSO$_4$), filtered and concentrated. The crude material was purified by flash chromatography using 1–10% acetone in dichloromethane to give the title compound (16 mg, 67%).

$^1$H NMR (400 MHz, CDCl$_3$) δ 7.61 (t, 1H), 7.51 (d, 1H), 7.27–7.25 (m, 1H), 7.22–7.16 (m, 3H), 6.78 (s, 2H), 6.47 (d, 1H), 5.09 (s, 1H), 4.26 (t, 2H) 3.81 (s, 6H), 3.79 (d, 3H), 3.77 (s, 2H), 3.11 (t, 2H)ppm. MS (FAB) (m/z) 607.2 [M+1].

Example 49

N-3,4,5-Trimethoxyphenyl-3-[3-benzylthio-isoxazolo[4,5-c]-1,2-dihydro-6-chloroquinolin-2-on-1-yl]phenylacetamide

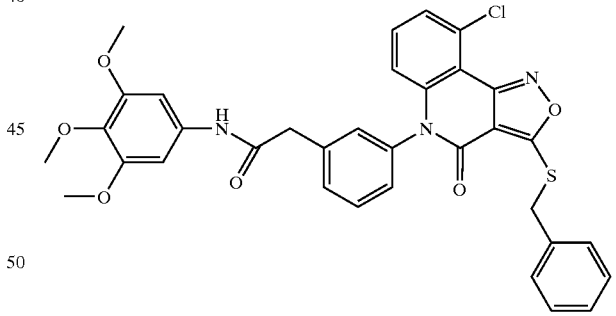

To a solution of example 44 (20 mg, 0.04 mmol) in DMF (2 ml) under N$_2$ was added benzyl mercaptan (20 ul, 0.2 mmol, 5 eq.). The solution was stirred at room temperature for 18 h, then at 70° C. for 6 h, and partitioned between ethyl acetate and H2O. The organic layer was washed with brine, dried (MgSO$_4$), filtered and concentrated. The crude material was purified by flash chromatography using 1–15% acetone in dichloromethane to give the title compound (15 mg, 58%).

IR (KBr) 3310.21, 3264.90, 2926.45, 2831.95, 1699.87, 1674.74, 1613.05, 1592.37, 1506.49, 1458.07, 1409.78, 1230.24, 1128.31 cm$^{-1}$. MS (FAB) (m/z) 642.1479.

Example 50

N-3,4,5-Trimethoxyphenyl-3-[3-phthalimidyl-isoxazolo[4,5-c]-1,2-dihydro-6-chloroquinolin-2-on-1-yl]phenylacetamide

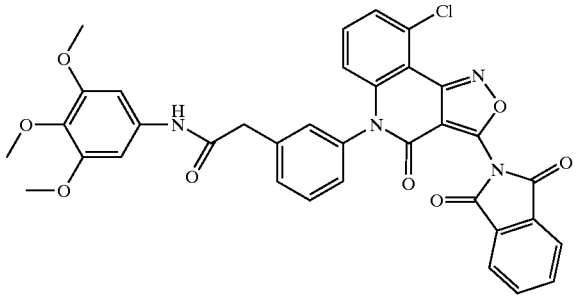

To a solution of example 44 (20 mg, 0.04 mmol) in DMF (2 ml) under $N_2$ was added potassium phthalimide (37 mg, 0.2 mmol, 5 eq.). The reaction was stirred at room temperature for 1 h, then partitioned between ethyl acetate and $H_2O$. The organic layer was washed with brine, dried ($MgSO_4$), filtered and concentrated. The crude material was purified by flash chromatography using 1–10% acetone in dichloromethane to give the title compound (10 mg, 42%).

$^1$H NMR (400 MHz, $CDCl_3$) δ 7.97–7.95 (m, 2H), 7.83–7.81 (m, 2H), 7.57 (t, 1H), 7.50 (d, 1H), 7.38 (d, 1H), 7.31–7.27 (m, 2H), 7.23–7.22 (m, 1H), 6.72 (s, 2H), 6.62 (d, 1H), 3.76 (s, 3H), 3.72 (s, 6H), 3.71 (s, 2H)ppm. MS (FAB) (m/z) 665.1439.

Example 51

N-3,4,5-Trimethoxyphenyl-3-[3-pyridin-2-ylthio-isoxazolo[4,5-c]-1,2-dihydro-6-chloroquinolin-2-on-1-yl]phenylacetamide

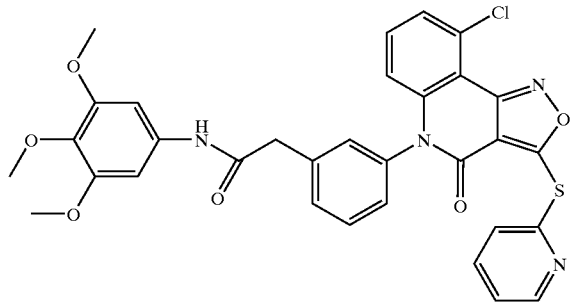

To a solution of example 44 (20 mg, 0.04 mmol) in DMF (2 ml) under $N_2$ was added 2-mercaptopyridine (22 mg, 0.2 mmol, 5 eq.). The reaction was stirred at room temperature for 1 h, then partitioned between ethyl acetate and $H_2O$. The organic layer was washed with brine, dried ($MgSO_4$), filtered and concentrated. The crude material was purified by flash chromatography using 1–15% acetone in dichloromethane to give the desired compound (19 mg, 84%).

$^1$H NMR (400 MHz, $CDCl_3$) δ 8.60–8.58 (m, 1H), 7.75 (t, 1H), 7.72 (d, 1H), 7.68 (t, 1H), 7.60 (d, 1H), 7.51 (s, 1H), 7.33–7.31 (m, 2H), 7.26–7.22 (m, 2H), 6.84 (s, 2H), 6.62 (d, 1H), 3.82 (s, 6H), 3.77 (s, 3H), 3.75 (s, 2H)ppm. MS (FAB) (m/z) 629.1242.

Example 52

N-3,4,5-Trimethoxyphenyl-3-[3-phenylthio-isoxazolo[4,5-c]-1,2-dihydro-6-chloroquinolin-2-on-1-yl]phenylacetamide

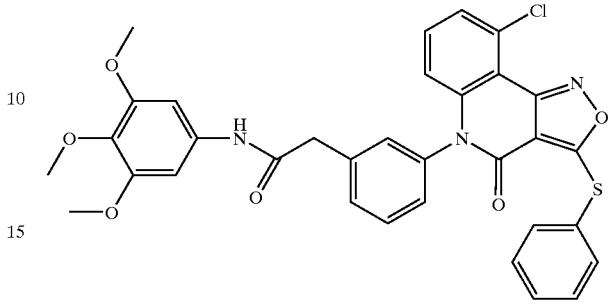

To a solution of example 44 (4 mg, 0.007 mmol) in DMF (0.5 ml) under $N_2$ was added sodium phenylthiolate (5 mg, 0.035 mmol, 5 eq.). The reaction was stirred at room temperature for 18 h, then at 60° C. for 3 h, and partitioned between ethyl acetate and $H_2O$. The organic layer was washed with brine, dried ($MgSO_4$), filtered and concentrated. The crude material was purified by flash chromatography using 1–10% acetone in dichloromethane to give the desired compound (2 mg, 47%).

$^1$H NMR (400 MHz, $CDCl_3$) δ 7.69–7.63 (m, 3H), 7.53–7.45 (m, 4H), 7.33–7.23 (m, 4H), 6.85 (s, 2H), 6.62 (d, 1H), 3.86 (s, 6H), 3.82 (s, 2H), 3.78 (s, 3H)ppm. MS (FAB) (m/z) 628.1313.

Example 53

N-3,4,5-Trimethoxyphenyl-3-[3-((2-methoxy-1-hydroxy-ethan-2-al)amidyl)-isoxazolo[4,5-c]-1,2-dihydro-6-chloroquinolin-2-on-1-yl]phenylacetamide

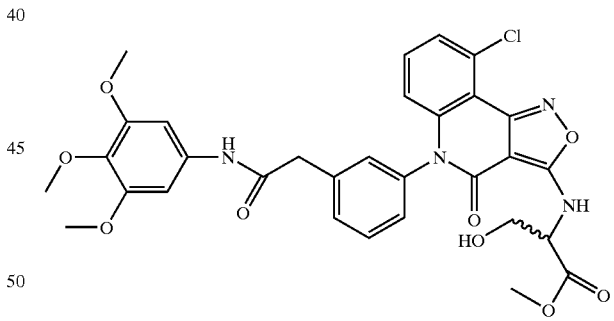

To a solution of example 44 (50 mg, 0.09 mmol) in DMF (5 ml) under $N_2$ was added D,L-serine methyl ester hydrochloride (70 mg, 0.45 mmol, 5 eq.), then diisopropylethylamine (50 ul, 0.27 mmol, 3 eq). It was stirred at room temperature for 2 h, and then partitioned between ethyl acetate and 0.1N HCl. The organic layer was washed with $H_2O$, brine, dried ($MgSO_4$), filtered and concentrated. The crude material was purified by flash chromatography using 1–30% acetone in dichloromethane to give the title compound (33 mg, 58%).

MS (ES) (m/z) 637.2 [M+1]. IR (KBr) 3676.62, 3361.32, 3017.09, 1748.50, 1669.24, 1600.15, 1507.87, 1464.59, 1452.69, 1412.75, 1286.17, 1267.41, 1131.66, 1148.36 $cm^{-1}$.

Example 54

N-3,4,5-Trimethoxyphenyl-3-[3-(4-fluoroanilino)-isoxazolo[4,5-c]-1,2-dihydro-6-chloroquinolin-2-on-1-yl]phenylacetamide

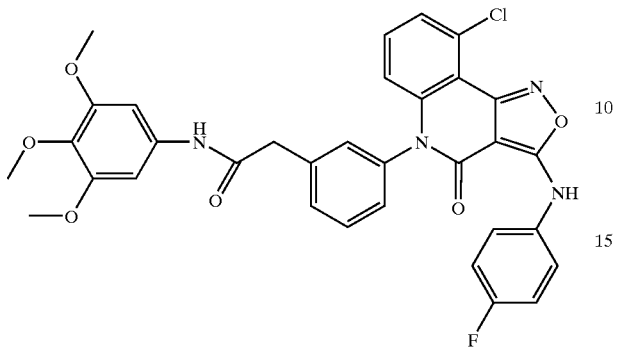

To a solution of example 44 (50 mg, 0.09 mmol) in DMF (5 ml) under $N_2$ was added 4-fluoroaniline (26 ul, 0.27 mmol, 3 eq.) then diisopropylethylamine (50 ul, 0.27 mmol, 3 eq). The reaction was stiffed at room temperature for 7 h, and partitioned between ethyl acetate and 0.1N HCl. The organic layer was washed with $H_2O$, brine, dried ($MgSO_4$), filtered and concentrated. The crude material was purified by flash chromatography using 1–15% acetone in dichloromethane to give the title compound (37 mg, 66%).

$^1$H NMR (400 MHz, $CDCl_3$) δ 7.63–7.60 (m, 2H), 7.52 (d, 1H), 7.34 (m, 2H), 7.28–7.18 (m, 3H), 7.05 (t, 2H), 6.83 (s, 2H), 6.59 (d, 1H), 3.79 (s, 6H), 3.78 (s, 3H)ppm. MS (FAB) (m/z) 629.1611.

Example 55

N-3,4,5-Trimethoxyphenyl-3-[3-anilino-isoxazolo[4,5-c]-1,2-dihydro-6-chloroquinolin-2-on-1-yl]phenylacetamide

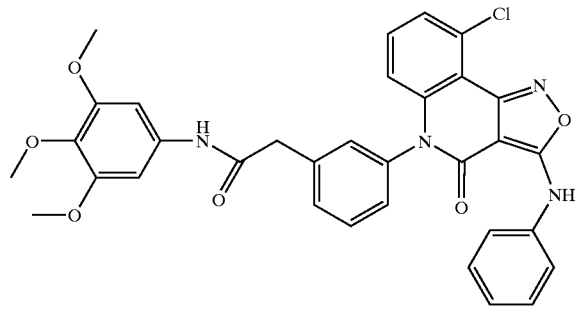

To a solution of example 44 (50 mg, 0.09 mmol) in DMF (5 ml) under $N_2$ was added aniline (25 ul, 0.27 mmol, 3 eq.), then diisopropylethylamine (50 ul, 0.27 mmol, 3 eq). The reaction was stirred at room temperature for 19 h, and partitioned between ethyl acetate and 0.1N HCl. The organic layer was washed with $H_2O$, brine, dried ($MgSO_4$), filtered and concentrated. The crude material was purified by flash chromatography using 1–15% acetone in dichloromethane to give the desired compound the title compound (34 mg, 61%).

$^1$H NMR (400 MHz, $CDCl_3$) δ 7.63 (t, 1H), 7.53 (d, 1H), 7.44–36 (m, 5H), 7.30–7.21 (m, 3H), 7.15 (t, 1H), 6.82 (s, 2H), 6.61 (d, 1H), 3.81 (s, 6H), 3.79 (s, 3H), 3.77 (s, 2H)ppm. MS (FAB) (m/z) 611.1703.

Example 56

N-3,4,5-Trimethoxyphenyl-3-[3-(2-methoxyethylamidyl)-isoxazolo[4,5-c]-1,2-dihydro-6-chloroquinolin-2-on-1-yl]phenylacetamide

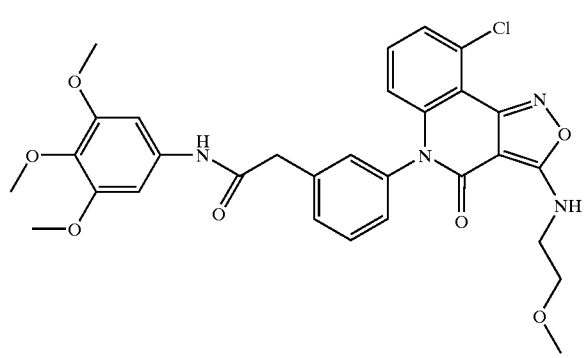

To a solution of example 44 (50 mg, 0.09 mmol) in DMF (5 ml) under $N_2$ was added 2-methoxyethylamine (24 ul, 0.27 mmol, 3 eq.) then diisopropylethylamine (50 ul, 0.27 mmol, 3 eq). The mixture was stirred at room temperature for 10 min, then partitioned between ethyl acetate and 0.1N HCl. The organic layer was washed with $H_2O$, brine, dried ($MgSO_4$), filtered and concentrated. The crude material was purified by flash chromatography using 1–30% acetone in dichloromethane to give the desired compound the title compound (31 mg, 59%).

MS (FAB) (m/z) 593.1809. IR (KBr) 1668.82, 1639.51, 1600.75, 1508.25, 1452.72, 1131.93 $cm^{-1}$.

Example 57

N-3,4,5-Trimethoxyphenyl-3-[3-((2-methoxy-1-prop-2-yl-ethan-2-al)amidyl)-isoxazolo[4,5-c]-1,2-dihydro-6-chloroquinolin-2-on-1-yl]phenylacetamide

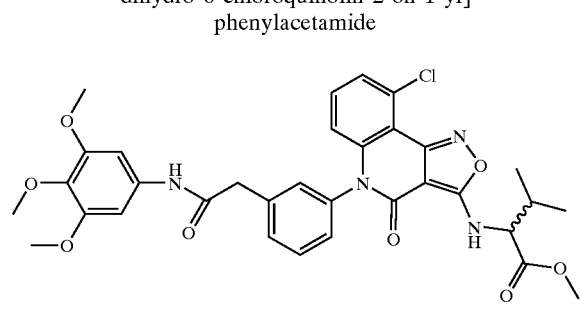

To a solution of example 44 (50 mg, 0.09 mmol) in DMP (5 ml) under $N_2$ was added D,L-valine methyl ester hydrochloride (76 mg, 0.45 mmol, 5 eq.), then diisopropylethylamine (50 ul, 0,27 mmol, 3 eq). The mixture was stirred at room temperature for 2 h, then partitioned between ethyl acetate and 0.1N HCl. The organic layer was washed with $H_2O$, brine, dried ($MgSO_4$), filtered and concentrated. The crude material was purified by flash chromatography using 1–15% acetone in dichloromethane to give the title compound (38 mg, 66%), as a mixture of enantiomers.

MS (FAB) (m/z) 649.2059. IR (KBr) 3010.50, 1744.23, 1667.18, 1638.41, 1599.86, 1508.11, 1464.67, 1452.64, 1412.44, 1285.83, 1266.55, 1235.18, 1149.15, 1132.61 $cm^{-1}$.

Example 58

N-3,4,5-Trimethoxyphenyl-3-[3-(2-methoxycarbonylpyrrolidinyl)-isoxazolo[4,5-c]-1,2-dihydro-6-chloroquinolin-2-on-1-yl]phenylacetamide

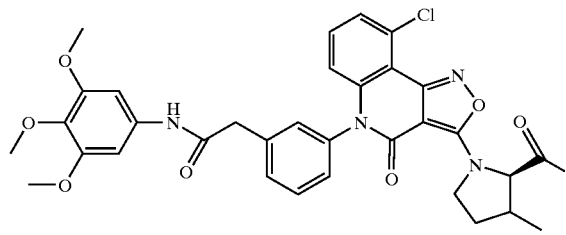

To a solution of example 44 (50 mg, 0.09 mmol) in DMF (5 ml) under $N_2$ was added L-proline methyl ester hydrochloride (75 mg, 0.45 mmol, 5 eq.), then diisopropylethylamine (75 ul, 0.41 mmol, 4.5 eq). The reaction was stirred at room temperature for 1 h 15 min, then partitioned between ethyl acetate and 0.1N HCl. The organic layer was washed with $H_2O$, brine, dried ($MgSO_4$), filtered and concentrated. The crude material was purified by flash chromatography using 1–20% acetone in dichloromethane to give the title compound (56 mg, 90%).

MS (FAB) (m/z) 647.1896. IR (KBr) 1744.62, 1669.01, 1603.27, 1594.03, 1498.34, 1452.51, 1412.85, 1287.30, 1235.18, 1132.45 cm$^{-1}$.

Example 59

N-3,4,5-Trimethoxyphenyl-3-[3-((2-methoxy-1-benzyl-ethan-2-al)amidyl)-isoxazolo[4,5-c]-1,2-dihydro-6-chloroquinolin-2-on-1-yl]phenylacetamide

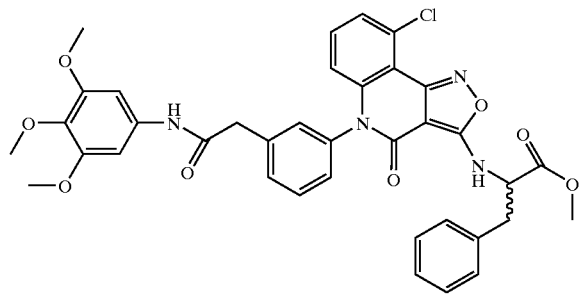

To a solution of example 44 (50 mg, 0.09 mmol) in DMF (5 ml) under $N_2$ was added D,L-phenylalanine hydrochloride (97 mg, 0.45 mmol, 5 eq.), then diisopropylethylamine (75 ul, 0.41 mmol, 4.5 eq). It was stirred at room temperature for 24 h, then partitioned between ethyl acetate and 0.1N HCl. The organic layer was washed with $H_2O$, brine, dried ($MgSO_4$), filtered and concentrated. The crude material was purified by flash chromatography using 1–15% acetone in dichloromethane to give the title compound (41 mg, 65%) as a mixture of enantiomers.

MS (FAB) (m/z) 697.2075. IR (KBr) 1748.03, 1668.31, 1638.93, 1599.78, 1508.08, 1452.64, 1412.32, 1284.48, 1267.21, 1235.18, 1132.20 cm$^{-1}$.

Example 60

N-3,4,5-Trimethoxyphenyl-3-[3-((2-methoxy-1-methyl-ethan-2-al)amidyl)-isoxazolo[4,5-c]-1,2-dihydro-6-chloroquinolin-2-on-1-yl]phenylacetamide

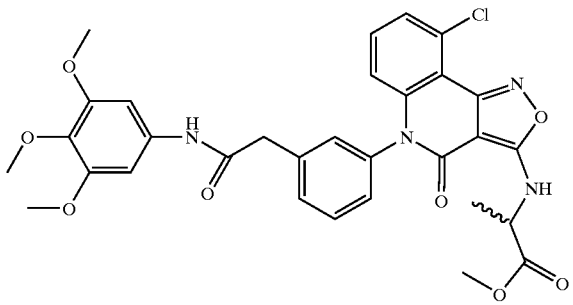

To a solution of example 44 (36 mg, 0.07 mmol) in DMF (3.5 ml) under $N_2$ was added (D,L) ananine methyl ester (49 mg, 0.35 mmol, 5 eq.), then triethylamine (30 ul, 0.21 mmol, 3 eq.). The solution was stirred at room temperature for 3 h, then partitioned between ethyl acetate and $H_2O$. The organic layer was washed with brine, dried ($MgSO_4$), filtered and concentrated. The crude material was purified by flash chromatography using 1–10% acetone in dichloromethane to give the title compound (16 mg, 40%) as a mixture of enantiomers.

Anal. Calc. for $C_{31}H_{29}ClN_4O_8$; Theoretical: C, 59.95, H, 4.71, N, 9.02; Found C, 59.90, H, 5.08, 8.52%. IR (KBr) 1746.09, 1671.16, 1638.64, 1598.09, 1506.60, 1449.88, 1410.66, 1280.66, 1267.05, 1229.78, 1151.16, 1128.33, 789.32 cm$^{-1}$.

Example 61

N-3,4,5-Trimethoxyphenyl-3-[3-((2-methoxy-ethan-2-al)amidyl)-isoxazolo[4,5-c]-1,2-dihydro-6-chloroquinolin-2-on-1-yl]phenylacetamide

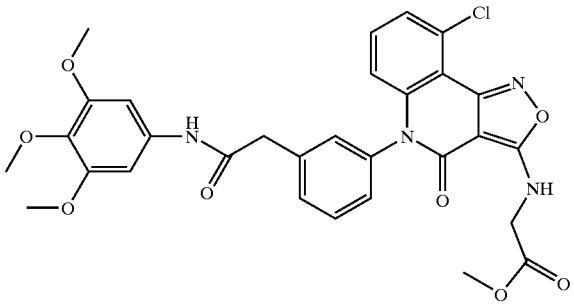

To a solution of example 44 (23 mg, 0.04 mmol) in DMF (2 ml) under $N_2$ was added triethylamine (26 l, 0.2 mmol, 5 eq.), then glycine methyl ester (15 mg, 0.12 mmol, 3 eq.). The solution was stirred at room temperature for 3 h, and partitioned between ethyl acetate and $H_2O$. The organic layer was washed with brine, dried ($MgSO_4$), filtered and concentrated. The crude material was purified by flash chromatography using 1–10% acetone in dichloromethane to give the title compound (16 mg, 40%).

MS (FAB) (m/z) 607.1604. IR (KBr) 1744.26, 1659.82, 1599.86, 1507.20, 1450.94, 1420.55, 1412.06, 1265.82, 1230.04, 1205.12, 1128.92 cm$^{-1}$.

Example 62

N-3,4,5-Trimethoxyphenyl-3-[3-ethoxy-isoxazolo[4,5-c]-1,2-dihydro-6-chloroquinolin-2-on-1-yl]phenylacetamide

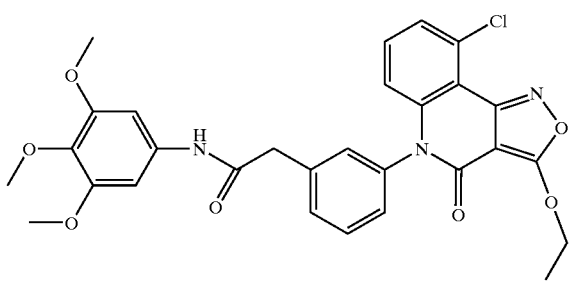

To a solution of example 44 (29 mg, 0.05 mmol) in THF (3 ml) under $N_2$ was added a solution of 21% sodium ethoxide in ethanol (40 ul, 0.1 mmol, 2 eq.). It was stirred at room temperature for 30 min, then partitioned between ethyl acetate and $H_2O$. The organic layer was washed with brine, dried ($MgSO_4$), filtered and concentrated. The crude material was purified by flash chromatography using 1–30% acetone in dichloromethane to give the title compound (4.5 mg, 16%).

$^1$H NMR (400 MHz, $CDCl_3$) δ 7.61 (t, 1H), 7.48 (d, 1H), 7.34 (s, 1H), 7.31–7.20 (m, 3H), 6.87 (s, 2H), 6.59 (dd, 1H), 4.76 (q, 2H), 3.87 (s, 6H), 3.78 (s, 5H), 1.56 (t, 3H)ppm. MS (FAB) (m/z) 564.1545.

Example 63

N-3,4,5-Trimethoxyphenyl-3-[3-(1-methylethoxy)-isoxazolo[4,5-c]-1,2-dihydro-6-chloroquinolin-2-on-1-yl]phenylacetamide

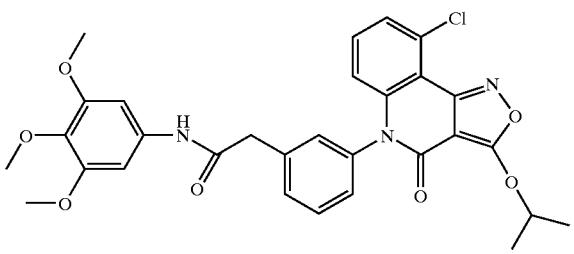

To a solution of example 44 (50 mg, 0.09 mmol) in THF (5 ml) under $N_2$ was added 0.95M sodium isopropoxide (100 ul, 1.2 eq.). The reaction was stirred at room temperature for 6 h, then set in a freezer for 17 h. Additional 0.95M sodium isopropoxide (150 ul, 1.8 eq.) was added, stirred for 2 h, and then partitioned between ethyl acetate and $H_2O$. The organic layer was washed with brine, dried ($MgSO_4$), filtered and concentrated. The crude material was purified by flash chromatography using 1–10% acetone in dichloromethane to give the title compound (9 mg, 17%).

MS (FAB) (m/z) 578.1689. IR (KBr) 1680.23, 1623.90, 1596.74, 1508.46, 1131.81 $cm^{-1}$.

Example 64

N-3,4,5-Trimethoxyphenyl-3-[3-(1-methoxy)-isoxazolo[4,5-c]-1,2-dihydro-6-chloroquinolin-2-on-1-yl]phenylacetamide

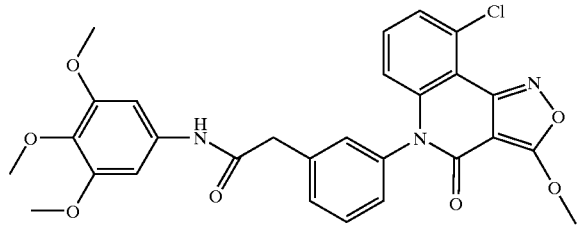

To a solution of example 44 (7 mg, 0.01 mmol) in MeOH (2.5 ml) under $N_2$ was added 0.95M sodium methoxide (18 ul, 2 eq.). The solution was stirred at room temperature for 6 h, and partitioned between ethyl acetate and $H_2O$. The organic layer was washed with brine, dried ($MgSO_4$), filtered and concentrated. The crude material was purified by flash chromatography using 1–10% acetone in dichloromethane to give the title compound (2.5 mg, 35%).

$^1$H NMR (400 MHz, $CDCl_3$) δ 7.61 (t, 1H), 7.48 (d, 1H), 7.36 (s, 1H), 7.32–7.20 (m, 4H), 6.89 (s, 2H), 6.60 (dd, 1H), 4.37 (s, 3H), 3.84 (s, 6H), 3.79 (s, 3H), 3.77 (s,2H)ppm. MS (FAB) (m/z) 550.1387.

Example 65

N-3,4,5-Trimethoxyphenyl-3-[oxazolo[4,5-c]-1,2-dihydro-6-chloroquinolin-2-on-1-yl]phenylacetamide

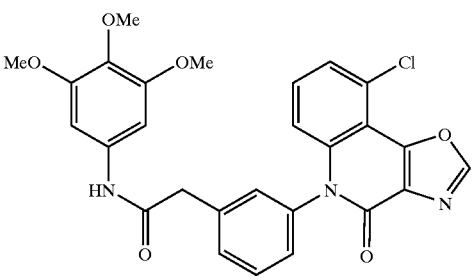

Compound from preparation 57 (122 mg, 0.226 mmol) and 2N NaOH in MeOH (2.5 ml, 5.0 mmol) were allowed to react in DMF (5 ml) at room temperature for 16 h. Dilution with EtOAc, extraction with $H_2O$ (3×) and brine, drying ($MgSO_4$), filtration, concentration, and purification by column chromatography (silica gel, hexanes/EtOAc gradient) gave the title compound (74 mg, 63%).

$^1$H NMR (400 MHz, $d_6$-DMSO) d 10.36 (s, $1H_1$), 8.95 (s, 1H), 7.55–7.45 (m, 2H), 7.43–7.38 (m, 2H), 7.26 (s, 1H), 7.21 (d, 1H, J=7.3 Hz), 6.97 (s, 2H), 6.57 (d, 1H, J=8.3 Hz), 3.70 (s, 2H), 3.65 (s, 6H), 3.53 (s, 3H)ppm. Mass spectrum (ES) (m/z) 520.2 [M+1].

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Vincristine, epirubicin, daunorubicin, doxorubicin, and etoposide are oncolytics that are substrates of MRP1. See Cole, et. al., "Pharmacological Characterization of Multidrug Resistant MRP-transfected Human Tumor Cells", *Cancer Research*, 54:5902–5910, 1994. Since MRP1 is ubiquitous in mammals, particularly humans, Nooter, K, et. al., "Expression of the Multidrug Resistance-Associated Protein (MRP) Gene in Human Cancers", *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung (small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay which rapidly and accurately measured the activity of the tested compound in inhibiting MRP1 or MDR1. Assays useful for evaluating this reversing capability are well known in the art. See, e.g., T. McGrath et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., *Cancer Research*, 54: 5902–5910, 1994.

Assay for Reversal of MRP1-Mediated Doxorubicin Resistance and MDR1-Mediated Vincristine Resistance: HL60/Adr and HL60/Vinc are continuous cell lines, which were selected for doxorubicin and vincristine resistance respectively by culturing HL60, a human acute myeloblastic leukemia cell line, in increasing concentrations of doxorubicin or vincristine until a highly resistant variant was attained.

HL60/Adr and HL60/Vinc cells were grown in RPMI 1640 (Gibco) containing 10% fetal bovine serum (FBS) and 50 $\mu$g/ml GENTAMICIN™ (Sigma). Cells were harvested; washed twice with assay medium (same as culture media); counted; and diluted to $1\times10^5$ cells/ml in assay medium. One hundred microliters of cells were aliquoted into wells of a 96 well tissue culture plate. Two columns of each 96 well plate served as a negative control and received assay medium containing no cells.

Test compounds and reference compounds were dissolved in dimethyl sulfoxide (DMSO) at a concentration of 5 mM. Samples were diluted in assay medium and 25 $\mu$l of each test compound was added to 8 wells. Assay standards were run in quadruplicate. Assay media was added to half of the wells and doxorubicin to the other half of the wells to achieve a final volume of 150 $\mu$l per well.

The plates were incubated at 37° C. for 72 hours in a humidified incubator with a 5% carbon dioxide atmosphere. Cell viability and vitality was measured by oxidation of a alamarBlue™ fluorescent dye using standard conditions. The plates were incubated for 3 hours at 37° C. Fluorescence was determined using 550 nm excitation and 590 nm emission using a microtitre plate reader.

The ability of a test compound to reverse the resistance of HL60/Adr and HL60/Vinc cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration minimally inhibits the growth of HL60/Adr or HL60/Vinc cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/Adr cell line over the HL60/Vinc cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645-1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdernal, subcutaneous, intravenous, intramuscular, and intranasal. Such formulations are prepared in a manner well known in the pharmaceutical art and comprise at least one active compound of formula I.

The present invention also includes methods employing pharmaceutical formulations which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices which deliver the formulation in an appropriate manner.

The following formulation examples are illustrative only and are not intended to limit the scope of the invention in any way. "Active ingredient(s)" means a compound according to formula I or a pharmaceutical salt or solvate thereof optionally with one or more oncolytics.

Formulation Example 1

Hard gelatin capsules containing the following ingredients are prepared:

| Ingredient | Quantity (mg/capsule) |
|---|---|
| N-3,4,5-trimethoxyphenyl-3-[3-azidomethyl-isoxazolo[4,5-c]-1,2-dihydro-6-chloro-quinolin-2-on-1-yl]phenylacetamide | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/capsule) |
|---|---|
| N-3,4,5-trimethoxyphenl-3-[3-methyl-isoxazolo[4,5-c]-1,2-dihydro-6-fluoro-quinolin-2-on-1-yl]phenylacetamide | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| N-3,4,5-trimethoxyphenyl-3-[3-methyl isoxazolo[4,5-c]-1,2-dihydro-6-methoxy-quinolin-2-on-1-yl]phenylacetamide | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/capsule) |
| --- | --- |
| N-3,4,5-trimethoxyphenyl-3-[3-methyl-isoxazolo[4,5-c]-1,2-dihydro-5-(4-methoxyphenyl)-quinolin-2-on-1-yl]phenylacetamide | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| N-3,4,5-trimethoxyphenyl-3-(3-methyl-isoxazolo[4,5-c]-1,2-dihydro-6-carboxy-quinolin-2-on-1-yl]phenylacetamide | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| N-3,4,5-trimethoxyphenyl-3-[3-((2-methoxy-1-benzyl-ethan-2-al)amidyl)-isoxazolo[4,5-c]-1,2-dihydro-6-chloroquinolin-2-on-1-yl]phenylacetamide | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| N-3,4,5-trimethoxyphenyl-3-[3-phenylthio-isoxazolo[4,5-c]-1,2-dihydro-6-chloroquinolin-2-on-1-yl]phenylacetamide | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| N-3,4,5-trimethoxyphenyl-3-[3-methyl-isoxazolo[4,5-c]-1,2-dihydro-5-(4-trifluoromethylphenyl)-quinolin-2-on-1-yl]phenylacetamide | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| N-3,4,5-trimethoxyphenyl-3-[3-methyl-isoxazolo[4,5-c]-1,2-dihydro-6-iodoquinolin-2-on-1-yl]phenylacetamide | 250.0 mg |
| Isotonic saline | 1000 ml |

Formulation Example 10

A topical formulation may be prepared as follows:

| Ingredient | Quantity |
| --- | --- |
| N-3,4,5-trimethoxyphenyl-3-[3-methyl-isoxazolo[4,5-c]-1,2-dihydro-6-(thien-2-yl)-quinolin-2-on-1-yl]phenylacetamide | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity (mg/capsule) |
| --- | --- |
| N-3,4,5-trimethoxyphenyl-3-[3-(1-methoxy)-isoxazolo[4,5-c]-1,2-dihydro-6-chloroquinolin-2-on-1-yl]phenylacetamide | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 24 mm. This diffusion matrix is then cut to form individual tablets having the appropriate size.

Another preferred formulation employed in the methods of the present invention employs transdernal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

We claim:

1. A compound of formula I:

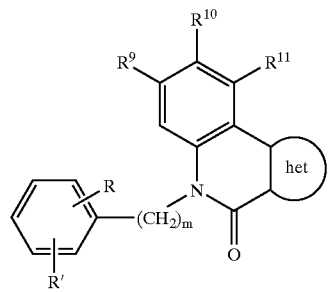

where:
het is a five (5) membered heteroaryl ring containing N and a second heteroatom selected from N, O, or S;
wherein the non-fused carbon atom of the heteroaryl ring is optionally substituted with $C_1$–$C_6$ alkyl, aryl, aryl substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro, heterocycle, heterocycle substituted 1 or 2 times independently with a $C_1$–$C_6$ alkyl, halo, benzyl, phenyl, or trifluoromethyl, an amino acid ester, $CH_2OH$, $CH_2O$-heterocycle, halo, $CH_2N_3$, $CH_2SR^1$, $CH_2NR^4R^5$, $OR^1$, $SR^{12}$, $S(CH_2)_n$-phenyl, or $NR^4R^5$; provided that when het is pyrazole or imidazole, the saturated nitrogen of the het ring is optionally substituted with $C_1$–$C_4$ alkyl;
R is $(CH_2)_{m'}CHR^1NHR^2$, $O(CH_2)_2NHR^2$, $(CH_2)_{m'}COR^3$, $NHR^2$, and $(CH_2)_{m'}CHR^1NR^4R^5$;
R' is hydrogen, hydroxy, or $O(C_1$–$C_6$ alkyl optionally substituted with phenyl or $C_3$–$C_7$ cycloalkyl);
m and m' are independently at each occurrence 0, 1, or 2;
$R^1$ is independently at each occurrence hydrogen or $C_1$–$C_6$ alkyl;
$R^2$ is hydrogen, $COR^6$, $CH_2R^{6'}$, $SO_2R^7$, or a moiety of the formula

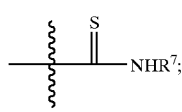

$R^3$ is hydrogen, hydroxy, $C_1$–$C_6$ alkoxy, an amino acid ester, an amino acid, or $NR^4R^5$, wherein the amino acid is selected from the group consisting of alanine, asparagine, cysteine, glutamine, glycine, isoleucine, leusine, methionine, phenylalanine, proline, serine threonine, tryptophan, tyrosine, valine, aspartic acid, glutamic acid, arginine, histidine, and lysine;

$R^4$ is hydrogen or $C_1$–$C_6$ alkyl;

$R^5$ is hydrogen, $C_1$–$C_6$ alkyl, $C_6$–$C_{10}$ bicycloalkyl, ($C_1$–$C_4$ alkyl)-phenyl, ($C_1$–$C_4$ alkyl)-$CO_2R^1$, $CH_2CO_2R^1$, aryl, aryl substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro, $(CH_2)_nCHR^8NHC(O)OC(CH_3)_3$, $(CH_2)_nNH_2$, $(CH_2)_2NHCOR^6$, $(CH_2)_2OR^1$, $(CH_2)_q$-heterocycle, $(CH_2)_q$ (heterocycle substituted 1 or 2 times independently with a $C_1$–$C_6$ alkyl, halo, benzyl, phenyl, or trifluoromethyl), or $R^4$ and $R^5$, together with the nitrogen to which they are attached, combine to form a pyrrolidin-1-yl, piperidin-1-yl, hexamethyleneimin-1-yl, or morpholin-4-yl ring;

n is 1, 2, 3, or 4;

q is 0, 1, 2, or 3;

$R^6$ is $C_1$–$C_6$ alkyl, $C_3$–$C_6$ cycloalkyl substituted once with a phenyl, substituted phenyl, or $CO_2R^1$ group, aryl, aryl substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro, tert-butoxy, $(CH_2)_q$-heterocycle, $(CH_2)_q$ (heterocycle substituted 1 or 2 times independently with a $C_1$–$C_6$ alkyl, halo, benzyl, phenyl, or trifluoromethyl), $(CH_2)_nS(O)_rR^1$, $C(CH_3)_2CH_2N(R^1)_2$, $(CH_2)_nCHR^8NHC(O)OC(CH_3)_3$, $(CH_2)_nCHR^8NH_2$, $(CH_2)_2NH$-aryl, or $NHR^7$;

$R^{6'}$ is $C_1$–$C_6$ alkyl, $C_3$–$C_6$ cycloalkyl substituted once with a phenyl, substituted phenyl, or $CO_2R^1$ group, aryl, aryl substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro, $(CH_2)_q$-heterocycle, $(CH_2)_q$ (heterocycle substituted 1 or 2 times independently with a $C_1$–$C_6$ alkyl, halo, benzyl, phenyl, or trifluoromethyl), $(CH_2)_nS(O)_rR^1$, $C(CH_3)_2CH_2N(R^1)_2$, $(CH_2)_nCHR^8NH-C(O)OC(CH_3)_3$, $(CH_2)_nCHR^8NH_2$, or $(CH_2)_2NH$-aryl;

r is 0, 1, or 2;

$R^7$ is $C_1$–$C_6$ alkyl, phenyl, or phenyl substituted from 1 to 3 times independently with $C_{1-C6}$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro;

$R^8$ is hydrogen or $CO_2R^1$; and $R^9$, $R^{10}$, and $R^{11}$ are independently at each occurrence hydrogen, halo, $CO_2R^1$, aryl, aryl substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro, thiophene, $C_1$–$C_4$ alkoxy, ($C_1$–$C_3$ alkyl)-phenyl, or $C_2$–$C_6$ alkenyl;

$R^{12}$ is $C_1$–$C_6$ alkyl, ($C_1$–$C_4$ alkyl)-phenyl, aryl, aryl substituted from 1 to 3 times independently with $C_1$–$C_6$ alkyl, $C_1$–$C_4$ alkoxy, halo, hydroxy, trifluoromethyl, $N(R^1)_2$, $SO_2N(R^1)_2$, NH-Pg, $C_1$–$C_6$ alkoxy, benzyloxy, $CO_2R^1$, $C_5$–$C_7$ cycloalkyl, trifluoromethoxy, or nitro, heterocycle or heterocycle substituted 1 or 2 times independently with a $C_1$–$C_6$ alkyl, halo, benzyl, phenyl, or trifluoromethyl; or a pharmaceutical salt thereof; provided that if $R^9$ and $R^{10}$ are hydrogen and $R^{11}$ is chloro, then het is not

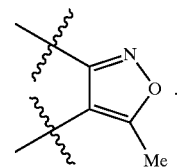

2. The compound according to claim 1 where m is 0 and R is at the meta position.

3. The compound according to claim 2 where R is $(CH_2)_{m'}CHR^1NHR^2$ and m' is 0 and $R^1$ is methyl.

4. The compound according to claim 3 where $R^2$ is 3,4,5-trimethoxybenzyl.

5. The compound according to claim 2 where R is $(CH_2)_{m'}COR^3$ and m' is 0 or 1.

6. The compound according to claim 5 where $R^3$ is (3,4,5-trimethoxyphenyl)amino, (4-aminosulfonylphenyl)amino, or (6-methoxyquinolin-8-yl)amino.

7. The compound according to claim 2 where R is $(CH_2)_{m'}CHR^1NR^4R^5$ and m' is 0, and $R^1$ and $R^4$ is hydrogen.

8. The compound according to claim 7 where $R^5$ is 5-methylisoxazol-3-yl, 3,5-dimethoxy-4-hydroxybenzyl, or 3,4,5-trimethoxybenzyl.

9. A method of inhibiting MRP1 in a mammal which comprises administering to a mammal in need thereof an effective amount of a compound of formula I, as defined in claim 1, or a pharmaceutical salt thereof.

10. The method according to claim 9 where the mammal is a human.

11. The method according to claim 10 where the compound of formula I is a compound where m is 0 and R is at the meta position.

12. The method according to claim 11 where the compound of formula I is a compound where R is $(CH_2)_{m'}CHR^1NHR^2$ and m' is 0 and $R^1$ is methyl.

13. The method according to claim 12 where the compound of formula I is a compound where $R^2$ is 3,4,5-trimethoxybenzyl.

14. The method according to claim 11 where the compound of formula I is a compound where R is $(CH_2)_{m'}COR^3$ and m' is 0 or 1.

15. The method according to claim 14 where the compound of formula I is a compound where $R^3$ is (3,4,5-trimethoxyphenyl)amino, (4-aminosulfonylphenyl)amino, or (6-methoxyquinolin-8-yl)amino.

16. The method according to claim 11 where the compound of formula I is a compound where R is $(CH_2)_{m'}CHR^1NR^4R^5$ and m' is 0, and $R^1$ and $R^4$ is hydrogen.

17. The method according to claim 16 where the compound of formula I is a compound where $R^5$ is 5-methylisoxazol-3-yl, 3,5-dimethoxy4-hydroxybenzyl, or 3,4,5-trimethoxybenzyl.

18. A pharmaceutical formulation comprising a compound of formula I, as defined in claim 1, or a pharmaceutical salt thereof; in combination with one or more pharmaceutical carriers, diluents, or excipients therefor.

19. A pharmaceutical composition for inhibiting MRP1 in a mammal which comprises an effective amount of a compound of formula I, as defined in claim 1, or a pharmaceutical salt thereof.

20. The composition according to claim 19 where the mammal is a human.

21. The composition according to claim 20 where the compound of formula I is a compound where m is 0 and R is at the meta position.

22. The composition according to claim 21 where the compound of formula I is a compound where R is $(CH_2)_{m'}CHR^1NHR^2$ and m' is 0 and $R^1$ is methyl.

23. The composition according to claim 22 where the compound of formula I is a compound where $R^2$ is 3,4,5-trimethoxybenzyl.

24. The composition according to claim 21 where the compound of formula I is a compound where R is $(CH_2)_{m'}COR^3$ and m' is 0 or 1.

25. The composition according to claim 24 where the compound of formula I is a compound where $R^3$ is (3,4,5-trimethoxyphenyl)amino, (4-aminosulfonylphenyl)amino, or (6-methoxyquinolin-8-yl)amino.

26. The composition according to claim 21 where the compound of formula I is a compound where R is $(CH_2)_{m'}CHR^1NR^4R^5$ and m' is 0, and $R^1$ and $R^4$ is hydrogen.

27. The composition according to claim 26 where the compound of formula I is a compound where $R^5$ is 5-methylisoxazol-3-yl, 3,5-dimethoxy-4-hydroxybenzyl, or 3,4,5-trimethoxybenzyl.

* * * * *